(12) United States Patent
Desai

(10) Patent No.: US 12,133,844 B2
(45) Date of Patent: *Nov. 5, 2024

(54) METHODS OF TREATING EPITHELIOID CELL TUMORS

(71) Applicant: Abraxis BioScience, LLC, Summit, NJ (US)

(72) Inventor: Neil P. Desai, Pacific Palisades, CA (US)

(73) Assignee: Abraxis BioScience, LLC, Summit, NJ (US)

( * ) Notice: Subject to any disclaimer, the term of this patent is extended or adjusted under 35 U.S.C. 154(b) by 751 days.

This patent is subject to a terminal disclaimer.

(21) Appl. No.: 17/165,652

(22) Filed: Feb. 2, 2021

(65) Prior Publication Data

US 2021/0322391 A1  Oct. 21, 2021

Related U.S. Application Data

(63) Continuation of application No. 15/737,936, filed as application No. PCT/US2016/040170 on Jun. 29, 2016, now Pat. No. 10,973,806.

(60) Provisional application No. 62/186,252, filed on Jun. 29, 2015.

(51) Int. Cl.
 A61K 31/436 (2006.01)
 A61K 9/00 (2006.01)
 A61K 9/08 (2006.01)
 A61K 9/10 (2006.01)
 A61K 9/19 (2006.01)
 A61K 9/51 (2006.01)
 A61K 38/38 (2006.01)
 A61K 47/42 (2017.01)
 A61P 35/00 (2006.01)
 A61P 35/04 (2006.01)

(52) U.S. Cl.
 CPC .......... A61K 31/436 (2013.01); A61K 9/0019 (2013.01); A61K 9/08 (2013.01); A61K 9/10 (2013.01); A61K 9/19 (2013.01); A61K 9/5169 (2013.01); A61K 38/38 (2013.01); A61K 47/42 (2013.01); A61P 35/00 (2018.01); A61P 35/04 (2018.01)

(58) Field of Classification Search
 None
 See application file for complete search history.

(56) References Cited

U.S. PATENT DOCUMENTS

| | | | |
|---|---|---|---|
| 5,362,478 A | 11/1994 | Desai | |
| 5,439,686 A | 8/1995 | Desai | |
| 5,498,421 A | 3/1996 | Grinstaff | |
| 5,505,932 A | 4/1996 | Grinstaff | |
| 5,508,021 A | 4/1996 | Grinstaff | |
| 5,512,268 A | 4/1996 | Grinstaff | |
| 5,560,933 A | 10/1996 | Soon-shiong | |
| 5,635,207 A | 6/1997 | Grinstaff | |
| 5,639,473 A | 6/1997 | Grinstaff | |
| 5,650,156 A | 7/1997 | Grinstaff | |
| 5,665,382 A | 9/1997 | Grinstaff | |
| 5,665,383 A | 9/1997 | Grinstaff | |
| 5,916,596 A | 6/1999 | Desai | |
| 5,997,904 A | 12/1999 | Magdassi | |
| 6,096,331 A | 8/2000 | Desai | |
| 6,506,405 B1 | 1/2003 | Desai | |
| 6,528,067 B1 | 3/2003 | Magdassi | |
| 6,537,579 B1 | 3/2003 | Desai | |
| 6,565,842 B1 | 5/2003 | Sojomihardjo | |
| 6,652,884 B2 | 11/2003 | Falciani | |
| 6,749,868 B1 | 6/2004 | Desai | |
| 6,753,006 B1 | 6/2004 | Desai | |
| 7,758,891 B2 | 7/2010 | Desai | |
| 7,771,751 B2 | 8/2010 | Desai | |
| 7,780,984 B2 | 8/2010 | Desai | |
| 7,820,788 B2 | 10/2010 | Desai | |
| 7,923,536 B2 | 4/2011 | Desai | |
| 7,981,445 B2 | 7/2011 | De | |
| 8,034,375 B2 | 10/2011 | Desai | |
| 8,034,765 B2 | 10/2011 | De | |
| 8,137,684 B2 | 3/2012 | Desai | |
| 8,138,229 B2 | 3/2012 | Desai | |
| 8,257,733 B2 | 9/2012 | Desai | |
| 8,268,348 B2 | 9/2012 | Desai | |
| 8,314,156 B2 | 11/2012 | Desai | |
| 8,735,394 B2 | 5/2014 | Desai | |
| 8,846,771 B2 | 9/2014 | Desai | |
| 8,853,260 B2 | 10/2014 | Desai | |
| 8,911,786 B2 | 12/2014 | Desai | |
| 8,927,019 B2 | 1/2015 | Desai | |
| 8,999,396 B2 | 4/2015 | Desai | |
| 9,012,518 B2 | 4/2015 | Desai | |
| 9,012,519 B2 | 4/2015 | Desai | |

(Continued)

FOREIGN PATENT DOCUMENTS

AU   2013204187 A1   5/2013
CA     2680207 A1   9/2008
(Continued)

OTHER PUBLICATIONS

US 8,968,752 B2, 03/2015, Desai (withdrawn)
(Continued)

Primary Examiner — Layla Soroush

(74) Attorney, Agent, or Firm — Morrison & Foerster LLP

(57) ABSTRACT

The present invention provides methods and compositions for treating epithelioid cell tumors (such as a PEComa) by administering a composition comprising nanoparticles comprising an mTOR inhibitor and an albumin.

14 Claims, No Drawings

(56) References Cited

U.S. PATENT DOCUMENTS

| | | |
|---|---|---|
| 9,061,014 B2 | 6/2015 | Seward |
| 9,101,543 B2 | 8/2015 | Desai |
| 9,149,455 B2 | 10/2015 | Desai |
| 9,308,180 B2 | 4/2016 | De |
| 9,370,494 B2 | 6/2016 | Yeo |
| 9,393,318 B2 | 7/2016 | Desai |
| 9,399,071 B2 | 7/2016 | Desai |
| 9,399,072 B2 | 7/2016 | Desai |
| 9,446,003 B2 | 9/2016 | Desai |
| 9,511,046 B2 | 12/2016 | Desai |
| 9,561,288 B2 | 2/2017 | Desai |
| 9,585,960 B2 | 3/2017 | Foss |
| 9,597,409 B2 | 3/2017 | Desai |
| 9,675,578 B2 | 6/2017 | Desai |
| 9,724,323 B2 | 8/2017 | Desai |
| 9,820,949 B2 | 11/2017 | Desai |
| 9,855,220 B2 | 1/2018 | Desai |
| 9,884,013 B2 | 2/2018 | Seward |
| 9,962,373 B2 | 5/2018 | Desai et al. |
| 10,076,501 B2 | 9/2018 | Foss et al. |
| 10,258,565 B2 | 4/2019 | Seward |
| 10,328,031 B2 | 6/2019 | Desai |
| 10,413,531 B2 | 9/2019 | Desai |
| 10,527,604 B1 | 1/2020 | Peykov |
| 10,555,912 B2 | 2/2020 | Foss |
| 10,660,965 B2 | 5/2020 | Desai |
| 10,682,420 B2 | 6/2020 | Desai |
| 10,705,070 B1 | 7/2020 | Peykov |
| 10,744,110 B2 | 8/2020 | Desai |
| 10,900,951 B1 | 1/2021 | Peykov |
| 10,973,806 B2 | 4/2021 | Desai |
| 11,320,416 B1 | 5/2022 | Peykov et al. |
| 11,497,737 B2 | 11/2022 | Desai |
| 11,944,708 B2 | 4/2024 | Desai |
| 12,061,183 B2 | 8/2024 | Peykov |
| 2003/0185894 A1 | 10/2003 | Zenoni |
| 2003/0187062 A1 | 10/2003 | Zenoni |
| 2003/0199425 A1 | 10/2003 | Desai |
| 2005/0004002 A1 | 1/2005 | Desai |
| 2006/0263434 A1 | 11/2006 | Desai |
| 2007/0082838 A1 | 4/2007 | De |
| 2007/0117744 A1 | 5/2007 | Desai |
| 2008/0280987 A1 | 11/2008 | Desai |
| 2009/0263483 A1 | 10/2009 | Desai |
| 2009/0304805 A1 | 12/2009 | Desai |
| 2010/0035800 A1 | 2/2010 | Desai |
| 2010/0048499 A1 | 2/2010 | Desai |
| 2010/0112077 A1 | 5/2010 | Desai |
| 2010/0166869 A1 | 7/2010 | Desai |
| 2010/0183728 A1 | 7/2010 | Desai |
| 2010/0215751 A1 | 8/2010 | Desai |
| 2010/0297243 A1 | 11/2010 | Desai |
| 2011/0052708 A1 | 3/2011 | Soon-shiong |
| 2011/0118342 A1 | 5/2011 | De |
| 2011/0151012 A1 | 6/2011 | Desai |
| 2011/0165256 A1 | 7/2011 | Desai |
| 2011/0177088 A1 | 7/2011 | Olive et al. |
| 2011/0196026 A1 | 8/2011 | De |
| 2012/0070502 A1 | 3/2012 | Desai |
| 2012/0076862 A1 | 3/2012 | Desai |
| 2012/0128732 A1 | 5/2012 | Trieu |
| 2012/0189701 A1 | 7/2012 | Desai |
| 2012/0231082 A1 | 9/2012 | Desai |
| 2012/0283205 A1 | 11/2012 | Desai |
| 2012/0308612 A1 | 12/2012 | De |
| 2013/0045240 A1 | 2/2013 | Tao |
| 2013/0071438 A1 | 3/2013 | Desai |
| 2013/0115296 A1 | 5/2013 | Yeo |
| 2013/0195922 A1 | 8/2013 | Desai |
| 2013/0195983 A1 | 8/2013 | Desai |
| 2013/0195984 A1 | 8/2013 | Desai |
| 2013/0202709 A1 | 8/2013 | Desai |
| 2013/0209518 A1 | 8/2013 | Desai |
| 2013/0244952 A1 | 9/2013 | Desai |
| 2013/0266659 A1 | 10/2013 | Desai |
| 2013/0280336 A1 | 10/2013 | Desai |
| 2013/0280337 A1 | 10/2013 | Desai |
| 2014/0017315 A1 | 1/2014 | Desai |
| 2014/0017316 A1 | 1/2014 | Desai |
| 2014/0017323 A1 | 1/2014 | Desai |
| 2014/0023717 A1 | 1/2014 | Desai |
| 2014/0039069 A1 | 2/2014 | Desai |
| 2014/0039070 A1 | 2/2014 | Desai |
| 2014/0056986 A1 | 2/2014 | Desai |
| 2014/0072630 A1 | 3/2014 | Tao |
| 2014/0072631 A1 | 3/2014 | Trieu |
| 2014/0072643 A1 | 3/2014 | Desai |
| 2014/0079787 A1 | 3/2014 | Yeo |
| 2014/0079788 A1 | 3/2014 | Desai |
| 2014/0079793 A1 | 3/2014 | Desai |
| 2014/0080901 A1 | 3/2014 | Desai |
| 2014/0134257 A1 | 5/2014 | Desai |
| 2014/0155344 A1 | 6/2014 | Desai |
| 2014/0170228 A1 | 6/2014 | Desai |
| 2014/0186447 A1 | 7/2014 | Desai |
| 2014/0199403 A1 | 7/2014 | Desai |
| 2014/0199404 A1 | 7/2014 | Heise |
| 2014/0199405 A1 | 7/2014 | Pierce |
| 2014/0271871 A1 | 9/2014 | Desai |
| 2014/0296279 A1 | 10/2014 | Seward |
| 2014/0296353 A1 | 10/2014 | Desai |
| 2014/0302157 A1 | 10/2014 | Desai |
| 2015/0050356 A1 | 2/2015 | Desai |
| 2015/0079177 A1 | 3/2015 | Desai |
| 2015/0079181 A1 | 3/2015 | Desai |
| 2015/0104521 A1 | 4/2015 | Desai |
| 2015/0111960 A1 | 4/2015 | Desai |
| 2015/0157722 A1 | 6/2015 | Foss |
| 2015/0165047 A1 | 6/2015 | Desai |
| 2015/0190519 A1 | 7/2015 | Desai |
| 2015/0313866 A1 | 11/2015 | Desai |
| 2016/0008330 A1 | 1/2016 | Desai |
| 2016/0015681 A1 | 1/2016 | Desai |
| 2016/0015817 A1 | 1/2016 | Benettaib |
| 2016/0151325 A1 | 6/2016 | Desai |
| 2016/0228401 A1 | 8/2016 | Desai |
| 2016/0374952 A1 | 12/2016 | Yeo |
| 2017/0014373 A1 | 1/2017 | Desai |
| 2017/0020824 A1 | 1/2017 | Desai |
| 2017/0049711 A1 | 2/2017 | Desai |
| 2017/0100344 A1 | 4/2017 | Desai |
| 2017/0105951 A1 | 4/2017 | Desai |
| 2017/0157035 A1 | 6/2017 | Seward |
| 2017/0172975 A1 | 6/2017 | Desai |
| 2017/0181988 A1 | 6/2017 | Malhotra |
| 2017/0202782 A1 | 7/2017 | Pierce |
| 2017/0224627 A1 | 8/2017 | Foss |
| 2017/0333384 A1 | 11/2017 | Desai |
| 2017/0340599 A1 | 11/2017 | Desai |
| 2018/0015181 A1 | 1/2018 | Desai |
| 2018/0064679 A1 | 3/2018 | Pierce |
| 2018/0133157 A1 | 5/2018 | Desai |
| 2018/0147139 A1 | 5/2018 | Seward |
| 2018/0153863 A1 | 6/2018 | Desai |
| 2018/0169017 A1 | 6/2018 | Desai |
| 2018/0177770 A1 | 6/2018 | Desai |
| 2018/0177771 A1 | 6/2018 | Desai |
| 2018/0214425 A1 | 8/2018 | Desai |
| 2018/0256551 A1 | 9/2018 | Desai et al. |
| 2018/0289620 A1 | 10/2018 | Desai et al. |
| 2018/0374583 A1 | 12/2018 | Goldstein |
| 2019/0022020 A1 | 1/2019 | Desai |
| 2019/0054033 A1 | 2/2019 | Foss |
| 2019/0147986 A1 | 5/2019 | Luo |
| 2019/0167629 A1 | 6/2019 | Desai |
| 2019/0175564 A1 | 6/2019 | Desai |
| 2019/0183789 A1 | 6/2019 | Seward |
| 2019/0184031 A1 | 6/2019 | Desai |
| 2019/0192477 A1 | 6/2019 | Desai |
| 2019/0247357 A1 | 8/2019 | Foss |
| 2019/0307732 A1 | 10/2019 | Desai |
| 2019/0343789 A1 | 11/2019 | Desai |
| 2020/0040398 A1 | 2/2020 | Desai |
| 2020/0129469 A1 | 4/2020 | Renschler |

(56) References Cited

U.S. PATENT DOCUMENTS

| | | |
|---|---|---|
| 2020/0138793 A1 | 5/2020 | Desai |
| 2020/0246275 A1 | 8/2020 | Pierce |
| 2020/0316216 A1 | 10/2020 | Desai |
| 2021/0000752 A1 | 1/2021 | Desai |
| 2021/0322335 A1 | 10/2021 | Desai et al. |
| 2022/0054404 A1 | 2/2022 | Desai et al. |
| 2023/0000844 A1 | 1/2023 | Desai et al. |
| 2023/0080409 A1 | 3/2023 | Desai |
| 2023/0190715 A1 | 6/2023 | Desai |
| 2023/0243806 A1 | 8/2023 | Peykov et al. |
| 2023/0293449 A1 | 9/2023 | Desai et al. |
| 2024/0009323 A1 | 1/2024 | Desai |
| 2024/0065984 A1 | 2/2024 | Desai |
| 2024/0082224 A1 | 3/2024 | Desai |

FOREIGN PATENT DOCUMENTS

| | | |
|---|---|---|
| CL | 201703456 A1 | 5/2018 |
| CN | 101730526 A | 6/2010 |
| CN | 104470949 A | 3/2015 |
| EP | 2481402 A2 | 8/2012 |
| EP | 2591775 A1 | 5/2013 |
| JP | 2010520289 A | 6/2010 |
| JP | 2012515213 A | 7/2012 |
| RU | 2483714 C2 | 6/2013 |
| WO | 199418954 A1 | 9/1994 |
| WO | 199814174 A1 | 4/1998 |
| WO | 199814175 A1 | 4/1998 |
| WO | 199900113 A1 | 1/1999 |
| WO | 200064437 A1 | 11/2000 |
| WO | 200071079 A2 | 11/2000 |
| WO | 200189522 A1 | 11/2001 |
| WO | 2002087545 A1 | 11/2002 |
| WO | 2003096944 A1 | 11/2003 |
| WO | 2004052401 A2 | 6/2004 |
| WO | 2004052401 A3 | 2/2005 |
| WO | 2006089290 A1 | 8/2006 |
| WO | 2007027819 A2 | 3/2007 |
| WO | 2007027941 A2 | 3/2007 |
| WO | 2007027819 A3 | 4/2007 |
| WO | 2007027941 A3 | 4/2007 |
| WO | 200071079 A3 | 3/2008 |
| WO | 2008027055 A1 | 3/2008 |
| WO | 2008057562 A1 | 5/2008 |
| WO | 2008076373 A1 | 6/2008 |
| WO | 2008109163 A1 | 9/2008 |
| WO | 2008137148 A2 | 11/2008 |
| WO | 2008150532 A1 | 12/2008 |
| WO | 2008137148 A3 | 2/2009 |
| WO | 2009126175 A1 | 10/2009 |
| WO | 2009126401 A1 | 10/2009 |
| WO | 2009126938 A1 | 10/2009 |
| WO | 2010068925 A1 | 6/2010 |
| WO | 2010083298 A1 | 7/2010 |
| WO | 2010105172 A1 | 9/2010 |
| WO | 2010118365 A1 | 10/2010 |
| WO | 2010121000 A1 | 10/2010 |
| WO | 2011025838 A1 | 3/2011 |
| WO | 2011119988 A1 | 9/2011 |
| WO | 2011123393 A1 | 10/2011 |
| WO | 2011123395 A1 | 10/2011 |
| WO | 2011153009 A1 | 12/2011 |
| WO | 2011153010 A1 | 12/2011 |
| WO | 2011156119 A1 | 12/2011 |
| WO | 2012149451 A1 | 11/2012 |
| WO | 2013090634 A1 | 6/2013 |
| WO | 2014105644 A1 | 7/2014 |
| WO | 2014110345 A1 | 7/2014 |
| WO | 2014110408 A1 | 7/2014 |
| WO | 2014110443 A1 | 7/2014 |
| WO | 2014123612 A1 | 8/2014 |
| WO | 2014143613 A1 | 9/2014 |
| WO | 2014144405 A1 | 9/2014 |
| WO | 2014144451 A2 | 9/2014 |
| WO | 2014151853 A1 | 9/2014 |
| WO | 2014159171 A1 | 10/2014 |
| WO | 2014172429 A1 | 10/2014 |
| WO | 2015157120 A1 | 10/2015 |
| WO | 2016141365 A1 | 9/2016 |
| WO | 2017004249 A1 | 1/2017 |
| WO | 2017004264 A1 | 1/2017 |
| WO | 2017004266 A1 | 1/2017 |
| WO | 2017004267 A1 | 1/2017 |
| WO | 2017201189 A1 | 11/2017 |
| WO | 2018064405 A1 | 4/2018 |
| WO | 2018067943 A1 | 4/2018 |
| WO | 2018071399 A1 | 4/2018 |
| WO | 2019126223 A1 | 6/2019 |
| WO | 2019183146 A1 | 9/2019 |
| WO | 2019226685 A1 | 11/2019 |
| WO | 2020191053 A1 | 9/2020 |

OTHER PUBLICATIONS

Afinitor. (Oct. 2010). "Highlights of Prescribing Information, Afinitor," Novartis Pharmaceuticals Corporation 25 pages.

Algulnik, M. (Mar. 15, 2012, e-pub. Aug. 11, 2011). "New Developments in Mammalian Target of Rapamycin Inhibitors for the Treatment of Sarcoma," Cancer 118(6)1486-1497.

Altmayer, P. et al. (1995). "Propofol Binding to Human Blood Proteins," Arzneimittelforschung 45:1053-1056.

Armah, H.B. et al. (Jan. 1, 2007). "Malignant Perivascular Epithelioid Cell Tumor (PEComa) of the Uterus With Late Renal and Pulmonary Metastases: A Case Report with Review of the Literature," Diagnostic Pathology 2(1) (45):1-7 pages.

Balkwill, F. (2006, e-pub. Sep. 2, 2006). "TNF-α In Promotion and Progression Of Cancer," Cancer Metastasis Rev. 25:409-416.

Barry, W. T. et al. (2005, e-pub. Jan. 10, 2005). "Significance Analysis of Functional Categories in Gene Expression Studies: A Structured Permutation Approach," Bioinformatics 21(9):1943-1949.

Benson, C. et al. (2014). "A Retrospective Study of Patients with Malignant PEComa Receiving Treatment with Sirolimus or Temsirolimus: The Royal Marsden Hospital Experience," Anticancer Research 34:3663-3668.

Berger, R. et al. (2008, e-pub. May 15, 2008). "Phase I Safety and Pharmacokinetic Study of CT-011, A Humanized Antibody Interacting With PD-1, in Patients With Advanced Hematologic Malignancies," Cancer Therapy: Clinical 14 (10):3044-3051.

Besztercei, B. et al. (Jul. 1, 2018). "Abstract No. 196: The Effect of Modulated Electro-Hyperthermia on B16-F10 Melanoma Tumor Growth," Cancer Research; AACR Annual Meeting 2018, American Association For Cancer Research, US; Chicago, IL, USA 78(13)1-4.

Bissler, J.J. et al. (Jan. 10, 2008). "Sirolimus for Angiomyolipoma in Tuberous Sclerosis Complex or Lymphangioleiomyomatosis," N. Engl. J. Med. 358(2):140-151, 20 pages.

Boehm, B.E. et al. (2015). "Novel Therapeutic Approaches for Recurrent Nonmuscle Invasive Bladder Cancer," Urol. Clin. N. Am. 42:159-168.

Bryan, L.J. et al. (2015). "Blocking Tumor Escape in Hematologic Malignancies: the Anti-PD-1 Strategy," Blood Review 29:25-32.

Bussemaker, H.J. et al. (Sep. 27, 2007). "Dissecting Complex Transcriptional Responses Using Pathway-Level Scores Based on Prior Information," BMC Bioinformatics 8(Suppl 6)(S6):1-7.

Carter, D.C. et al. (1994). "Structure of Serum Albumin," Adv. Protein. Chem. 45:153-203.

Celgen, KK. (Nov. 25, 2010). "New Drug Outlook, "Immunomodulator" for Multiple Myeloma," Medicament News 2034:12, two pages. (English Translation).

Chua-Alcala, V.S. et al. (Mar. 10, 2019, e-pub. Jul. 11, 2019). "Initial Results of a Phase III Investigation of Safety/Efficacy of Nivolumab and ABI-009 (Nab-Sirolimus) in Advanced Undifferentiated Pleomorphic Sarcoma (UPS), Liposarcoma (LPS), Chondrosarcoma (CS), Osteosarcoma (OS), and Ewing Sarcoma," Journal of Clinical Oncology 37(8):21-21, 2 pages.

Cirstea, D. et al. (Apr. 1, 2010). "Dual Inhibition of Akt/Manmalian Target of Rapamycin Pathway by Nanoparticle Albumin-Bound-

(56) References Cited

OTHER PUBLICATIONS

Rapamycin and Perifosine Induces Antitumor Activity in Multiple Myeloma," Molecular Cancer Therapeutics 9(4):963-975.
Curry, S. et al. (Nov. 23, 1999). "Fatty Acid Binding To Human Serum Albumin: New Insights From Crystallographic Studies," Biochim. Biophys. Acta. 1441(2-3):131-140.
Curry, S. et al. (Sep. 1998). "Crystal Structure of Human Serum Albumin Complexed With Fatty Acid Reveals An Asymmetric Distribution Of Binding Sites," Nat. Struct. Biol. 5(9):827-835.
De Biasi, A.R. et al. (Nov. 1, 2014, e-pub. Sep. 9, 2014). "Cisplatin-Induced Antitumor Immunomodulation: A Review of Preclinical and Clinical Evidence," Clin. Cancer Res. 20(21):5384-5391.
Desai, N. et al. (Dec. 2009). "Combination Regimens of nab-Rapamycin (ABI-009) Effective Against MDA-MB-231 Breast-Tumor Xenografts", Cancer Research; 32 Annual CTRC-AACR San Antonio Breast Cancer Symposium, Dec. 10-13, 2009; San Antonio, TX, 69(Suppl. 24): Abstract No. 6106, 3 pages.
Dickson, M.A. et al. (Apr. 1, 2013). "Extrarenal Perivascular Epithelioid Cell Tumors (PEComas) Respond to mTOR Inhibition: Clinical and Molecular Correlates," International Journal of Cancer 132(7):1711-1717.
Diken M. et al. (Dec. 2013, e-pub. Sep. 20, 2013). "mTOR Inhibition Improves Antitumor Effects of Vaccination with Antigen-Encoding RNA," Cancer Immunology Research 1(6):386-392.
Dong, H.L. et al. (Jul. 18, 2013). "Histone Deacetylase Inhibitor Potentiated the Ability Of MTOR Inhibitor to Induce Autophagic Cell Death in Burkitt Leukemia/Lymphoma," Journal Of Hematology & Oncology 6(1)(53):1-11.
El-Hashemite, N. et al. (2003). "Mutation inTsC2and Activation of Mammalian Target of Rapamycin Signalling Pathway in Renal Angiomyolipoma," Lancet 361(9366):1348-1349.
Emens, L.A. (Dec. 2012). "Breast Cancer Immunobiology Driving Immunotherapy: Vaccines and Immune Checkpoint Blockade," Expert Rev. Anticancer Ther. 12(12):1597-1611.
European Extended Search Report, mailed on Jan. 16, 2019, for European Patent Application No. 16818717.7, filed on Jan. 4, 2018, 13 pages.
Fang, Y. et al. (Nov. 30, 2001). "Phosphatidic Acid-Mediated Mitogenic Activation of mTOR Signaling," Science 294(5548):1942-1945.
Fehske, K.J. et al. (1981). "The Location of Drug Binding Sites in Human Serum Albumin," Biochem. Pharmcol. 30(7):687-692.
Finlayson, J.S. (1980). "Albumin Products," Seminars in Thrombosis and Hemostasis 6(2):85-120.
Gardner, E.R. (Jul. 1, 2008). "Randomized Crossover Pharmacokinetic Study of Solvent-Based Paclitaxel and nab-Paclitaxel," Clin. Cancer Res. 14(13):4200-4205.
Gardner, E.R. et al. (Feb. 1, 2008). "Quantitative Determination of Total and Unbound Paclitaxel in Human Plasma Following Abraxane Treatment," Journal of Chromatography B Analyst Technol. Biomed. Life Sci. 862(1-2):213-218, 11 pages.
Garrido, M.J. et al. (Nov.-Dec. 1994). "Characterization of Propofol Binding to Plasma Proteins and Possible Interaction," Rev. Esp. Anestestiol. Reanim. 41(6):308-312. (English Translation of Abstract Only.).
Gennatas, C. et al. (Sep. 3, 2012)."Successful Treatment With the mTOR Inhibitor Everolimus in a Patient With Perivascular Epithelioid Cell Tumor," World J. Surg. Oncol. 10(181):1-4.
Gonzalez-Angulo, A.M. et al. (Oct. 1, 2013). "Weekly nab-Rapamycin in Patients With Advanced Nonhematologic Malignancies: Final Results of a Phase I Trial," Clinical Cancer Research 19(19):5474-5484.
Guba, M. et al. (2005). "Dosing of Rapamycin is Critical to Achieve an Optima Antiangiogenic Effect Against Cancer," Transplant International 18:89-94.
Guba, M. et al. (Feb. 2002). "Rapamycin Inhibits Primary And Metastatic Tumor Growth By Antiangiogenesis: Involvement Of Vascular Endothelial Growth Factor," Nature Medicine 8(20):128-135.

Hauser, C.J. et al. (Jun. 1980). "Oxygen Transport Responses to Colloids and Cystalloids in Critically Ill Surgical Patients," Surgery, Gynecology and Obstetrics 150(6):811-816.
He, X.M. et al. (Jul. 16, 1992). "Atomic Structure and Chemistry of Human Serum Albumin," Nature 358:209-215.
Highfill, S.L. et al. (May 21, 2014). "Disruption of CXCR2-Mediated MDSC Tumor Trafficking Enhances Anti-PD1 Efficacy," Sci. Transl. Med. 6(327): 237ra67, 15 pages.
Hornick, J.L. et al. (2006). "PEComa: What Do We Know so Far?," Histopathology 48(1):75-82.
Hou, S. et al. (Jul. 2018). "Antitumor Activity of ABI-009 (nab-rapacmycin) in Combination With Anti-PD1 Antibody in a Syngeneic Mouse Model of B16 Melanoma," Cancer Research 78(13):Abstract No. 3856, 2 pages.
Huang, Z.Q. et al. (2011). "Molecular Targeted Approaches for Treatment of Pancreatic Cancer," Curr. Pharm Des. 17(21):2221-2238, 36 pages.
Inoki, K.et al. (Sep. 2002). "TSC2 is Phosphorylated and Inhibited by Akt and Supresses mTOR Signaling," Nature Cell Biology 4:648-657.
International Preliminary Report issued on Jan. 2, 2018, for PCT Application No. PCT/US16/40170, filed on Jun. 29, 2016, 5 pages.
International Search Report mailed on Sep. 22, 2016, for PCT Application No. PCT/US16/40170, filed on Jun. 29, 2016, 4 pages.
Italiano, A. et al. (May 2010, e-pub. Mar. 9, 2010). "Treatment With the mTOR Inhibitor Temsirolimus in Patients With Malignant PEComa," Annals of Oncology 21(5):1135-1137.
Iwao, Y. (2016). "Albumin Nanoparticles," Chapter 5 in Albumin in Medicine: Pathological and Clinical Applications, Otagiri, M. et al. Springer, pp. 91-119.
Jacinto, E. et al. (Nov. 2004, e-pub. Oct. 3, 2004). "Mammalian TOR Complex 2 Controls the Actin Cytoskeleton and is Rapamycin Insensitive," Nat. Cell Biol. 6(11):1122-1128, Supplementary Information pp. 1-3, total 10 pages.
Janku, F et al. (Jan. 30, 2014). PIK3CA, and PTEN Aberrations in Early-Phase Trials with PI3K/AKT/mTOR Inhibitors: Experience with 1,656 Patients at MD Anderson Cancer Center. Cell Reports 6(2):377-387, 27 pages.
Khaja, F. et al. (2013). "PEComa: A Perivascular Epithelioid Cell Tumor in the Liver—A Case Report and Review of the Literature," Case Reports in Medicine pp. 1-4.
Kim, D-H. et al. (Jul. 26, 2002). "mTOR Interacts with Raptor to Form a Nutrient-Sensitive Complex that Signals to the Cell Growth Machinery," Cell 110:163-175.
Knight, Z.A. et al. (May 19, 2006). "A Pharmacological Map of the PI3-K Family Defines a Role for p110a in Insulin Signaling," Cell 125:733-747.
Koenig, A.M. et al. (Feb. 16, 2009). "Perivascular Epitheloid Cell Tumour (PEComa) of the Retroperitoneum—A Rare Tumor With Uncertain Malignant Behaviour: A Case Report," J. Med. Case Reports 3(62):1-5.
Kragh-Hansen, U. (Feb. 1990). "Structure and Ligand Binding Properties of Human Serum Albumin," Dan. Med. Bull. 37(1):57-84.
Lao, I.W. et al. (May 29, 2015). "Malignant Perivascular Epithelioid Cell Tumor (PEComa) of the Femur: a Case Report and Literature Review," Diagnostic Pathology 10(54):1-6.
Lin, F. et al. (2013). "Dual mTORC1 and mTORC2 Inhibitor Palomid 529 Penetrates the Blood-brain Barrier Without Restriction by ABCB1 and ABCG2," In J. Cancer 133(5):1222-1234.
Maglietta, R. et al. (2007). "Statistical Assessment of Functional Categories of Genes Deregulated in Pathological Conditions by Using Microarray Data," Bioinformatics 23:2063-2072.
Mai, K.T. et al. (Oct. 2006). "Perivascular Epithelioid Cell Tumour (PEComa) of the Soft Tissue," Pathology 38(5):415-420.
Malouf, G.G. et al. (2010, e-pub. Feb. 12, 2010). "Targeted Agents in Metastatic Xp11 Translocation/TFE3 Gene Fusion Renal Cell Carcinoma (RRC): A Report From the Juvenile RCC Network," Annals of Oncology 21(9):1834-1838.
Martignoni, G. et al. (2008, e-pub. Dec. 14, 2007). "PEComas: the past, the present and the future," Virchows Arch. 452:119-132.

(56) References Cited

OTHER PUBLICATIONS

Momtaz, P. et al. (Nov. 15, 2014). "Immunologic Checkpoints in Cancer Therapy: Focus on the Programmed Death-1 (PD-1) Receptor Pathway," Pharmacogenomics and Personalized Medicine 7:357-365.

Myeloma Beacon Staff. (Feb. 8, 2013). "Pomalyst (Pomalidomide) Approved By FDA For Relapsed and Refractory Multiple Myeloma," located at https://myelomabeacon.org/news/2013/02/08/pomalyst-pomalidomide-fda-approval-multiple-myeloma/, last visited on Aug. 7, 2018, 8 pages.

Müller, B.G. et al. (1996). "Albumin Nanospheres As Carriers For Passive Drug Targeting: An Optimized Manufacturing Technique," Pharmaceutical Research 13(1):32-37.

NCCN. (Feb. 1, 2011). "Version 1.2011. NCCN Clinical Practice Guidelines in Oncology (NCCN Guidelines®). Soft Tissue Sarcoma," Version 1.2011, NCCN National Comprehensive Cancer Network 82 pages.

Novak, B.A. et al. (2006, e-pub. Nov. 8, 2005). Pathway Recognition and Augmentation by Computational Analysis of Microarray Expression Data, Bioinformatics 22(2):233-241.

Parfitt, J.R. et al. (Aug. 22, 2006). "Primary PEComa of the Bladder Treated With Primary Excision and Adjuvant Interferon-Alpha Immunotherapy: A Case Report," 6(20):1-4.

Paál, K. et al. (2001). "High Affinity Binding of Paclitaxel to Human Serum Albumin," Eur. J. Biochem. 268(7):2187-2191.

Powell, J.D. et al. (1999). "Inhibition of Cell Cycle Progression by Rapamycin Induces T Cell Clonal Anergy Even in the Presence of Costimulation," The Journal of Immunology 162:2775-2784.

Purcell, M. et al. (2000). "Interaction of Taxol With Human Serum Albumin," Biochim. Biophys. Acta. 1478:61-68.

Raje, N. et al. (Dec. 15, 2004, e-pub. Aug. 19, 2004). "Combination of the mTOR Inhibitor Rapamycin and (CC-5013) has Synergistic Activity in Multiple Myeloma," Blood 104(13):4188-4193.

Raje, N. et al. (Nov. 1, 2004). "Combination of the mTOR Inhibitor Rapamycin and Revlimid (TM) (CC-5013) has Synergistic Activity in Multiple Myeloma (MM)," Blood 104(11)(Part1):417A, 33 pages.

Ramakrishnan, V. et al. (Nov. 2014, e-pub. Sep. 2014). "Multiple Mechanisms Contribute to the Synergistic Anti-Myeloma Activity of the Pan-histone Deacetylase Inhibitor LBH589 and the Rapalog RAD001," Leukemia Research, 38(11):1358-1366, eighteen pages.

Rapamune. (Jul. 2011). "Highlights of Prescribing Information, Rapamune," Pfizer Wyeth Pharmaceutical, Inc. 56 pages.

Ritter, J. et al. (Oct. 2010). "Osteosarcoma," Ann. Oncol. 21(Supplement 7):vi320-vii325.

Roeven, M.W.H. et al. (Apr. 2014). "Immunotherapeutic Approaches to Treat Multiple Myeloma," Human Vaccines & Immunotherapeutics 10(4):896-910.

Roper, J. et al. (Sep. 26, 2011). "The Dual PI3K/mTOR Inhibitor NVP-BEZ235 Induces Tumor Regression in a Genetically Engineered Mouse Model of PIK3CA Wild-Type Colorectal Cancer," PLoS One 6(9):e25132.

Rozengurt, E. et al. (Nov. 2014). "Suppression of Feedback Loops Mediated by PI3K/mTOR Induces Multiple Over-Activation of Compensatory Pathways: An Unintended Consequence Lading to Drug Resistance," Mol. Cancer Ther. 13(11):2477-2488, 21 pages.

Rychak, E. et al. (Nov. 15, 2013). "The Novel mTOR Kinase Inhibitor CC-223 Demonstrates Significant Activity In In Vitro Models Of Multiple Myeloma (MM), Both As a Single Agent and In Combination With The Approved Agents, Dexamethasone, Lenalidomide and Pomalidomide," Blood 122(21):3160, 5 pages.

Sarbassov, D.D. et al. (Jul. 27, 2004). "Rictor, a Novel Binding Partner of mTOR, Defines a Rapamycin-Insensitive and Raptor-Independent Pathway that Regulates the Cytoskeleton," Current Biology 14:1296-1302.

Segal, E. et al. (Jun. 2003). "Module Networks: Identifying Regulatory Modules and Their Condition-Specific Regulators From Gene Expression Data," Nat. Genet. 34(2):166-176.

Segal, E. et al. (Oct. 2004, e-pub. Sep. 26, 2004) "A Module Map Showing Conditional Activity Of Expression Modules In Cancer," Nat. Genet. 36(10):1090-1098.

Segler, A. et al. (2012, e-pub. May 15, 2012). "Lenalidomide in Solid Tumors," Cancer Chemother. Pharmacol. 69:1393-1406.

Selvaggi, F. et al. (2011). "Malignant PEComa: A Case Report With Emphasis On Clinical And Morphological Criteria," BMC Surg. 11(3):1-5.

Sengupta, S. et al. (Oct. 22, 2010). "Regulation of the mTOR Complex 1 Pathway by Nutrients, Growth Factors, and Stress," Molecular Cell 40:310-322.

Sugio, S. et al. (1999). "Crystal Structure of Human Serum Albumin at 2.5 Å Resolution," Protein. Eng. 12(6):439-446.

Terpos, E. et al.(2013, e-pub. May 10, 2013). "Pomalidomide: A Novel Drug to Treat Relapsed and Refractory Multiple Myeloma," Onco Targets Ther. 6:531-538.

Tian, L. et al. (Sep. 20, 2005). "Discovering Statistically Significant Pathways in Expression Profiling Studies," Proc Nat'l Acad Sci USA 102:13544-13549.

Trieu, V. et al. (Dec. 2007). "mTOR Inhibitor Nanoparticle Albumin-Bound (nab) Rapamycin Is Effective In A Breast Cancer Xenograft Model," Abstracts—Poster Session VI, p. S268, Abstract No. 6063, 1 page.

Tullis, J.L. (Jan. 24, 1977). "Albumin. 1. Background and Use," JAMA 237(4): 355-360.

Tullis, J.L. (Jan. 31, 1977). "Albumin. 2. Guidelines for Clinical Use," JAMA 237(5):460-463.

Urien, S. et al. (May 1996). "Docetaxel Serum Protein Binding With High Affinity to Apha-Acid Glycoprotein," Invest. New Drugs 147:147-151.

Valerlote, F. et al. (Sep./Oct. 1975). "Synergistic Interaction of Anticancer Agents: A Cellular Perspective," Cancer Chemotherapy Reports Part 1 59(5):895-900.

Vörum, H. (Nov. 1999). "Reversible Ligand Binding to Human Serum Albumin," Dan. Med. Bull. 46(5):379-399.

Wagle, N. et al. (2012). "High-Throughout Detection of Actionable Genomic Alterations in Clinical Tumor Samples by Targeted, Massively Parallel Sequencing," Cancer discovery 2.1:82-93, 21 pages.

Wagner, A.J. et al. (2019). "ABI-009 (nab-sirolimus) in Advanced Malignant Perivascular Epithelioid Cell Tumors (PEComa): Preliminary Efficacy, Safety, and Mutational Status From AMPECT, an Open Label Phase II Registration Trial," ASCO Annual Meeting 2019, Abstract No. 11005, 2 pages.

Wagner, A.J. et al. (2020). "Abstract #11516: Long-Term Follow-up for Duration of Response (DOR) After Weekly Nab-Sirolimus (ABI-009) in Patients with Advanced Malignant Perivascular Epithelioid Cell Tumors (PEComa): Results From a Registrational Open-Label Phase 2 Trial, AMPECT," ASCO Virtual Scientific Program 2020, 1 page.

Wagner, A.J. et al. (2020). "Long-Term Follow-Up Duration of Response (DoR) After Weekly Nab-Sirolimus in Patients With Advanced Malignant Perivascular Epitheliod Cell Tumors (PEComa): Results From A Registrational Open-Label Phase II Trial, AMPECT," American Society of Clinical Oncology, 2 pages.

Wagner, A.J. et al. (Feb. 10, 2010). "Clinical Activity of mTOR Inhibition With Sirolimus in Malignant Perivascular Epithelioid Cell Tumors: Targeting the Pathogenic Activation of mTORC1 in Tumors," J. Clin. Oncol. 28(5):835-840.

Wang, C. et al. (Sep. 2014). "In Vitro Characterization of the Anti-PD-1 Antibody Nivolumab, BMS-936558, and In Vivo Toxicology in Non-Human Primates," Cancer Immunology Research 2(9):846-856.

Waters, P.S. et al. (2012, e-pub. Nov. 18, 2011). "Primary Malignant Gastric PEComa—Diagnostic and Technical Dilemmas," Int. J. Surg. Case Reports 3:89-91.

Wildgruber, M. et al. (2014). "Perivascular Epitheloid Cell Tumor (PEComa) Mimicking Retroperitoneal Liposarcoma," World J. Surg. Oncol. 12(3):1-4.

Written Opinion mailed on Sep. 22, 2016, for PCT Application No. PCT/US16/40170, filed on Jun. 29, 2016, 4 pages.

Yee, A.J. et al. (Apr. 25, 2014). "Outcomes in Patients With Relapsed or Refractory Multiple Myeloma in a Phase I Study of Everolimus in Combination With Lenalidomide," Br. J. Haematol. 166(3):401-409.

Younes, A. et al. (May 31, 2011). "Utility of mTOR Inhibition in Hematologic Malignancies," The Oncologist 16(6):730-741.

(56) References Cited

OTHER PUBLICATIONS

Anonymous. (2024). "mTOR Inhibitors," located at http://en.wipkedia.org/w/index.php?title=MTOR_inhibitors&oldid=1193655678, last visited on Feb. 12, 2024, 17 pages.

Barbarotta, L. et al. (Jan./Feb. 2015). "Romidepsin for the Treatment of Peripheral T-Cell Lymphoma," J. Adv. Pract. Oncol. 6(1):22-36.

Beagle, B.R. et al. (2015, e-pub. Dec. 12, 2014). "mTOR Kinase Inhibitors Synergize With Histone Deacetylase Inhibitors to Kill B-Cell Acture Lymphoblasticd Leukemia Cells," Oncotarget 6(4): 2088-2100.

Bleeker, J.S. et al. (2012). "Malignant" Perivascular Epithelioid Cell Neoplasm: Risk Stratification and Treatment Strategies, Hindawi Publishing Corporation Sarcoma, 2012:1-12.

Borrello, I.V. et al. (Mar./Apr. 2002). "Cancer Vaccines for Hematological Malignancies," Cancer Control 9 (2):138-151.

Clark, S.M. et al. (Jan.-Feb. 2014, e-pub. Jan. 1, 2014). "Pomalidomide for the Treatment of Multiple Myeloma," J. Adv. Prac. Oncol. 5(1):51-56, 7 pages.

Desai, M. et al. (Apr. 28, 2014). "Lenalidomide in Relapsed or Refractory Mantle Cell Lymphoma: Overview and Perspective," Ther. Adv. Hematol. 5(3):91-101.

European Extended Search Report, mailed on Apr. 5, 2022, for European Patent Application No. 21200495.6, filed on Oct. 1, 2021, 15 pages.

Fletcher, C.D.M. et al. (2013). "PEComa," Classification of Soft Tissue and Osteoma, published by the World Health Organization, 4th edition, published in 2013, copy in English, 6 pages.

Folpe, A.L. et al. (2010). "Perivascular Epithelioid Cell Neoplasms: Pathology and Pathogenesis," Human Pathology 41:1-15.

Gasper, W.J. et al. (Dec. 2013). "Adventitial Nab-Rapamycin Injection Reduces Porcine Femoral Artery Luminal Stenosis Induced by Balloon Angioplasty Via Inhibition of Medial Proliferation and Adventitial Inflammation," Circulation Cardiovasc Interv. 6:701-709.

McCormack, F.X. et al. (Feb. 2008). "Lymphangioleiomyomatosis* A Clinical Update," Chest 133(2):507-516.

Mineharu, Y. et al. (Dec. 2014, e-pub. Sep. 25, 2014). "Blockade of mTOR Signaling via Rapamycin Combined With Immunotherapy Augments Antiglioma Cytotoxic and Memory T-Cell Functions," Mol. Cancer Ther. 13(12):3024-3036.

Motzer, R.J. et al.. (May 1, 2015, e-pub. Dec. 1, 2014). "Nivolumab for Metastatic Renal Cell Carcinoma: Results of a Randomized Phase II Trial," Journal of Clinical Oncology 33(13):1430-1437.

Raje, N. et al. (Nov. 16, 2004). "Combination of mTOR Inhibitor Rapamycin and RevlimidTM (CC-5013) Has Synergistic Activity in Multiple Myeloma (MM)," Blood 104(11):1492, 2 pages.

Wang, Y. et al. (2011, e-pub. Feb. 1, 2011). "Temsirolimus, an mTOR Inhibitor, Enhances Anti-Tumour Effects of Heat Shock Protein Cancer Vaccines," Br. J. Cancer 104(4):643-652.

Adib, E. et al. (Jul. 15, 2021). "Phase II Clinical Trial of Everolimus in a Pan-Cancer Cohort of Patients with mTOR Pathway Alterations," Clinical Cancer Research 27(14):3845-3853.

Applicant filed Sep. 7, 2021, Comparative Clinical Data from an ABI-009 Expanded Access Program, 5 pages.

Communication Pursuant to Article 94(3) EPC for European Patent Application No. 21200495.6, mailed on Apr. 28, 2023, filed on Oct. 1, 2021, 10 pages.

Declaration of Neil P. Desai, Ph.D., Pursuant to 37 C.F.R. §, for U.S. Appl. No. 15/737,936, filed Jun. 29, 2016, Declaration signed on Nov. 27, 2019, submitted on Dec. 2, 2019, 5 pages.

European Summons to Attend Oral Proceedings Pursuant to Rule 115(1) EPC, mailed on Jul. 8, 2024, for European Patent Application No. 16818726.8, 10 pages.

Myers, A.P. (Oct. 1, 2013). "New Strategies in Endometrial Cancer: Targeting the PI3K/mTOR Pathway—The Devil Is in the Details," Clinical Cancer Research, 19(19):5264-5274.

METHODS OF TREATING EPITHELIOID CELL TUMORS

CROSS REFERENCE TO RELATED APPLICATIONS

This application is a continuation of U.S. patent application Ser. No. 15/737,936, which adopts the international filing date of Jun. 29, 2016, which is a National Phase application under 35 U.S.C. § 371 of International Application No. PCT/US2016/040170, filed on Jun. 29, 2016, which claims priority benefit of U.S. Provisional Application No. 62/186,252, filed Jun. 29, 2015, the contents of each are hereby incorporated herein by reference in their entirety.

TECHNICAL FIELD

The present invention relates to methods and compositions for the treatment of proliferative diseases belonging to the family of epithelioid cell tumors, such as perivascular epithelioid cell tumors (PEComas), by administering compositions comprising nanoparticles comprising an mTOR inhibitor, such as a limus drug, and an albumin.

BACKGROUND

Perivascular epithelioid cell tumors (PEComas) are a family of rare mesenchymal neoplasms composed of histologically and immunohistochemically distinctive epithelioid cells. The PEComa family of tumors include, for example, lymphangioleiomyomatosis (LAM), angiomyolipoma (AML), pulmonary clear cell 'sugar' tumors, and PEComa not otherwise specified (PEComa-NOS; a term referring to less well-characterized PEComas of a variety of other anatomical origins). PEComas share a distinctive cell type, namely, the perivascular epithelioid cell, and are often structured as nests and sheets, or occasionally spindled cells, with a focal association with blood vessel walls. See, Hornick, J. L. et al., *Histopathology*, 48:75-82 (2006); Wildgruber, M. et al., *World J Surg Oncol*, 12:1-4 (2014).

While most PEComas are benign, a subset of aggressive PEComas exhibit malignant behavior and develop, for example, locally invasive or distant metastases. See, Gennatas, C. et al., *World J Surg Oncol*, 10:1-4 (2012); Wagner, A. J. et al, *J Clin Oncol*, 28:835-840 (2010); Koenig, A. M et al., *J Med Case Reports*, 3: 1-5 (2009).

First-line treatment of PEComas is surgical resection. See, Martignoni, G. et al., *Virchows Arch*, 452:119-132 (2008). Treatment regimen with chemotherapy and/or radiotherapy remains controversial. The rarity of documented PEComas has prevented the use of designed therapeutic trials to investigate novel regimen for the treatment of PEComas. See, Selvaggi, F. et al., *BMC Surg*, 11 (2011); Waters, P. S. et al., *Int J Surg Case Reports*, 3:89-91 (2012). There is currently no second-line treatment for inoperable, aggressive, advanced, locally advanced, metastatic, or malignant PEComas. Accordingly, these subsets of PEComas remain very difficult to treat. The prognosis for patients within these patient subsets is poor, with a median survival estimated to be 12-17 months following diagnosis of advanced disease. Furthermore, for example, the 5-year survival rate of metastatic uterine PEComa is approximately 16%. See, Khaja, F. et al., *Case Reports in Medicine*, 2013:1-4 (2013).

The disclosures of all publications, patents, patent applications and published patent applications referred to herein are hereby incorporated herein by reference in their entirety.

BRIEF SUMMARY OF THE INVENTION

The present application in some embodiments provides a method of treating an epithelioid tumor in an individual, wherein the method comprises administering to the individual an effective amount of a composition comprising nanoparticles comprising an mTOR inhibitor and an albumin. In some embodiments, the epithelioid tumor is a perivascular epithelioid cell tumor (PEComa). In some embodiments, the PEComa is selected from the group consisting of a pulmonary clear cell 'sugar' tumor, a PEComa not otherwise specified (PEComa-NOS), angiomyolipoma, and lymphangioleiomyomatosis. In some embodiments, the epithelioid tumor is malignant. In some embodiments, the epithelioid tumor is locally advanced. In some embodiments, the epithelioid tumor is metastatic.

In some embodiments according to any of the methods described above, the mTOR inhibitor is a limus drug, such as sirolimus.

In some embodiments according to any of the methods described above, the effective amount of the mTOR inhibitor in the nanoparticle composition is about 10 mg/m$^2$ to about 100 mg/m$^2$ (including, for example, about 45-100 mg/m$^2$, about 75-100 mg/m$^2$, or about 45, 50, 75, or 100 mg/m$^2$). In some embodiments, the nanoparticle composition is administered weekly. In some embodiments, the nanoparticle composition is administered 2 out of every 3 weeks. In some embodiments, the nanoparticle composition is administered 3 out of 4 weeks. In some embodiments, the nanoparticle composition is administered on days 1 and 8 of a 21-day cycle. In some embodiments, the nanoparticle composition is administered on days 1, 8, and 15 of a 28-day cycle.

In some embodiments according to any of the methods described above, the nanoparticle composition is administered intravenously, intraarterially, intraperitoneally, intravesicularly, subcutaneously, intrathecally, intrapulmonarily, intramuscularly, intratracheally, intraocularly, transdermally, orally, intraportally, intrahepatically, hepatic arterial infusion, or by inhalation. In some embodiments, the nanoparticle composition is administered intravenously. In some embodiments, the nanoparticle composition is administered subcutaneously.

In some embodiments according to any of the methods described above, the nanoparticles in the composition have an average diameter of no greater than about 150 nm, such as no great than about 120 nm.

In some embodiments according to any of the methods described above, the mTOR inhibitor in the nanoparticles is associated (e.g., coated) with the albumin.

In some embodiments according to any of the methods described above, the individual is human.

In some embodiments according to any of the methods described above, the individual is selected for treatment based on a level (e.g., a high level) of a melanocytic marker (including, for example, HMB45, MelanA, and microphthalmia transcription factor) and a smooth muscle marker (including, for example, smooth muscle actin, pan-muscle actin, h-caldesmon, and calponin). In some embodiments, the level of the melanocytic marker and the smooth muscle marker is determined by immunohistochemistry.

In some embodiments according to any of the methods described above, the individual is selected for treatment based on the mutation status of a gene selected from the group consisting of TSC1, TSC2, TFE3, RHEB, MTOR, AKT, PIK3CA, and PTEN. In some embodiments, the individual is selected for treatment if the individual has a mutation in the gene, e.g., as determined by gene sequencing. In some embodiments, the gene sequencing is based on sequencing of a circulating or a cell-free DNA in a blood sample. In some embodiments, the gene sequencing is based on sequencing of DNA in a tumor sample.

In some embodiments according to any of the methods described above, the individual is selected for treatment based on the phosphorylation status of a protein selected from the group consisting of AKT, S6, S6K, and 4EBP1. In some embodiments, the individual is selected for treatment if the protein in the individual is phosphorylated. In some embodiments, the individual is selected for treatment if the protein in the individual is not phosphorylated. In some embodiments, the phosphorylation status of the protein is determined by immunohistochemistry.

In some embodiments according to any of the methods described above, the individual is selected for treatment based on a level of a proliferation marker or an apoptosis marker, such as, the proliferation marker, Ki-67, or the apoptosis marker, PARP or a fragment thereof. In some embodiments, the individual is selected for treatment based on the level of the proliferation marker and the apoptosis marker, e.g., as determined by immunohistochemistry.

In some embodiments according to any of the methods described above, the individual has not been previously treated with an mTOR inhibitor.

In some embodiments according to any of the methods described above, the individual has previously been treated with chemotherapy, radiation, or surgery.

These and other aspects and advantages of the present invention will become apparent from the subsequent detailed description and the appended claims. It is to be understood that one, some, or all of the properties of the various embodiments described herein may be combined to form other embodiments of the present invention.

DETAILED DESCRIPTION OF THE INVENTION

The present invention provides methods and compositions for treating epithelioid cell tumors, such as perivascular epithelioid cell tumors (PEComas), in an individual in need thereof comprising administering to the individual an effective amount of a composition comprising nanoparticles comprising an mTOR inhibitor (hereinafter also referred to as "mTOR nanoparticle composition") and an albumin. In some embodiments, the composition comprises a limus drug and an albumin (hereinafter also referred to as "limus nanoparticle composition").

In some embodiments, there is provided a method of treating a PEComa in an individual in need thereof, comprising administering to the individual an effective amount of a composition comprising nanoparticles comprising a limus drug and an albumin. In some embodiments, the limus drug is sirolimus. In some embodiments, the albumin is human albumin (such as human serum albumin). In some embodiments, the nanoparticles comprise sirolimus associated (e.g., coated) with albumin. In some embodiments, the average particle size of the nanoparticles in the nanoparticle composition is no more than about 150 nm (such as no greater than about 120 nm). In some embodiments, the composition comprises the albumin stabilized nanoparticle formulation of sirolimus. In some embodiments, the composition is Nab-sirolimus.

In some embodiments, there is provided a method of treating a PEComa in an individual, comprising administering to the individual an effective amount of a composition comprising nanoparticles comprising a limus drug and an albumin, wherein the limus drug is associated (e.g., coated) with the albumin. In some embodiments, there is provided a method of treating a PEComa in an individual, comprising administering to the individual an effective amount of a composition comprising nanoparticles comprising a limus drug and an albumin, wherein the average particle size of the nanoparticles in the nanoparticle composition is no greater than about 150 nm (such as less than about 120 nm). In some embodiments, there is provided a method of treating a PEComa in an individual, comprising administering to the individual an effective amount of a composition comprising nanoparticles comprising a limus drug and an albumin, wherein the limus drug is coated with the albumin, and wherein the average particle size of the nanoparticles in the nanoparticle composition is no greater than about 150 nm (such as no greater than about 120 nm). In some embodiments, there is provided a method of treating a PEComa in an individual, comprising administering to the individual an effective amount of a composition comprising Nab-sirolimus. In some embodiments, there is provided a method of treating a PEComa in an individual, comprising administering to the individual an effective amount of Nab-sirolimus.

In some embodiments, the composition is administered intravenously. In some embodiments, the composition is administered intraportally. In some embodiments, the composition is administered intraarterially. In some embodiments, the composition is administered intraperitoneally. In some embodiments, the composition is administered intrahepatically. In some embodiments, the composition is administered by hepatic arterial infusion. In some embodiments, the composition is administered intravesicularly. In some embodiments, the composition is administered subcutaneously. In some embodiments, the composition is administered intrathecally. In some embodiments, the composition is administered intrapulmonarily. In some embodiments, the composition is administered intramuscularly. In some embodiments, the composition is administered intratracheally. In some embodiments, the composition is administered intraocularly. In some embodiments, the composition is administered transdermally. In some embodiments, the composition is administered orally. In some embodiments, the composition is administered by inhalation.

PEComas that can be treated with the methods described herein include, but are not limited to, lymphangioleiomyomatosis (LAM), angiomyolipoma (AML), pulmonary clear cell 'sugar' tumors, a PEComa not otherwise specified (PEComa-NOS), and malignant forms thereof. In some embodiments, the PEComa is any of early stage PEComa, non-metastatic PEComa, primary PEComa, advanced PEComa, locally advanced PEComa, metastatic PEComa, PEComa in remission, recurrent PEComa, PEComa in an adjuvant setting, or PEComa in a neoadjuvant setting. In some embodiments, the PEComa is resistant to the treatment with a non-nanoparticle formulation of a chemotherapeutic agent (such as non-nanoparticle formulation of a limus drug).

The methods described herein can be used for any one or more of the following purposes: alleviating one or more symptoms of a PEComa, delaying progression of a PEComa, shrinking tumor size in a PEComa patient, inhibiting tumor growth of a PEComa, prolonging overall survival, prolonging disease-free survival, prolonging time to disease progression for a PEComa, preventing or delaying a PEComa tumor metastasis, reducing a preexisting PEComa tumor metastasis, reducing incidence or burden of a preexisting PEComa tumor metastasis, and preventing recurrence of a PEComa.

Also provided are compositions (such as pharmaceutical compositions), medicine, kits, and unit dosages useful for the methods described herein.

Further provided are methods of treating PEComas according to any one of the methods described above, wherein the treatment is based on an expression or activity level or mutation status of one or more biomarkers. Biomarkers include, but are not limited to, mTOR pathway genes, including but not limited to PIK3CA, TSC1, TSC2, AKT, PTEN, MTOR, RHEB, and TFE3, phosphoproteins including, but not limited to, p-AKT, p-S6, p-S6K, p-4EBP1, and p-SPARC, proliferation markers including, but not limited to, Ki-67, and apoptosis markers including, but not limited to, PARP.

Definitions

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of a pathological consequence of a PEComa. The methods of the invention contemplate any one or more of these aspects of treatment.

The term "individual" refers to a mammal and includes, but is not limited to, human, bovine, horse, feline, canine, rodent, or primate. In some embodiments, the individual is human.

As used herein, an "at risk" individual is an individual who is at risk of developing a PEComa. An individual "at risk" may or may not have detectable disease, and may or may not have displayed detectable disease prior to the treatment methods described herein. "At risk" denotes that an individual has one or more so-called risk factors, which are measurable parameters that correlate with development of a PEComa, which are described herein. An individual having one or more of these risk factors has a higher probability of developing cancer than an individual without these risk factor(s).

"Adjuvant setting" refers to a clinical setting in which an individual has had a history of a PEComa, and generally (but not necessarily) been responsive to therapy, which includes, but is not limited to, surgery (e.g., surgical resection), radiotherapy, and chemotherapy. However, because of their history of a PEComa, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "delaying" the development of a PEComa means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of a PEComa is a method that reduces probability of disease development in a given time frame and/or reduces the extent of the disease in a given time frame, when compared to not using the method. Such comparisons are typically based on clinical studies, using a statistically significant number of subjects. PEComa development can be detectable using standard methods, including, but not limited to, computerized axial tomography (CAT Scan), Magnetic Resonance Imaging (MRI), abdominal ultrasound, clotting tests, arteriography, or biopsy. Development may also refer to PEComa progression that may be initially undetectable and includes occurrence, recurrence, and onset.

The term "effective amount" used herein refers to an amount of a compound or composition sufficient to treat a specified disorder, condition or disease such as ameliorate, palliate, lessen, and/or delay one or more of its symptoms. In reference to a PEComa, an effective amount comprises an amount sufficient to cause a tumor to shrink and/or to decrease the growth rate of the tumor (such as to suppress tumor growth) or to prevent or delay other unwanted cell proliferation in a PEComa. In some embodiments, an effective amount is an amount sufficient to delay development of a PEComa. In some embodiments, an effective amount is an amount sufficient to prevent or delay recurrence. An effective amount can be administered in one or more administrations. In the case of PEComas, the effective amount of the drug or composition may: (i) reduce the number of epithelioid cells; (ii) reduce tumor size; (iii) inhibit, retard, slow to some extent and preferably stop a PEComa cancer cell infiltration into peripheral organs; (iv) inhibit (e.g., slow to some extent and preferably stop) tumor metastasis; (v) inhibit tumor growth; (vi) prevent or delay occurrence and/or recurrence of tumor; and/or (vii) relieve to some extent one or more of the symptoms associated with a PEComa.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein, the term "Nab" stands for nanoparticle albumin-bound. For example, Nab-sirolimus is a nanoparticle albumin-bound formulation of sirolimus. Nab-sirolimus is also known as Nab-rapamycin, which has been previously described, for example, see, WO2008109163A1, WO2014151853, WO2008137148A2, and WO2012149451A1.

As used herein, the term "mutation status" refers to the status of a gene sequence (e.g., containing a mutation) relative to a wildtype or reference gene sequence.

It is understood that aspects and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

Methods of Treating PEComas

The present invention provides methods of treating a PEComa in an individual (such as human) comprising administering to the individual an effective amount of a composition comprising nanoparticles comprising an mTOR inhibitor (such as a limus drug) and an albumin. In some embodiments, the invention provides methods of treating a PEComa in an individual (e.g., human) comprising administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is associated (e.g., coated) with the albumin. In some embodiments, the method comprises administering to the individual an effective amount of a composition comprising nanoparticles comprising a limus drug and an albumin, wherein the nanoparticles have an average particle size of no greater than about 150 nm (such as no greater than about 120 nm). In some embodiments, the average or mean diameter of the nanoparticles is about 10 nm to about 150 nm. In some embodiments, the average or mean diameter of the nanoparticles is about 40 nm to about 120 nm. In some embodiments, the method comprises administering to the individual an effective amount of a composition comprising nanoparticles comprising a limus drug and an albumin, wherein the nanoparticles comprise a limus drug associated (e.g., coated) with albumin, wherein the nanoparticles have an average particle size of no greater than about 150 nm (such as no greater than about 120 nm). In some embodiments, the method comprises administering to the individual an effective amount of a composition comprising nanoparticles comprising sirolimus and human albumin, wherein the nanoparticles comprise sirolimus associated (e.g., coated) with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

"mTOR inhibitor" used herein refers to inhibitors of mTOR. mTOR is a serine/threonine-specific protein kinase downstream of the phosphatidylinositol 3-kinase (PI3K)/Akt (protein kinase B) pathway, and a key regulator of cell survival, proliferation, stress, and metabolism. mTOR pathway dysregulation has been found in many human carcinomas, and mTOR inhibition produced substantial inhibitory effects on tumor progression. mTOR inhibitors described herein include, but are not limited to, BEZ235 (NVP-BEZ235), everolimus (also known as RAD001, Zortress, Certican, and Afinitor), rapamycin (also known as sirolimus or Rapamune), AZD8055, temsirolimus (also known as CCI-779 and Torisel), PI-103, Ku-0063794, INK 128, AZD2014, NVP-BGT226, PF-04691502, CH5132799, GDC-0980 (RG7422), Torin 1, WAY-600, WYE-125132, WYE-687, GSK2126458, PF-05212384 (PKI-587), PP-121, OSI-027, Palomid 529, PP242, XL765, GSK1059615, WYE-354, and eforolimus (also known as ridaforolimus or deforolimus).

In some embodiments, the mTOR inhibitor is a limus drug, which includes sirolimus and its analogues. Examples of limus drugs include, but are not limited to, temsirolimus (CCI-779), everolimus (RAD001), ridaforolimus (AP-23573), deforolimus (MK-8669), zotarolimus (ABT-578), pimecrolimus, and tacrolimus (FK-506). In some embodiments, the limus drug is selected from the group consisting of temsirolimus (CCI-779), everolimus (RAD001), ridaforolimus (AP-23573), deforolimus (MK-8669), zotarolimus (ABT-578), pimecrolimus, and tacrolimus (FK-506).

In some embodiments, the PEComa is lymphangioleiomyomatosis. In some embodiments, the PEComa is angiomyolipoma. In some embodiments, the PEComa is a pulmonary clear cell 'sugar' tumor. In some embodiments, the PEComa is an extrapulmonary clear cell 'sugar' tumor. In some embodiments, the PEComa is a PEComa-NOS. In some embodiments, the PEComa is malignant.

In some embodiments, the PEComa is: early stage PEComa, non-metastatic PEComa, non-invasive PEComa, invasive PEComa, primary PEComa, advanced PEComa, locally advanced PEComa, metastatic PEComa, recurrent PEComa, or PEComa in remission. In some embodiments, the PEComa has been refractory to prior therapy. In some embodiments, the PEComa is resistant to the treatment with a non-nanoparticle formulation of a chemotherapeutic agent (such as non-nanoparticle formulation of an mTOR inhibitor, such as a limus drug).

In some embodiments, the PEComa is localized resectable (e.g., tumors that can be completely surgically removal), localized unresectable (e.g., the localized tumors may be unresectable because crucial blood vessel structures are involved), or unresectable (e.g., tumor characteristics or patient conditions preventing surgical removal).

In some embodiments, the PEComa is located in or closely associated with a kidney, bladder, prostate, uterus, ovary, vulva, vagina, lung, pancreas, liver, lymph node, and/or skin.

In some embodiments, the PEComa is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm), a stage IV tumor (tumors with direct invasion of adjacent organs other than the gallbladder, or perforation of visceral peritoneum), N1 tumor (regional lymph node metastasis), or M1 tumor (distant metastasis). In some embodiments, the PEComa is, according to AJCC (American Joint Commission on Cancer) staging criteria, stage T1, T2, T3, or T4 PEComa. In some embodiments, the individual is at a clinical stage of Ta, Tis, T1, T2, T3a, T3b, or T4. In some embodiments, the individual is at a clinical stage of Tis, CIS, Ta, or T1.

In some embodiments, the PEComa is characterized with immunohistochemically positive expression of a melanocytic marker and a smooth muscle marker. In some embodiments, the melanocytic marker is selected from the group consisting of HMB45, MelanA, and microphthalmia transcription factor. In some embodiments, the smooth muscle marker is selected from the group consisting of smooth muscle actin, pan-muscle actin, h-caldesmon, and calponin. In some embodiments, the PEComa characterization is made on the primary tumor biopsy. In some embodiments, the PEComa characterization is made on the metastatic tumor biopsy. In some embodiments, the individual is diagnosed with a PEComa by characterization of a tumor with immunohistochemically positive expression of a melanocytic marker and a smooth muscle marker. In some embodiments, the melanocytic marker is selected from the group consisting of HMB45, MelanA, and microphthalmia transcription factor. In some embodiments, the smooth muscle marker is selected from the group consisting of smooth muscle actin, pan-muscle actin, h-caldesmon, and calponin. In some embodiments, the diagnosis is made on the primary tumor biopsy. In some embodiments, the diagnosis is made on the metastatic tumor biopsy.

In some embodiments, there is provided a method of treating a localized resectable PEComa in an individual (e.g., human), comprising administering to the individual an effective amount of a composition comprising nanoparticles comprising an mTOR inhibitor (such as a limus drug) and an albumin. In some embodiments, the invention provides methods of treating a localized resectable PEComa in an individual (e.g., human) comprising administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is associated (e.g., coated) with the albumin. In some embodiments, the method comprises administering to the individual an effective amount of a composition comprising nanoparticles comprising a limus drug and an albumin, wherein the nanoparticles have an average particle size of no greater than about 150 nm (such as no greater than about 120 nm). In some embodiments, the method comprises administering to the individual an effective amount of a composition comprising nanoparticles comprising a limus drug and an albumin, wherein the nanoparticles comprise a limus drug associated (e.g., coated) with albumin, wherein the nanoparticles have an average particle size of no greater than about 150 nm (such as no greater than about 120 nm). In some embodiments, the method comprises administering to the individual an effective amount of a composition comprising nanoparticles comprising sirolimus and human albumin, wherein the nanoparticles comprise sirolimus associated (e.g., coated) with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus. In some embodiments, the PEComa is resectable with multiple resections.

In some embodiments, there is provided a method of treating a localized unresectable PEComa in an individual (e.g., human), comprising administering to the individual an effective amount of a composition comprising nanoparticles comprising an mTOR inhibitor (such as a limus drug) and an albumin. In some embodiments, the invention provides methods of treating a localized unresectable PEComa in an individual (e.g., human) comprising administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is associated (e.g., coated) with the albumin. In some embodiments, the method comprises administering to the individual an effective amount of a composition comprising nanoparticles comprising a limus drug and an albumin, wherein the nanoparticles have an average particle size of no greater than about 150 nm (such as no greater than about 120 nm). In some embodiments, the method comprises administering to the individual an effective amount of a composition comprising nanoparticles comprising a limus drug and an albumin, wherein the nanoparticles comprise a limus drug associated (e.g., coated) with albumin, wherein the nanoparticles have an average particle size of no greater than about 150 nm (such as no greater than about 120 nm). In some embodiments, the method comprises administering to the individual an effective amount of a composition comprising nanoparticles comprising sirolimus and human albumin, wherein the nanoparticles comprise sirolimus associated (e.g., coated) with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

Thus, for example, in some embodiments, there is provided a method of treating an unresectable PEComa in an individual (e.g., human), comprising administering to the individual an effective amount of a composition comprising nanoparticles comprising an mTOR inhibitor (such as a limus drug) and an albumin. In some embodiments, the invention provides methods of treating an unresectable PEComa in an individual (e.g., human) comprising administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is associated (e.g., coated) with the albumin. In some embodiments, the method comprises administering to the individual an effective amount of a composition comprising nanoparticles comprising a limus drug and an albumin, wherein the nanoparticles have an average particle size of no greater than about 150 nm (such as no greater than about 120 nm). In some embodiments, the method comprises administering to the individual an effective amount of a composition comprising nanoparticles comprising a limus drug and an albumin, wherein the nanoparticles comprise a limus drug associated (e.g., coated) with albumin, wherein the nanoparticles have an average particle size of no greater than about 150 nm (such as no greater than about 120 nm). In some embodiments, the method comprises administering to the individual an effective amount of a composition comprising nanoparticles comprising sirolimus and human albumin, wherein the nanoparticles comprise sirolimus associated (e.g., coated) with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

Thus, for example, in some embodiments, there is provided a method of treating a malignant PEComa in an individual (e.g., human), comprising administering to the individual an effective amount of a composition comprising nanoparticles comprising an mTOR inhibitor (such as a limus drug) and an albumin. In some embodiments, the invention provides methods of treating a malignant PEComa in an individual (e.g., human) comprising administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is associated (e.g., coated) with the albumin. In some embodiments, the method comprises administering to the individual an effective amount of a composition comprising nanoparticles comprising a limus drug and an albumin, wherein the nanoparticles have an average particle size of no greater than about 150 nm (such as no greater than about 120 nm). In some embodiments, the method comprises administering to the individual an effective amount of a composition comprising nanoparticles comprising a limus drug and an albumin, wherein the nanoparticles comprise a limus drug associated (e.g., coated) with albumin, wherein the nanoparticles have an average particle size of no greater than about 150 nm (such as no greater than about 120 nm). In some embodiments, the method comprises administering to the individual an effective amount of a composition comprising nanoparticles comprising sirolimus and human albumin, wherein the nanoparticles comprise sirolimus associated (e.g., coated) with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

Thus, for example, in some embodiments, there is provided a method of treating a metastatic PEComa in an individual (e.g., human), comprising administering to the individual an effective amount of a composition comprising nanoparticles comprising an mTOR inhibitor (such as a limus drug) and an albumin. In some embodiments, the invention provides methods of treating a metastatic PEComa in an individual (e.g., human) comprising administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is associated (e.g., coated) with the albumin. In some embodiments, the method comprises administering to the individual an effective amount of a composition comprising nanoparticles comprising a limus drug and an albumin, wherein the nanoparticles have an average particle size of no greater than about 150 nm (such as no greater than about 120 nm). In some embodiments, the method comprises administering to the individual an effective amount of a composition comprising nanoparticles comprising a limus drug and an albumin, wherein the nanoparticles comprise a limus drug associated (e.g., coated) with albumin, wherein the nanoparticles have an average particle size of no greater than about 150 nm (such as no greater than about 120 nm). In some embodiments, the method comprises administering to the individual an effective amount of a composition comprising nanoparticles comprising sirolimus and human albumin, wherein the nanoparticles comprise sirolimus associated (e.g., coated) with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

Thus, for example, in some embodiments, there is provided a method of treating a recurrent PEComa in an individual (e.g., human), comprising administering to the individual an effective amount of a composition comprising nanoparticles comprising an mTOR inhibitor (such as a limus drug) and an albumin. In some embodiments, the invention provides methods of treating a recurrent PEComa in an individual (e.g., human) comprising administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is associated (e.g., coated) with the albumin. In some embodiments, the method comprises administering to the individual an effective amount of a composition comprising nanoparticles comprising a limus drug and an albumin, wherein the nanoparticles have an average particle size of no greater than about 150 nm (such as no greater than about 120 nm). In some embodiments, the method comprises administering to the individual an effective amount of a composition comprising nanoparticles comprising a limus drug and an albumin, wherein the nanoparticles comprise a limus drug associated (e.g., coated) with albumin, wherein the nanoparticles have an average particle size of no greater than about 150 nm (such as no greater than about 120 nm). In some embodiments, the method comprises administering to the individual an effective amount of a composition comprising nanoparticles comprising sirolimus and human albumin, wherein the nanoparticles comprise sirolimus associated (e.g., coated) with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

Thus, for example, in some embodiments, there is provided a method of treating a locally advanced PEComa in an individual (e.g., human), comprising administering to the individual an effective amount of a composition comprising nanoparticles comprising an mTOR inhibitor (such as a limus drug) and an albumin. In some embodiments, the invention provides methods of treating a locally advanced PEComa in an individual (e.g., human) comprising administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is associated (e.g., coated) with the albumin. In some embodiments, the method comprises administering to the individual an effective amount of a composition comprising nanoparticles comprising a limus drug and an albumin, wherein the nanoparticles have an average particle size of no greater than about 150 nm (such as no greater than about 120 nm). In some embodiments, the method comprises administering to the individual an effective amount of a composition comprising nanoparticles comprising a limus drug and an albumin, wherein the nanoparticles comprise a limus drug associated (e.g., coated) with albumin, wherein the nanoparticles have an average particle size of no greater than about 150 nm (such as no greater than about 120 nm). In some embodiments, the method comprises administering to the individual an effective amount of a composition comprising nanoparticles comprising sirolimus and human albumin, wherein the nanoparticles comprise sirolimus associated (e.g., coated) with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

Thus, for example, in some embodiments, there is provided a method of stabilizing PEComa (e.g., preventing or delaying the worsening of the disease) in an individual (e.g., human), comprising administering to the individual an effective amount of a composition comprising nanoparticles comprising an mTOR inhibitor (such as a limus drug) and an albumin. In some embodiments, the invention provides methods of stabilizing PEComa (e.g., preventing or delaying the worsening of the disease) in an individual (e.g., human) comprising administering to the individual an effective amount of a composition comprising nanoparticles comprising a limus drug and an albumin. In some embodiments, the method comprises administering to the individual an effective amount of a composition comprising nanoparticles comprising a limus drug and an albumin, wherein the limus drug in the nanoparticles is associated (e.g., coated) with the albumin. In some embodiments, the method comprises administering to the individual an effective amount of a composition comprising nanoparticles comprising a limus drug and an albumin, wherein the nanoparticles have an average particle size of no greater than about 150 nm (such as no greater than about 120 nm). In some embodiments, the method comprises administering to the individual an effective amount of a composition comprising nanoparticles comprising a limus drug and an albumin, wherein the nanoparticles comprise a limus drug associated (e.g., coated) with albumin, wherein the nanoparticles have an average particle size of no greater than about 150 nm (such as no greater than about 120 nm). In some embodiments, the method comprises administering to the individual an effective amount of a composition comprising nanoparticles comprising sirolimus and human albumin, wherein the nanoparticles comprise sirolimus associated (e.g., coated) with human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

The methods provided herein can be used to treat an individual (e.g., human) who has been diagnosed with or is suspected of having a PEComa. In some embodiments, the individual is human. In some embodiments, the individual is at least about any of 20, 25, 30, 35, 40, 45, 50, 55, 60, 65, 70, 75, 80, or 85 years old. In some embodiments, the individual is male. In some embodiments, the individual is female. In some embodiments, the individual has undergone a tumor resection. In some embodiments, the individual has refused surgery. In some embodiments, the individual is medically inoperable.

In some embodiments, the individual is a human who exhibits one or more symptoms associated with a PEComa. In some embodiments, the individual is at an early stage of a PEComa. In some embodiments, the individual is at an advanced stage of a PEComa. In some of embodiments, the individual is genetically or otherwise predisposed (e.g., having a risk factor) to developing a PEComa. Individuals at risk for PEComa include, e.g., those whose risk is determined by analysis of genetic or biochemical markers. These risk factors include, but are not limited to, age, sex, race, diet, history of previous disease, presence of precursor disease, genetic considerations (e.g., mutation status of tuberous sclerosis complex (TSC)), and environmental exposure. In some embodiments, the individuals at risk for PEComa include, e.g., those having relatives who have experienced PEComa, and those whose risk is determined by analysis of genetic or biochemical markers (e.g., expression and activity level or mutation status). Biomarkers include, but are not limited to, MTOR pathway genes, including but not limited to PIK3CA, TSC1, TSC2, AKT, PTEN, MTOR, RHEB, and TFE3, phosphoproteins including, but not limited to, p-AKT, p-S6, p-S6K, p-4EBP1, p-SPARC, proliferation markers including, but not limited to, Ki67, and apoptosis markers including, but not limited to, PARP or fragments thereof. In some embodiments, a blood sample or tumor biopsy from an individual is used to assess the biomarkers.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. In some embodiments, the individual has not previously been treated. In some embodiments, the method is used as a first line therapy. In some embodiments, the method is used as a second line therapy. In some embodiments, the individual has not been previously treated with an mTOR inhibitor. In some embodiments, the individual has not been previously treated with a limus drug.

In some embodiments, there is provided a method of prolonging time to disease progression of a PEComa in an individual, comprising administering to the individual an effective amount of a composition comprising nanoparticles comprising an mTOR inhibitor and an albumin. In some embodiments, the method prolongs the time to disease progression by at least any of 1, 2, 3, 4, 5, 6, 7, 8, 9, 10, 11, or 12 weeks. In some embodiments, the mTOR inhibitor is a limus drug. In some embodiments, the limus drug is sirolimus. In some embodiments, the composition comprises Nab-sirolimus. In some embodiments, the composition is Nab-sirolimus.

In some embodiments, there is provided a method of prolonging survival of an individual having a PEComa, comprising administering to the individual an effective amount of a composition comprising nanoparticles comprising an mTOR inhibitor and an albumin. In some embodiments, the method prolongs the survival of the individual by at least any of 1, 2, 3, 4, 5, 6, 7, 8, 9, 10, 11, 12, 18, or 24 month. In some embodiments, the mTOR inhibitor is a limus drug. In some embodiments, the limus drug is sirolimus. In some embodiments, the composition comprises Nab-sirolimus. In some embodiments, the composition is Nab-sirolimus.

In some embodiments, there is provided a method of alleviating one or more symptoms in an individual having a PEComa, comprising administering to the individual an effective amount of a composition comprising nanoparticles comprising an mTOR inhibitor and an albumin. In some embodiments, the mTOR inhibitor is a limus drug. In some embodiments, the limus drug is sirolimus. In some embodiments, the composition comprises Nab-sirolimus. In some embodiments, the composition is Nab-sirolimus.

In some embodiments, there is provided a method of improving the quality of life in an individual having a PEComa, comprising administering to the individual an effective amount of a composition comprising nanoparticles comprising an mTOR inhibitor and an albumin. In some embodiments, the mTOR inhibitor is a limus drug. In some embodiments, the limus drug is sirolimus. In some embodiments, the composition comprises Nab-sirolimus. In some embodiments, the composition is Nab-sirolimus.

In some embodiments, the individual has been previously treated for a PEComa (also referred to as the "prior therapy"). In some embodiments, the individual is resistant to treatment of PEComa with other agents (such as non-nanoparticle formulations of mTOR inhibitors). In some embodiments, the individual is initially responsive to treatment of PEComa with other agents but has progressed after treatment. Prior treatments include, but are not limited to, chemotherapy, radiation, and surgery. In some embodiments, the prior therapy has stopped for greater than or 28 days prior to initiation of the methods described herein. In some embodiments, the prior therapy has stopped for greater than 5 half-lives of the agents of the prior therapy prior to initiation of the methods described herein.

In some embodiments, the individual has recurrent a PEComa after a prior therapy. For example, the individual may be initially responsive to the treatment with the prior therapy, but develops PEComa after about any of about 2, 3, 4, 5, 6, 7, 8, 9, 10, 11, 12, 24, 36, 48, or 60 months upon the cessation of the prior therapy.

In some embodiments, the individual is refractory to a prior therapy.

In some embodiments, the individual has progressed on the prior therapy at the time of treatment. For example, the individual has progressed within any of about 1, 2, 3, 4, 5, 6, 7, 8, 9, 10, 11, or 12 months upon treatment with the prior therapy.

In some embodiments, the individual is resistant to the prior therapy.

In some embodiments, the individual is unsuitable to continue with the prior therapy, for example, due to failure to respond and/or due to toxicity.

In some embodiments, the individual is non-responsive to the prior therapy.

In some embodiments, the individual is partially responsive to the prior therapy or exhibits a less desirable degree of responsiveness.

In some embodiments, there is provided a method of treating lymphangioleiomyomatosis in an individual (e.g., human) comprising administering to the individual an effective amount of a composition comprising nanoparticles comprising an mTOR inhibitor (such as a limus drug) and an albumin. In some embodiments, there is provided a method of treating lymphangioleiomyomatosis in an individual (e.g., human) comprising administering to the individual an effective amount of a composition comprising nanoparticles comprising a limus drug and an albumin. In some embodiments, there is provided a method of treating lymphangioleiomyomatosis in an individual (e.g., human) comprising administering to the individual an effective amount of a composition comprising nanoparticles comprising a limus drug and an albumin, wherein the limus drug in the nanoparticles is associated (e.g., coated) with the albumin. In some embodiments, there is provided a method of treating lymphangioleiomyomatosis in an individual (e.g., human) comprising administering to the individual an effective amount of a composition comprising nanoparticles comprising a limus drug and an albumin, wherein the nanoparticles have an average particle size of no greater than about 150 nm (such as no greater than about 120 nm). In some embodiments, there is provided a method of treating lymphangioleiomyomatosis in an individual (e.g., human) comprising administering to the individual an effective amount of a composition comprising nanoparticles comprising a limus drug and an albumin, wherein the nanoparticles comprise a limus drug associated (e.g., coated) with albumin, and wherein the nanoparticles have an average particle size of no greater than about 150 nm (such as no greater than about 120 nm). In some embodiments, there is provided a method of treating lymphangioleiomyomatosis in an individual (e.g., human) comprising administering to the individual an effective amount of a composition comprising nanoparticles comprising sirolimus and human albumin, wherein the nanoparticles comprise sirolimus associated (e.g., coated) with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating lymphangioleiomyomatosis in an individual (e.g., human) comprising administering to the individual an effective amount of a composition comprising Nab-sirolimus. In some embodiments, there is provided a method of treating lymphangioleiomyomatosis in an individual (e.g., human) comprising administering to the individual an effective amount of Nab-sirolimus. In some embodiments, the mTOR inhibitor (such as a limus drug) is administered at a dose of about 10 mg/m$^2$ to about 150 mg/m$^2$, including, for example, about 45 mg/m$^2$ to about 100 mg/m$^2$ and about 75 mg/m$^2$ to about 100 mg/m$^2$. In some embodiments, the limus drug is administered at a dose of about 100 mg/m$^2$. In some embodiments, the limus drug is administered at a dose of about 75 mg/m$^2$. In some embodiments, the limus drug is administered at a dose of about 56 mg/m$^2$. In some embodiments, the limus nanoparticle composition is administered weekly. In some embodiments, the limus nanoparticle composition is administered two out of every three weeks (e.g., days 1 and 8 of a 21-day cycle). In some embodiments, the limus nanoparticle composition is administered three out of four weeks (e.g., days 1, 8, and 15 of a 28-day cycle). In some embodiments, the limus nanoparticle composition is administered by intravenous infusion over 30 minutes.

In some embodiments, there is provided a method of treating angiomyolipoma in an individual (e.g., human) comprising administering to the individual an effective amount of a composition comprising nanoparticles comprising an mTOR inhibitor (such as a limus drug) and an albumin. In some embodiments, there is provided a method of treating angiomyolipoma in an individual (e.g., human) comprising administering to the individual an effective amount of a composition comprising nanoparticles comprising a limus drug and an albumin. In some embodiments, there is provided a method of treating angiomyolipoma in an individual (e.g., human) comprising administering to the individual an effective amount of a composition comprising nanoparticles comprising a limus drug and an albumin, wherein the limus drug in the nanoparticles is associated (e.g., coated) with the albumin. In some embodiments, there is provided a method of treating angiomyolipoma in an individual (e.g., human) comprising administering to the individual an effective amount of a composition comprising nanoparticles comprising a limus drug and an albumin, wherein the nanoparticles have an average particle size of no greater than about 150 nm (such as no greater than about 120 nm). In some embodiments, there is provided a method of treating angiomyolipoma in an individual (e.g., human) comprising administering to the individual an effective amount of a composition comprising nanoparticles comprising a limus drug and an albumin, wherein the nanoparticles comprise a limus drug associated (e.g., coated) with albumin, and wherein the nanoparticles have an average particle size of no greater than about 150 nm (such as no greater than about 120 nm). In some embodiments, there is provided a method of treating angiomyolipoma in an individual (e.g., human) comprising administering to the individual an effective amount of a composition comprising nanoparticles comprising sirolimus and human albumin, wherein the nanoparticles comprise sirolimus associated (e.g., coated) with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating angiomyolipoma in an individual (e.g., human) comprising administering to the individual an effective amount of a composition comprising Nab-sirolimus. In some embodiments, there is provided a method of treating angiomyolipoma in an individual (e.g., human) comprising administering to the individual an effective amount of Nab-sirolimus. In some embodiments, the limus drug is administered at a dose of about 10 mg/m$^2$ to about 150 mg/m$^2$, including, for example, about 45 mg/m$^2$ to about 100 mg/m$^2$ and about 75 mg/m$^2$ to about 100 mg/m$^2$. In some embodiments, the limus drug is administered at a dose of about 100 mg/m$^2$. In some embodiments, the limus drug is administered at a dose of about 75 mg/m$^2$. In some embodiments, the limus drug is administered at a dose of about 56 mg/m$^2$. In some embodiments, the limus nanoparticle composition is administered weekly. In some embodiments, the limus nanoparticle composition is administered two out of every three weeks (e.g., days 1 and 8 of a 21-day cycle). In some embodiments, the limus nanoparticle composition is administered three out of four weeks (e.g., days 1, 8, and 15 of a 28-day cycle). In some embodiments, the limus nanoparticle composition is administered by intravenous infusion over 30 minutes.

In some embodiments, there is provided a method of treating pulmonary clear cell 'sugar' tumors in an individual (e.g., human) comprising administering to the individual an effective amount of a composition comprising nanoparticles comprising an mTOR inhibitor (such as a limus drug) and an albumin. In some embodiments, there is provided a method of treating pulmonary clear cell 'sugar' tumors in an individual (e.g., human) comprising administering to the individual an effective amount of a composition comprising nanoparticles comprising a limus drug and an albumin. In some embodiments, there is provided a method of treating pulmonary clear cell 'sugar' tumors in an individual (e.g., human) comprising administering to the individual an effective amount of a composition comprising nanoparticles comprising a limus drug and an albumin, wherein the limus drug in the nanoparticles is associated (e.g., coated) with the albumin. In some embodiments, there is provided a method of treating pulmonary clear cell 'sugar' tumors in an individual (e.g., human) comprising administering to the individual an effective amount of a composition comprising nanoparticles comprising a limus drug and an albumin, wherein the nanoparticles have an average particle size of no greater than about 150 nm (such as no greater than about 120 nm). In some embodiments, there is provided a method of treating pulmonary clear cell 'sugar' tumors in an individual (e.g., human) comprising administering to the individual an effective amount of a composition comprising nanoparticles comprising a limus drug and an albumin, wherein the nanoparticles comprise a limus drug associated (e.g., coated) with albumin, and wherein the nanoparticles have an average particle size of no greater than about 150 nm (such as no greater than about 120 nm). In some embodiments, there is provided a method of treating pulmonary clear cell 'sugar' tumors in an individual (e.g., human) comprising administering to the individual an effective amount of a composition comprising nanoparticles comprising sirolimus and human albumin, wherein the nanoparticles comprise sirolimus associated (e.g., coated) with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating pulmonary clear cell 'sugar' tumors in an individual (e.g., human) comprising administering to the individual an effective amount of a composition comprising Nab-sirolimus. In some embodiments, there is provided a method of treating a pulmonary clear cell 'sugar' tumors in an individual (e.g., human) comprising administering to the individual an effective amount of Nab-sirolimus. In some embodiments, the limus drug is administered at a dose of about 10 mg/m$^2$ to about 150 mg/m$^2$, including, for example, about 45 mg/m$^2$ to about 100 mg/m$^2$ and about 75 mg/m$^2$ to about 100 mg/m$^2$. In some embodiments, the limus drug is administered at a dose of about 100 mg/m$^2$. In some embodiments, the limus drug is administered at a dose of about 75 mg/m$^2$. In some embodiments, the limus drug is administered at a dose of about 56 mg/m$^2$. In some embodiments, the limus nanoparticle composition is administered weekly. In some embodiments, the limus nanoparticle composition is administered two out of every three weeks (e.g., days 1 and 8 of a 21-day cycle). In some embodiments, the limus nanoparticle composition is administered three out of four weeks (e.g., days 1, 8, and 15 of a 28-day cycle). In some embodiments, the limus nanoparticle composition is administered by intravenous infusion over 30 minutes.

In some embodiments, there is provided a method of treating PEComa-NOS in an individual (e.g., human) comprising administering to the individual an effective amount of a composition comprising nanoparticles comprising an mTOR inhibitor (such as a limus drug) and an albumin. In some embodiments, there is provided a method of treating PEComa-NOS in an individual (e.g., human) comprising administering to the individual an effective amount of a composition comprising nanoparticles comprising a limus drug and an albumin. In some embodiments, there is provided a method of treating PEComa-NOS in an individual (e.g., human) comprising administering to the individual an effective amount of a composition comprising nanoparticles comprising a limus drug and an albumin, wherein the limus drug in the nanoparticles is associated (e.g., coated) with the albumin. In some embodiments, there is provided a method of treating PEComa-NOS in an individual (e.g., human) comprising administering to the individual an effective amount of a composition comprising nanoparticles comprising a limus drug and an albumin, wherein the nanoparticles have an average particle size of no greater than about 150 nm (such as no greater than about 120 nm). In some embodiments, there is provided a method of treating PEComa-NOS in an individual (e.g., human) comprising administering to the individual an effective amount of a composition comprising nanoparticles comprising a limus drug and an albumin, wherein the nanoparticles comprise a limus drug associated (e.g., coated) with albumin, and wherein the nanoparticles have an average particle size of no greater than about 150 nm (such as no greater than about 120 nm). In some embodiments, there is provided a method of treating PEComa in an individual (e.g., human) comprising administering to the individual an effective amount of a composition comprising nanoparticles comprising sirolimus and human albumin, wherein the nanoparticles comprise sirolimus associated (e.g., coated) with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating PEComa-NOS in an individual (e.g., human) comprising administering to the individual an effective amount of a composition comprising Nab-sirolimus. In some embodiments, there is provided a method of treating a PEComa-NOS in an individual (e.g., human) comprising administering to the individual an effective amount of Nab-sirolimus. In some embodiments, the limus drug is administered at a dose of about 10 mg/m² to about 150 mg/m², including, for example, about 45 mg/m² to about 100 mg/m² and about 75 mg/m² to about 100 mg/m². In some embodiments, the limus drug is administered at a dose of about 100 mg/m². In some embodiments, the limus drug is administered at a dose of about 75 mg/m². In some embodiments, the limus drug is administered at a dose of about 56 mg/m². In some embodiments, the limus nanoparticle composition is administered weekly. In some embodiments, the limus nanoparticle composition is administered two out of every three weeks (e.g., days 1 and 8 of a 21-day cycle). In some embodiments, the limus nanoparticle composition is administered three out of four weeks (e.g., days 1, 8, and 15 of a 28-day cycle). In some embodiments, the limus nanoparticle composition is administered by intravenous infusion over 30 minutes.

In some embodiments, there is provided a method of treating a metastatic PEComa in an individual (e.g., human) comprising administering to the individual an effective amount of a composition comprising nanoparticles comprising an mTOR inhibitor (such as a limus drug) and an albumin. In some embodiments, there is provided a method of treating a metastatic PEComa in an individual (e.g., human) comprising administering to the individual an effective amount of a composition comprising nanoparticles comprising a limus drug and an albumin. In some embodiments, there is provided a method of treating a metastatic PEComa in an individual (e.g., human) comprising administering to the individual an effective amount of a composition comprising nanoparticles comprising a limus drug and an albumin, wherein the limus drug in the nanoparticles is associated (e.g., coated) with the albumin. In some embodiments, there is provided a method of treating a metastatic PEComa in an individual (e.g., human) comprising administering to the individual an effective amount of a composition comprising nanoparticles comprising a limus drug and an albumin, wherein the nanoparticles have an average particle size of no greater than about 150 nm (such as no greater than about 120 nm). In some embodiments, there is provided a method of treating a metastatic PEComa in an individual (e.g., human) comprising administering to the individual an effective amount of a composition comprising nanoparticles comprising a limus drug and an albumin, wherein the nanoparticles comprise a limus drug associated (e.g., coated) with albumin, and wherein the nanoparticles have an average particle size of no greater than about 150 nm (such as no greater than about 120 nm). In some embodiments, there is provided a method of treating a metastatic PEComa in an individual (e.g., human) comprising administering to the individual an effective amount of a composition comprising nanoparticles comprising sirolimus and human albumin, wherein the nanoparticles comprise sirolimus associated (e.g., coated) with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating a metastatic PEComa in an individual (e.g., human) comprising administering to the individual an effective amount of a composition comprising Nab-sirolimus. In some embodiments, there is provided a method of treating a metastatic PEComa in an individual (e.g., human) comprising administering to the individual an effective amount of Nab-sirolimus. In some embodiments, the limus drug is administered at a dose of about 10 mg/m² to about 150 mg/m², including, for example, about 45 mg/m² to about 100 mg/m² and about 75 mg/m² to about 100 mg/m². In some embodiments, the limus drug is administered at a dose of about 100 mg/m². In some embodiments, the limus drug is administered at a dose of about 75 mg/m². In some embodiments, the limus drug is administered at a dose of about 56 mg/m². In some embodiments, the limus nanoparticle composition is administered weekly. In some embodiments, the limus nanoparticle composition is administered two out of every three weeks (e.g., days 1 and 8 of a 21-day cycle). In some embodiments, the limus nanoparticle composition is administered three out of four weeks (e.g., days 1, 8, and 15 of a 28-day cycle). In some embodiments, the limus nanoparticle composition is administered by intravenous infusion over 30 minutes.

In some embodiments, there is provided a method of treating a locally advanced PEComa in an individual (e.g., human) comprising administering to the individual an effective amount of a composition comprising nanoparticles comprising an mTOR inhibitor (such as a limus drug) and an albumin. In some embodiments, there is provided a method of treating a locally advanced PEComa in an individual (e.g., human) comprising administering to the individual an effective amount of a composition comprising nanoparticles comprising a limus drug and an albumin. In some embodiments, there is provided a method of treating a locally advanced PEComa in an individual (e.g., human) comprising administering to the individual an effective amount of a composition comprising nanoparticles comprising a limus drug and an albumin, wherein the limus drug in the nanoparticles is associated (e.g., coated) with the albumin. In some embodiments, there is provided a method of treating a locally advanced PEComa in an individual (e.g., human) comprising administering to the individual an effective amount of a composition comprising nanoparticles comprising a limus drug and an albumin, wherein the nanoparticles have an average particle size of no greater than about 150 nm (such as no greater than about 120 nm). In some embodiments, there is provided a method of treating a locally advanced PEComa in an individual (e.g., human) comprising administering to the individual an effective amount of a composition comprising nanoparticles comprising a limus drug and an albumin, wherein the nanoparticles comprise a limus drug associated (e.g., coated) with albumin, and wherein the nanoparticles have an average particle size of no greater than about 150 nm (such as no greater than about 120 nm). In some embodiments, there is provided a method of treating a locally advanced PEComa in an individual (e.g., human) comprising administering to the individual an effective amount of a composition comprising nanoparticles comprising sirolimus and human albumin, wherein the nanoparticles comprise sirolimus associated (e.g., coated) with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating a locally advanced PEComa in an individual (e.g., human) comprising administering to the individual an effective amount of a composition comprising Nab-sirolimus. In some embodiments, there is provided a method of treating a locally advanced PEComa in an individual (e.g., human) comprising administering to the individual an effective amount of Nab-sirolimus. In some embodiments, the limus drug is administered at a dose of about 10 mg/m$^2$ to about 150 mg/m$^2$, including, for example, about 45 mg/m$^2$ to about 100 mg/m$^2$ and about 75 mg/m$^2$ to about 100 mg/m$^2$. In some embodiments, the limus drug is administered at a dose of about 100 mg/m$^2$. In some embodiments, the limus drug is administered at a dose of about 75 mg/m$^2$. In some embodiments, the limus drug is administered at a dose of about 56 mg/m$^2$. In some embodiments, the limus nanoparticle composition is administered weekly. In some embodiments, the limus nanoparticle composition is administered two out of every three weeks (e.g., days 1 and 8 of a 21-day cycle). In some embodiments, the limus nanoparticle composition is administered three out of four weeks (e.g., days 1, 8, and 15 of a 28-day cycle). In some embodiments, the limus nanoparticle composition is administered by intravenous infusion over 30 minutes.

In some embodiments, there is provided a method of treating an advanced malignant PEComa in an individual (e.g., human) comprising administering to the individual an effective amount of a composition comprising nanoparticles comprising an mTOR inhibitor (such as a limus drug) and an albumin. In some embodiments, there is provided a method of treating an advanced malignant PEComa in an individual (e.g., human) comprising administering to the individual an effective amount of a composition comprising nanoparticles comprising a limus drug and an albumin. In some embodiments, there is provided a method of treating an advanced malignant PEComa in an individual (e.g., human) comprising administering to the individual an effective amount of a composition comprising nanoparticles comprising a limus drug and an albumin, wherein the limus drug in the nanoparticles is associated (e.g., coated) with the albumin. In some embodiments, there is provided a method of treating an advanced malignant PEComa in an individual (e.g., human) comprising administering to the individual an effective amount of a composition comprising nanoparticles comprising a limus drug and an albumin, wherein the nanoparticles have an average particle size of no greater than about 150 nm (such as no greater than about 120 nm). In some embodiments, there is provided a method of treating an advanced malignant PEComa in an individual (e.g., human) comprising administering to the individual an effective amount of a composition comprising nanoparticles comprising a limus drug and an albumin, wherein the nanoparticles comprise a limus drug associated (e.g., coated) with albumin, and wherein the nanoparticles have an average particle size of no greater than about 150 nm (such as no greater than about 120 nm). In some embodiments, there is provided a method of treating an advanced malignant PEComa in an individual (e.g., human) comprising administering to the individual an effective amount of a composition comprising nanoparticles comprising sirolimus and human albumin, wherein the nanoparticles comprise sirolimus associated (e.g., coated) with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating an advanced malignant PEComa in an individual (e.g., human) comprising administering to the individual an effective amount of a composition comprising Nab-sirolimus. In some embodiments, there is provided a method of treating an advanced malignant PEComa in an individual (e.g., human) comprising administering to the individual an effective amount of Nab-sirolimus. In some embodiments, the limus drug is administered at a dose of about 10 mg/m$^2$ to about 150 mg/m$^2$, including, for example, about 45 mg/m$^2$ to about 100 mg/m$^2$ and about 75 mg/m$^2$ to about 100 mg/m$^2$. In some embodiments, the limus drug is administered at a dose of about 100 mg/m$^2$. In some embodiments, the limus drug is administered at a dose of about 75 mg/m$^2$. In some embodiments, the limus drug is administered at a dose of about 56 mg/m$^2$. In some embodiments, the limus nanoparticle composition is administered weekly. In some embodiments, the limus nanoparticle composition is administered two out of every three weeks (e.g., days 1 and 8 of a 21-day cycle). In some embodiments, the limus nanoparticle composition is administered three out of four weeks (e.g., days 1, 8, and 15 of a 28-day cycle). In some embodiments, the limus nanoparticle composition is administered by intravenous infusion over 30 minutes.

In some embodiments, there is provided a method of treating a recurrent PEComa in an individual (e.g., human) comprising administering to the individual an effective amount of a composition comprising nanoparticles comprising an mTOR inhibitor (such as a limus drug) and an albumin. In some embodiments, there is provided a method of treating a recurrent PEComa in an individual (e.g., human) comprising administering to the individual an effective amount of a composition comprising nanoparticles comprising a limus drug and an albumin. In some embodiments, there is provided a method of treating a recurrent PEComa in an individual (e.g., human) comprising administering to the individual an effective amount of a composition comprising nanoparticles comprising a limus drug and an albumin, wherein the limus drug in the nanoparticles is associated (e.g., coated) with the albumin. In some embodiments, there is provided a method of treating a recurrent PEComa in an individual (e.g., human) comprising administering to the individual an effective amount of a composition comprising nanoparticles comprising a limus drug and an albumin, wherein the nanoparticles have an average particle size of no greater than about 150 nm (such as no greater than about 120 nm). In some embodiments, there is provided a method of treating a recurrent PEComa in an individual (e.g., human) comprising administering to the individual an effective amount of a composition comprising nanoparticles comprising a limus drug and an albumin, wherein the nanoparticles comprise a limus drug associated (e.g., coated) with albumin, and wherein the nanoparticles have an average particle size of no greater than about 150 nm (such as no greater than about 120 nm). In some embodiments, there is provided a method of treating a recurrent PEComa in an individual (e.g., human) comprising administering to the individual an effective amount of a composition comprising nanoparticles comprising sirolimus and human albumin, wherein the nanoparticles comprise sirolimus associated (e.g., coated) with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of treating a recurrent PEComa in an individual (e.g., human) comprising administering to the individual an effective amount of a composition comprising Nab-sirolimus. In some embodiments, there is provided a method of treating a recurrent PEComa in an individual (e.g., human) comprising administering to the individual an effective amount of Nab-sirolimus. In some embodiments, the limus drug is administered at a dose of about 10 mg/m$^2$ to about 150 mg/m$^2$, including, for example, about 45 mg/m$^2$ to about 100 mg/m$^2$ and about 75 mg/m$^2$ to about 100 mg/m$^2$. In some embodiments, the limus drug is administered at a dose of about 100 mg/m$^2$. In some embodiments, the limus drug is administered at a dose of about 75 mg/m$^2$. In some embodiments, the limus drug is administered at a dose of about 56 mg/m$^2$. In some embodiments, the limus nanoparticle composition is administered weekly. In some embodiments, the limus nanoparticle composition is administered two out of every three weeks (e.g., days 1 and 8 of a 21-day cycle). In some embodiments, the limus nanoparticle composition is administered three out of four weeks (e.g., days 1, 8, and 15 of a 28-day cycle). In some embodiments, the limus nanoparticle composition is administered by intravenous infusion over 30 minutes.

In some embodiments, there is provided a method of stabilizing PEComa (e.g., preventing or delaying the worsening of the disease) in an individual (e.g., human) comprising administering to the individual an effective amount of a composition comprising nanoparticles comprising an mTOR inhibitor (such as a limus drug) and an albumin. In some embodiments, there is provided a method of stabilizing PEComa (e.g., preventing or delaying the worsening of the disease) in an individual (e.g., human) comprising administering to the individual an effective amount of a composition comprising nanoparticles comprising a limus drug and an albumin. In some embodiments, there is provided a method of stabilizing PEComa (e.g., preventing or delaying the worsening of the disease) in an individual (e.g., human) comprising administering to the individual an effective amount of a composition comprising nanoparticles comprising a limus drug and an albumin, wherein the limus drug in the nanoparticles is associated (e.g., coated) with the albumin. In some embodiments, there is provided a method of stabilizing PEComa (e.g., preventing or delaying the worsening of the disease) in an individual (e.g., human) comprising administering to the individual an effective amount of a composition comprising nanoparticles comprising a limus drug and an albumin, wherein the nanoparticles have an average particle size of no greater than about 150 nm (such as no greater than about 120 nm). In some embodiments, there is provided a method of stabilizing PEComa (e.g., preventing or delaying the worsening of the disease) in an individual (e.g., human) comprising administering to the individual an effective amount of a composition comprising nanoparticles comprising a limus drug and an albumin, wherein the nanoparticles comprise a limus drug associated (e.g., coated) with albumin, and wherein the nanoparticles have an average particle size of no greater than about 150 nm (such as no greater than about 120 nm). In some embodiments, there is provided a method of stabilizing PEComa (e.g., preventing or delaying the worsening of the disease) in an individual (e.g., human) comprising administering to the individual an effective amount of a composition comprising nanoparticles comprising sirolimus and human albumin, wherein the nanoparticles comprise sirolimus associated (e.g., coated) with the human albumin, wherein the nanoparticles have an average particle size of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, there is provided a method of stabilizing PEComa (e.g., preventing or delaying the worsening of the disease) in an individual (e.g., human) comprising administering to the individual an effective amount of a composition comprising Nab-sirolimus. In some embodiments, there is provided a method of stabilizing PEComa (e.g., preventing or delaying the worsening of the disease) in an individual (e.g., human) comprising administering to the individual an effective amount of Nab-sirolimus. In some embodiments, the limus drug is administered at a dose of about 10 mg/m$^2$ to about 150 mg/m$^2$, including, for example, about 45 mg/m$^2$ to about 100 mg/m$^2$ and about 75 mg/m$^2$ to about 100 mg/m$^2$. In some embodiments, the limus drug is administered at a dose of about 100 mg/m$^2$. In some embodiments, the limus drug is administered at a dose of about 75 mg/m$^2$. In some embodiments, the limus drug is administered at a dose of about 56 mg/m$^2$. In some embodiments, the limus nanoparticle composition is administered weekly. In some embodiments, the limus nanoparticle composition is administered two out of every three weeks (e.g., days 1 and 8 of a 21-day cycle). In some embodiments, the limus nanoparticle composition is administered three out of four weeks (e.g., days 1, 8, and 15 of a 28-day cycle). In some embodiments, the limus nanoparticle composition is administered by intravenous infusion over 30 minutes.

The methods described herein are useful for various aspects of treating a PEComa. In some embodiments, there is provided a method of inhibiting perivascular epithelioid cell proliferation (such as PEComa tumor growth) in an individual, comprising administering to the individual an effective amount of a composition comprising nanoparticles comprising an mTOR inhibitor and an albumin. In some embodiments, at least about 10% (including for example at least about any of 20%, 30%, 40%, 60%, 70%, 80%, 90%, or 100%) cell proliferation is inhibited. In some embodiments, the mTOR inhibitor is a limus drug. In some embodiments, the limus drug is sirolimus. In some embodiments, the limus drug in the nanoparticle in the composition is administered by intravenous administration. In some embodiments, the composition comprises nanoparticles comprising a limus drug associated (e.g., coated) with albumin. In some embodiments, the composition comprises nanoparticles having an average diameter of no greater than about 150 nm. In some embodiments, the composition comprises nanoparticles comprising a limus drug associated (e.g., coated) with albumin, wherein the nanoparticles have an average diameter of no greater than about 150 nm. In some embodiments, the composition comprises nanoparticles comprising sirolimus associated (e.g., coated) with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the limus nanoparticle composition is administered three out of four weeks (e.g., days 1, 8, and 15 of a 28-day cycle). In some embodiments, the composition comprises Nab-sirolimus. In some embodiments, the composition is Nab-sirolimus.

In some embodiments, there is provided a method of preventing local recurrence (e.g., recurrence of tumor after resection) in an individual having a PEComa, comprising administering to the individual an effective amount of a composition comprising nanoparticles comprising an mTOR inhibitor and an albumin. In some embodiments, at least about 10% (including for example at least about any of 20%, 30%, 40%, 60%, 70%, 80%, 90%, or 100%) metastasis is inhibited. In some embodiments, the mTOR inhibitor is a limus drug. In some embodiments, the limus drug is sirolimus. In some embodiments, the limus drug in the nanoparticle composition is administered by intravenous administration. In some embodiments, the composition comprises nanoparticles comprising a limus drug associated (e.g., coated) with albumin. In some embodiments, the composition comprises nanoparticles having an average diameter of no greater than about 150 nm. In some embodiments, the composition comprises nanoparticles comprising a limus drug associated (e.g., coated) with albumin, wherein the nanoparticles have an average diameter of no greater than about 150 nm. In some embodiments, the composition comprises nanoparticles comprising sirolimus associated (e.g., coated) with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of inhibiting a PEComa tumor metastasis in an individual, comprising administering to the individual an effective amount of a composition comprising nanoparticles comprising an mTOR inhibitor and an albumin. In some embodiments, at least about 10% (including for example at least about any of 20%, 30%, 40%, 60%, 70%, 80%, 90%, or 100%) metastasis is inhibited. In some embodiments, a method of inhibiting metastasis to lymph node is provided. In some embodiments, a method of inhibiting metastasis to the lung is provided. In some embodiments, the mTOR inhibitor is a limus drug. In some embodiments, the limus drug is sirolimus. In some embodiments, the limus drug in the nanoparticle composition is administered by intravenous administration. In some embodiments, the composition comprises nanoparticles comprising a limus drug associated (e.g., coated) with albumin. In some embodiments, the composition comprises nanoparticles having an average diameter of no greater than about 150 nm. In some embodiments, the composition comprises nanoparticles comprising a limus drug associated (e.g., coated) with albumin, wherein the nanoparticles have an average diameter of no greater than about 150 nm. In some embodiments, the composition comprises nanoparticles comprising sirolimus associated (e.g., coated) with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of reducing (such as eradiating) a pre-existing PEComa tumor metastasis (such as pulmonary metastasis or metastasis to the lymph node) in an individual, comprising administering to the individual an effective amount of a composition comprising nanoparticles comprising an mTOR inhibitor and an albumin. In some embodiments, at least about 10% (including for example at least about any of 20%, 30%, 40%, 60%, 70%, 80%, 90%, or 100%) metastasis is reduced. In some embodiments, a method of reducing metastasis to lymph node is provided. In some embodiments, a method of reducing metastasis to the lung is provided. In some embodiments, the mTOR inhibitor is a limus drug. In some embodiments, the limus drug is sirolimus. In some embodiments, the limus drug in the nanoparticle composition is administered by intravenous administration. In some embodiments, the composition comprises nanoparticles comprising a limus drug associated (e.g., coated) with albumin. In some embodiments, the composition comprises nanoparticles having an average diameter of no greater than about 150 nm. In some embodiments, the composition comprises nanoparticles comprising a limus drug associated (e.g., coated) with albumin, wherein the nanoparticles have an average diameter of no greater than about 150 nm. In some embodiments, the composition comprises nanoparticles comprising sirolimus associated (e.g., coated) with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of reducing incidence or burden of a preexisting PEComa tumor metastasis (such as pulmonary metastasis or metastasis to the lymph node) in an individual, comprising administering to the individual an effective amount of a composition comprising nanoparticles comprising an mTOR inhibitor and an albumin. In some embodiments, the mTOR inhibitor is a limus drug. In some embodiments, the limus drug is sirolimus. In some embodiments, the limus drug in the nanoparticle in the composition is administered by intravenous administration. In some embodiments, the composition comprises nanoparticles comprising a limus drug associated (e.g., coated) with albumin. In some embodiments, the composition comprises nanoparticles having an average diameter of no greater than about 150 nm. In some embodiments, the composition comprises nanoparticles comprising a limus drug associated (e.g., coated) with albumin, wherein the nanoparticles have an average diameter of no greater than about 150 nm. In some embodiments, the composition comprises nanoparticles comprising sirolimus associated (e.g., coated) with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of reducing the size of a PEComa in an individual, comprising administering to the individual an effective amount of a composition comprising nanoparticles comprising an mTOR inhibitor and an albumin. In some embodiments, the tumor size is reduced at least about 10% (including for example at least about any of 20%, 30%, 40%, 60%, 70%, 80%, 90%, or 100%). In some embodiments, the mTOR inhibitor is a limus drug. In some embodiments, the limus drug is sirolimus. In some embodiments, the limus drug in the nanoparticle composition is administered by intravenous administration. In some embodiments, the composition comprises nanoparticles comprising a limus drug associated (e.g., coated) with albumin. In some embodiments, the composition comprises nanoparticles having an average diameter of no greater than about 150 nm. In some embodiments, the composition comprises nanoparticles comprising a limus drug associated (e.g., coated) with albumin, wherein the nanoparticles have an average diameter of no greater than about 150 nm. In some embodiments, the composition comprises nanoparticles comprising sirolimus associated (e.g., coated) with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of prolonging time to disease progression of a PEComa in an individual, comprising administering to the individual an effective amount of a composition comprising nanoparticles comprising an mTOR inhibitor and an albumin. In some embodiments, the method prolongs the time to disease progression by at least any of 1, 2, 3, 4, 5, 6, 7, 8, 9, 10, 11, or 12 weeks. In some embodiments, the mTOR inhibitor is a limus drug. In some embodiments, the limus drug is sirolimus. In some embodiments, the limus drug in the nanoparticle composition is administered by intravenous administration. In some embodiments, the composition comprises nanoparticles comprising a limus drug associated (e.g., coated) with albumin. In some embodiments, the composition comprises nanoparticles having an average diameter of no greater than about 150 nm. In some embodiments, the composition comprises nanoparticles comprising a limus drug associated (e.g., coated) with albumin, wherein the nanoparticles have an average diameter of no greater than about 150 nm. In some embodiments, the composition comprises nanoparticles comprising sirolimus associated (e.g., coated) with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of prolonging survival of an individual having a PEComa, comprising administering to the individual an effective amount of a composition comprising nanoparticles comprising an mTOR inhibitor and an albumin. In some embodiments, the method prolongs the survival of the individual by at least any of 1, 2, 3, 4, 5, 6, 7, 8, 9, 10, 11, 12, 18, or 24 month. In some embodiments, the mTOR inhibitor is a limus drug. In some embodiments, the limus drug is sirolimus. In some embodiments, the limus drug in the nanoparticle composition is administered by intravenous administration. In some embodiments, the composition comprises nanoparticles comprising a limus drug associated (e.g., coated) with albumin. In some embodiments, the composition comprises nanoparticles having an average diameter of no greater than about 150 nm. In some embodiments, the composition comprises nanoparticles comprising a limus drug associated (e.g., coated) with albumin, wherein the nanoparticles have an average diameter of no greater than about 150 nm. In some embodiments, the composition comprises nanoparticles comprising sirolimus associated (e.g., coated) with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of alleviating one or more symptoms in an individual having a PEComa, comprising administering to the individual an effective amount of a composition comprising nanoparticles comprising an mTOR inhibitor and an albumin. In some embodiments, the mTOR inhibitor is a limus drug. In some embodiments, the limus drug is sirolimus. In some embodiments, the limus drug in the nanoparticle in the composition is administered by intravenous administration. In some embodiments, the composition comprises nanoparticles comprising a limus drug associated (e.g., coated) with albumin. In some embodiments, the composition comprises nanoparticles having an average diameter of no greater than about 150 nm. In some embodiments, the composition comprises nanoparticles comprising a limus drug associated (e.g., coated) with albumin, wherein the nanoparticles have an average diameter of no greater than about 150 nm. In some embodiments, the composition comprises nanoparticles comprising sirolimus associated (e.g., coated) with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the composition comprises Nab-sirolimus. In some embodiments, the composition is Nab-sirolimus.

In some embodiments, there is provided a method of suppression the progression of CIS (carcinoma in situ) lesions in an individual having a PEComa, comprising administering to the individual an effective amount of a composition comprising nanoparticles comprising an mTOR inhibitor and an albumin. In some embodiments, the mTOR inhibitor is a limus drug. In some embodiments, the limus drug is sirolimus. In some embodiments, the limus drug in the nanoparticle in the composition is administered by intravenous administration. In some embodiments, the composition comprises nanoparticles comprising a limus drug associated (e.g., coated) with albumin. In some embodiments, the composition comprises nanoparticles having an average diameter of no greater than about 150 nm. In some embodiments, the composition comprises nanoparticles comprising a limus drug associated (e.g., coated) with albumin, wherein the nanoparticles have an average diameter of no greater than about 150 nm. In some embodiments, the composition comprises nanoparticles comprising sirolimus associated (e.g., coated) with human albumin, wherein the nanoparticles have an average diameter of no greater than about 150 nm (such as no greater than about 120 nm, for example about 100 nm), wherein the weight ratio of human albumin and sirolimus in the composition is about 9:1 or less (such as about 9:1 or about 8:1). In some embodiments, the average or mean diameter of the nanoparticles is about 10 nm to about 150 nm. In some embodiments, the average or mean diameter of the nanoparticles is about 40 nm to about 120 nm. In some embodiments, the composition comprises Nab-sirolimus. In some embodiments, the composition is Nab-sirolimus.

In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 100 mg/m². In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 100 mg/m², and wherein the composition is administered weekly, 2 out of every 3 weeks (e.g., on days 1 and 8 of a 21-day cycle). In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 100 mg/m², wherein the composition is administered weekly, 2 out of every 3 weeks (e.g., on days 1 and 8 of a 21-day cycle), and wherein the dose is administered by intravenous infusion over 30 minutes. In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 100 mg/m², and wherein the composition is administered weekly, 3 out of every 4 weeks (e.g., on days 1, 8, and 15 of a 28-day cycle). In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 100 mg/m², wherein the composition is administered weekly, 3 out of every 4 weeks (e.g., on days 1, 8, and 15 of a 28-day cycle), and wherein the dose is administered by intravenous infusion over 30 minutes.

In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 75 mg/m². In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 75 mg/m², and wherein the composition is administered weekly, 2 out of every 3 weeks (e.g., on days 1 and 8 of a 21-day cycle). In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 75 mg/m², wherein the composition is administered weekly, 2 out of every 3 weeks (e.g., on days 1 and 8 of a 21-day cycle), and wherein the dose is administered by intravenous infusion over 30 minutes. In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 75 mg/m², and wherein the composition is administered weekly, 3 out of every 4 weeks (e.g., on days 1, 8, and 15 of a 28-day cycle). In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 75 mg/m², wherein the composition is administered weekly, 3 out of every 4 weeks (e.g., on days 1, 8, and 15 of a 28-day cycle), and wherein the dose is administered by intravenous infusion over 30 minutes.

In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 56 mg/m². In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 56 mg/m², and wherein the composition is administered weekly, 2 out of every 3 weeks (e.g., on days 1 and 8 of a 21-day cycle). In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 56 mg/m², wherein the composition is administered weekly, 2 out of every 3 weeks (e.g., on days 1 and 8 of a 21-day cycle), and wherein the dose is administered by intravenous infusion over 30 minutes. In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 56 mg/m², and wherein the composition is administered weekly, 3 out of every 4 weeks (e.g., on days 1, 8, and 15 of a 28-day cycle). In some embodiments, there is provided a method of treating a PEComa in an individual (e.g., human) comprising administering to the individual an effective amount of a composition comprising nanoparticles comprising sirolimus and an albumin (for example, nanoparticles comprising sirolimus coated with albumin, for example, Nab-sirolimus), wherein the composition is administered at a dose of 56 mg/m², wherein the composition is administered weekly, 3 out of every 4 weeks (e.g., on days 1, 8, and 15 of a 28-day cycle), and wherein the dose is administered by intravenous infusion over 30 minutes.

Also provided are pharmaceutical compositions comprising nanoparticles comprising an mTOR inhibitor (such as limus drug, for example sirolimus) for use in any of the methods of treating PEComa described herein. In some embodiments, the compositions comprise nanoparticles comprising an mTOR inhibitor (such as limus drug, for example sirolimus) and albumin (such as human albumin).

Use of Biomarkers

The present invention in one aspect provides methods of treating an epithelioid cell tumor, such as a PEComa, based on an expression or activity level or mutation status of one or more biomarkers.

In some embodiments, there is provided a method of treating a PEComa (such as a malignant PEComa, for example a metastatic or locally advanced PEComa) in an individual comprising administering to the individual an effective amount of a composition comprising nanoparticles comprising an mTOR inhibitor (such as a limus drug) and an albumin, wherein the individual is selected for treatment based on the individual having a mutation status in a gene. In some embodiments, the gene is selected from the ONCOPANEL™ test (CLIA certified). In some embodiments, the gene is an mTOR pathway gene. In some embodiments, the gene is an mTOR-associated pathway gene. As used here, "mTOR-associated pathway gene" refers to a gene that encodes a molecule, such as a protein, that directly or indirectly interacts in or with the mTOR signaling pathway. In some embodiments, the gene is selected from the group consisting of PIK3CA, TSC1, TSC2, AKT, PTEN, MTOR, and RHEB. In some embodiments, the gene is TFE3. In some embodiments, the mutation status is identified in a sample from the individual via cell-free DNA sequencing. In some embodiments, the mutation status is identified in a sample from the individual via exome sequencing. In some embodiments, the mutation status is identified in a sample from the individual via tumor biopsy mutation analysis. In some embodiments, the mutation status is identified in a sample from the individual via fluorescence in-situ hybridization. In some embodiments, the sample is a blood sample. In some embodiments, the sample is a tumor biopsy. In some embodiments, the sample is obtained prior to initiation of the treatment methods described herein. In some embodiments, the sample is obtained after initiation of the treatment methods described herein.

In some embodiments, there is provided a method of treating a PEComa (such as a malignant PEComa, for example a metastatic or locally advanced PEComa) in an individual comprising administering to the individual an effective amount of a composition comprising nanoparticles comprising an mTOR inhibitor (such as a limus drug) and an albumin, wherein the individual is selected for treatment based on the individual having a phosphorylation status of a protein associated with the mTOR signaling pathway. In some embodiments, the protein is selected from the group consisting of AKT, S6, S6K, 4EBP1, and SPARC. In some embodiments, the protein is phosphorylated. In some embodiments, the protein is phosphorylated at a specific amino acid site. In some embodiments, the protein is not phosphorylated. In some embodiments, the phosphorylation status is identified in a sample from the individual via immunohistochemistry. In some embodiments, the sample is a tumor biopsy.

In some embodiments, there is provided a method of treating a PEComa (such as a malignant PEComa, for example a metastatic or locally advanced PEComa) in an individual comprising administering to the individual an effective amount of a composition comprising nanoparticles comprising an mTOR inhibitor (such as a limus drug) and an albumin, wherein the individual is selected for treatment based on the individual having an expression level of a proliferation marker. In some embodiments, the proliferation marker is Ki-67. In some embodiments, the expression level of the proliferation marker is measured in a sample from the individual via immunohistochemistry. In some embodiments, the sample is a tumor biopsy. In some embodiments, there is provided a method of treating a PEComa (such as a malignant PEComa, for example a metastatic or locally advanced PEComa) in an individual comprising administering to the individual an effective amount of a composition comprising nanoparticles comprising an mTOR inhibitor (such as a limus drug) and an albumin, wherein the individual is selected for treatment based on the individual having an expression level of an apoptosis marker. In some embodiments, the apoptosis marker is PARP or a fragment thereof. In some embodiments, the expression level of the apoptosis marker is measured in a sample from the individual via immunohistochemistry. In some embodiments, the sample is a tumor biopsy.

In some embodiments, there is provided a method of treating a PEComa (such as a malignant PEComa, for example a metastatic or locally advanced PEComa) in an individual comprising administering to the individual an effective amount of a composition comprising nanoparticles comprising an mTOR inhibitor (such as a limus drug) and an albumin, wherein the nanoparticles have an average diameter of no greater than about 150 nm, and wherein the individual is selected for treatment based on the individual having a mutation status in a gene. In some embodiments, the gene is selected from the ONCOPANEL™ test. In some embodiments, the gene is selected from an mTOR pathway gene. In some embodiments, the gene is an mTOR-associated pathway gene. In some embodiments, the gene is selected from the group consisting of PIK3CA, TSC1, TSC2, AKT, PTEN, MTOR, and RHEB. In some embodiments, the gene is TFE3. In some embodiments, the mutation status is identified in a sample from the individual via cell-free DNA sequencing. In some embodiments, the mutation status is identified in a sample from the individual via exome sequencing. In some embodiments, the mutation status is identified in a sample from the individual via tumor biopsy mutation analysis. In some embodiments, the mutation status is identified in a sample from the individual via fluorescence in-situ hybridization. In some embodiments, the sample is a blood sample. In some embodiments, the sample is a tumor biopsy. In some embodiments, the sample is obtained prior to initiation of the treatment methods described herein. In some embodiments, the sample is obtained after initiation of the treatment methods described herein.

In some embodiments, there is provided a method of treating a PEComa (such as a malignant PEComa, for example a metastatic or locally advanced PEComa) in an individual comprising administering to the individual an effective amount of a composition comprising nanoparticles comprising an mTOR inhibitor (such as a limus drug) and an albumin, wherein the nanoparticles have an average diameter of no greater than about 150 nm, wherein the individual is selected for treatment based on the individual having a phosphorylation status of a protein associated with the mTOR signaling pathway. In some embodiments, the protein is selected from the group consisting of AKT, S6, S6K, 4EBP1, and SPARC. In some embodiments, the protein is phosphorylated. In some embodiments, the protein is phosphorylated at a specific amino acid site. In some embodiments, the protein is not phosphorylated. In some embodiments, the phosphorylation status is identified in a sample from the individual via immunohistochemistry. In some embodiments, the sample is a tumor biopsy.

In some embodiments, there is provided a method of treating a PEComa (such as a malignant PEComa, for example a metastatic or locally advanced PEComa) in an individual comprising administering to the individual an effective amount of a composition comprising nanoparticles comprising an mTOR inhibitor (such as a limus drug) and an albumin, wherein the nanoparticles have an average diameter of no greater than about 150 nm, wherein the individual is selected for treatment based on the individual having an expression level of a proliferation marker. In some embodiments, the proliferation marker is Ki-67. In some embodiments, the expression level of the proliferation marker is measured in a sample from the individual via immunohistochemistry. In some embodiments, the sample is a tumor biopsy. In some embodiments, there is provided a method of treating a PEComa (such as a malignant PEComa, for example a metastatic or locally advanced PEComa) in an individual comprising administering to the individual an effective amount of a composition comprising nanoparticles comprising an mTOR inhibitor (such as a limus drug) and an albumin, wherein the individual is selected for treatment based on the individual having an expression level of an apoptosis marker. In some embodiments, the apoptosis marker is PARP or a fragment thereof. In some embodiments, the expression level of the apoptosis marker is measured in a sample from the individual via immunohistochemistry. In some embodiments, the sample is a tumor biopsy.

In some embodiments, there is provided a method of treating a PEComa (such as a malignant PEComa, for example a metastatic or locally advanced PEComa) in an individual comprising: (a) assessing a mutation status in a gene in the individual; and (b) administering to the individual an effective amount of a composition comprising nanoparticles comprising an mTOR inhibitor (such as a limus drug) and an albumin, wherein the individual is selected for treatment based on having the mutation status in the gene. In some embodiments, the gene is selected from the ONCOPANEL™ test. In some embodiments, the gene is selected from an mTOR pathway gene. In some embodiments, the gene is an mTOR-associated pathway gene. In some embodiments, the gene is selected from the group consisting of PIK3CA, TSC1, TSC2, AKT, PTEN, MTOR, and RHEB. In some embodiments, the gene is TFE3. In some embodiments, the mutation status is identified in a sample from the individual via cell-free DNA sequencing. In some embodiments, the mutation status is identified in a sample from the individual via exome sequencing. In some embodiments, the mutation status is identified in a sample from the individual via tumor biopsy mutation analysis. In some embodiments, the mutation status is identified in a sample from the individual via fluorescence in-situ hybridization. In some embodiments, the sample is a blood sample. In some embodiments, the sample is a tumor biopsy. In some embodiments, the sample is obtained prior to initiation of the treatment methods described herein. In some embodiments, the sample is obtained after initiation of the treatment methods described herein.

In some embodiments, there is provided a method of treating a PEComa (such as a malignant PEComa, for example a metastatic or locally advanced PEComa) in an individual comprising: (a) assessing a phosphorylation status of a protein in the individual; and (b) administering to the individual an effective amount of a composition comprising nanoparticles comprising an mTOR inhibitor (such as a limus drug) and an albumin, wherein the individual is selected for treatment based on having the phosphorylation status of the protein associated with the mTOR signaling pathway associated with the mTOR signaling pathway. In some embodiments, the protein is selected from the group consisting of AKT, S6, S6K, 4EBP1, and SPARC. In some embodiments, the protein is phosphorylated. In some embodiments, the protein is phosphorylated at a specific amino acid site. In some embodiments, the protein is not phosphorylated. In some embodiments, the phosphorylation status is identified in a sample from the individual via immunohistochemistry. In some embodiments, the sample is a tumor biopsy.

In some embodiments, there is provided a method of treating a PEComa (such as a malignant PEComa, for example a metastatic or locally advanced PEComa) in an individual comprising: (a) assessing an expression level of a proliferation marker in the individual; and (b) administering to the individual an effective amount of a composition comprising nanoparticles comprising an mTOR inhibitor (such as a limus drug) and an albumin, wherein the individual is selected for treatment based on the individual having the expression level of the proliferation marker. In some embodiments, the proliferation marker is Ki-67. In some embodiments, the expression level of the proliferation marker is measured in a sample from the individual via immunohistochemistry. In some embodiments, the sample is a tumor biopsy. In some embodiments, there is provided a method of treating a PEComa (such as a malignant PEComa, for example a metastatic or locally advanced PEComa) in an individual the individual having an expression level of a proliferation marker comprising: (a) assessing an expression level of an apoptosis marker in the individual; and (b) administering to the individual an effective amount of a composition comprising nanoparticles comprising an mTOR inhibitor (such as a limus drug) and an albumin, wherein the individual is selected for treatment based on the individual having the expression level of the apoptosis marker. In some embodiments, the apoptosis marker is PARP or a fragment thereof. In some embodiments, the expression level of the apoptosis marker is identified in a sample from the individual via immunohistochemistry. In some embodiments, the sample is a tumor biopsy.

In some embodiments, there is provided a method of treating a PEComa (such as a malignant PEComa, for example a metastatic or locally advanced PEComa) in an individual comprising: (a) assessing a mutation status in a gene in the individual; (b) selecting (e.g., identifying or recommending) the individual for treatment based on the individual having the mutation status in the gene; and (c) administering to the individual an effective amount of a composition comprising nanoparticles comprising an mTOR inhibitor (such as a limus drug) and an albumin. In some embodiments, the gene is selected from the ONCO-PANEL™ test. In some embodiments, the gene is selected from an mTOR pathway gene. In some embodiments, the gene is an mTOR-associated pathway gene. In some embodiments, the gene is selected from the group consisting of PIK3CA, TSC1, TSC2, AKT, PTEN, MTOR, and RHEB. In some embodiments, the gene is TFE3. In some embodiments, the mutation status is identified in a sample from the individual via cell-free DNA sequencing. In some embodiments, the mutation status is identified in a sample from the individual via exome sequencing. In some embodiments, the mutation status is identified in a sample from the individual via tumor biopsy mutation analysis. In some embodiments, the mutation status is identified in a sample from the individual via fluorescence in-situ hybridization. In some embodiments, the sample is a blood sample. In some embodiments, the sample is a tumor biopsy. In some embodiments, the sample is obtained prior to initiation of the treatment methods described herein. In some embodiments, the sample is obtained after initiation of the treatment methods described herein.

In some embodiments, there is provided a method of treating a PEComa (such as a malignant PEComa, for example metastatic or locally advanced PEComa) in an individual comprising: (a) assessing a phosphorylation status of a protein in the individual; (b) selecting (e.g., identifying or recommending) the individual for treatment based on the individual having the phosphorylation status of the protein; and (c) administering to the individual an effective amount of a composition comprising nanoparticles comprising an mTOR inhibitor (such as a limus drug) and an albumin. In some embodiments, the protein is selected from the group consisting of AKT, S6, S6K, 4EBP1, and SPARC. In some embodiments, the protein is phosphorylated. In some embodiments, the protein is phosphorylated at a specific amino acid site. In some embodiments, the protein is not phosphorylated. In some embodiments, the phosphorylation status is identified in a sample from the individual via immunohistochemistry. In some embodiments, the sample is a tumor biopsy.

In some embodiments, there is provided a method of treating a PEComa (such as a malignant PEComa, for example a metastatic or locally advanced PEComa) in an individual comprising: (a) assessing an expression level of a proliferation marker in the individual; (b) selecting (e.g., identifying or recommending) the individual for treatment based on the individual having the expression level of the proliferation marker; and (c) administering to the individual an effective amount of a composition comprising nanoparticles comprising an mTOR inhibitor (such as a limus drug) and an albumin, wherein the individual is selected for treatment based on the individual having the expression level of the proliferation marker. In some embodiments, the proliferation marker is Ki-67. In some embodiments, the expression level of the proliferation marker is measured in a sample from the individual via immunohistochemistry. In some embodiments, the sample is a tumor biopsy. In some embodiments, there is provided a method of treating a PEComa (such as a malignant PEComa, for example a metastatic or locally advanced PEComa) in an individual the individual having an expression level of a proliferation marker comprising: (a) assessing an expression level of an apoptosis marker in the individual; (b) selecting (e.g., identifying or recommending) the individual for treatment based on the individual having the expression level of the proliferation marker; and (c) administering to the individual an effective amount of a composition comprising nanoparticles comprising an mTOR inhibitor (such as a limus drug) and an albumin. In some embodiments, the apoptosis marker is PARP or a fragment thereof. In some embodiments, the expression level of the apoptosis marker is identified in a sample from the individual via immunohistochemistry. In some embodiments, the sample is a tumor biopsy.

In some embodiments, there is provided a method of selecting (including identifying or recommending) an individual having a PEComa (such as a malignant PEComa, for example a metastatic or locally advanced PEComa) for treating with a composition comprising nanoparticles comprising an mTOR inhibitor (such as a limus drug) and an albumin, wherein the method comprises: (a) assessing a mutation status in a gene in the individual; and (b) selecting or recommending the individual for treatment based on the individual having the mutation status in the gene. In some embodiments, the gene is selected from the ONCO-PANEL™ test. In some embodiments, the gene is selected from an mTOR pathway gene. In some embodiments, the gene is an mTOR-associated pathway gene. In some embodiments, the gene is selected from the group consisting of PIK3CA, TSC1, TSC2, AKT, PTEN, MTOR, and RHEB. In some embodiments, the gene is TFE3. In some embodiments, the mutation status is identified in a sample from the individual via cell-free DNA sequencing. In some embodiments, the mutation status is identified in a sample from the individual via exome sequencing. In some embodiments, the mutation status is identified in a sample from the individual via tumor biopsy mutation analysis. In some embodiments, the mutation status is identified in a sample from the individual via fluorescence in-situ hybridization. In some embodiments, the sample is a blood sample. In some embodiments, the sample is a tumor biopsy. In some embodiments, the sample is obtained prior to initiation of the treatment methods described herein. In some embodiments, the sample is obtained after initiation of the treatment methods described herein.

In some embodiments, there is provided a method of selecting (including identifying or recommending) an individual having a PEComa (such as a malignant PEComa, for example a metastatic or locally advanced PEComa) for treating with a composition comprising nanoparticles comprising an mTOR inhibitor (such as a limus drug) and an albumin, wherein the method comprises: (a) assessing a phosphorylation status of a protein in the individual; and (b) selecting or recommending the individual for treatment based on the individual having the phosphorylation status of the protein associated with the mTOR signaling pathway. In some embodiments, the protein is selected from the group consisting of AKT, S6, S6K, 4EBP1, and SPARC. In some embodiments, the protein is phosphorylated. In some embodiments, the protein is phosphorylated at a specific amino acid site. In some embodiments, the protein is not phosphorylated. In some embodiments, the phosphorylation status is identified in a sample from the individual via immunohistochemistry. In some embodiments, the sample is a tumor biopsy.

In some embodiments, there is provided a method of selecting (including identifying or recommending) an individual having a PEComa (such as a malignant PEComa, for example a metastatic or locally advanced PEComa) for treating with a composition comprising nanoparticles comprising an mTOR inhibitor (such as a limus drug) and an albumin, wherein the method comprises: (a) assessing an expression level of a proliferation marker in the individual; and (b) selecting or recommending the individual for treatment based on the individual having the expression level of the proliferation marker. In some embodiments, the proliferation marker is Ki-67. In some embodiments, the expression level of the proliferation marker is measured in a sample from the individual via immunohistochemistry. In some embodiments, the sample is a tumor biopsy. In some embodiments, there is provided a method of selecting (including identifying or recommending) an individual having a PEComa (such as a malignant PEComa, for example a metastatic or locally advanced PEComa) for treating with a composition comprising nanoparticles comprising an mTOR inhibitor (such as a limus drug) and an albumin, wherein the method comprises: (a) assessing an expression level of an apoptosis marker in the individual; and (b) selecting (e.g., identifying or recommending) the individual for treatment based on the individual having the expression level of the proliferation marker. In some embodiments, the apoptosis marker is PARP or a fragment thereof. In some embodiments, the expression level of the apoptosis marker is identified in a sample from the individual via immunohistochemistry. In some embodiments, the sample is a tumor biopsy.

In some embodiments, there is provided a method of selecting (including identifying or recommending) an individual having a PEComa (such as a malignant PEComa, for example a metastatic or locally advanced PEComa) for treating with a composition comprising nanoparticles comprising an mTOR inhibitor (such as a limus drug) and an albumin, wherein the method comprises: (a) assessing a mutation status in a gene in the individual; (b) selecting or recommending the individual for treatment based on the individual having the mutation status in the gene; and (c) administering an effective amount of the composition comprising nanoparticles comprising the limus drug and the albumin to the selected individual. In some embodiments, the gene is selected from the ONCOPANEL™ test. In some embodiments, the gene is selected from an mTOR pathway gene. In some embodiments, the gene is an mTOR-associated pathway gene. In some embodiments, the gene is selected from the group consisting of PIK3CA, TSC1, TSC2, AKT, PTEN, MTOR, and RHEB. In some embodiments, the gene is TFE3. In some embodiments, the mutation status is identified in a sample from the individual via cell-free DNA sequencing. In some embodiments, the mutation status is identified in a sample from the individual via exome sequencing. In some embodiments, the mutation status is identified in a sample from the individual via tumor biopsy mutation analysis. In some embodiments, the mutation status is identified in a sample from the individual via fluorescence in-situ hybridization. In some embodiments, the sample is a blood sample. In some embodiments, the sample is a tumor biopsy. In some embodiments, the sample is obtained prior to initiation of the treatment methods described herein. In some embodiments, the sample is obtained after initiation of the treatment methods described herein.

In some embodiments, there is provided a method of selecting (including identifying or recommending) an individual having a PEComa (such as a malignant PEComa, for example a metastatic or locally advanced PEComa) for treating with a composition comprising nanoparticles comprising an mTOR inhibitor (such as a limus drug) and an albumin, wherein the method comprises: (a) assessing a phosphorylation status in a protein in the individual; (b) selecting or recommending the individual for treatment based on the individual having the phosphorylation status in the protein; and (c) administering an effective amount of the composition comprising nanoparticles comprising the limus drug and the albumin to the selected individual. In some embodiments, the protein is selected from the group consisting of AKT, S6, S6K, 4EBP1, and SPARC. In some embodiments, the protein is phosphorylated. In some embodiments, the protein is phosphorylated at a specific amino acid site. In some embodiments, the protein is not phosphorylated. In some embodiments, the phosphorylation status is identified in a sample from the individual via immunohistochemistry. In some embodiments, the sample is a tumor biopsy.

In some embodiments, there is provided a method of selecting (including identifying or recommending) an individual having a PEComa (such as a malignant PEComa, for example a metastatic or locally advanced PEComa) for treating with a composition comprising nanoparticles comprising an mTOR inhibitor (such as a limus drug) and an albumin, wherein the method comprises: (a) assessing an expression level of a proliferation marker in the individual; (b) selecting or recommending the individual for treatment based on the individual having the expression level of the proliferation marker; and (c) administering an effective amount of the composition comprising nanoparticles comprising the limus drug and the albumin to the selected individual. In some embodiments, the proliferation marker is Ki-67. In some embodiments, the expression level of the proliferation marker is measured in a sample from the individual via immunohistochemistry. In some embodiments, the sample is a tumor biopsy. In some embodiments, there is provided a method of selecting (including identifying or recommending) an individual having a PEComa (such as a malignant PEComa, for example metastatic or locally advanced PEComa) for treating with a composition comprising nanoparticles comprising an mTOR inhibitor (such as a limus drug) and an albumin, wherein the method comprises: (a) assessing an expression level of an apoptosis marker in the individual; (b) selecting or recommending the individual for treatment based on the individual having the expression level of the apoptosis marker; and (c) administering an effective amount of the composition comprising nanoparticles comprising the limus drug and the albumin to the selected individual. In some embodiments, the apoptosis marker is PARP or a fragment thereof. In some embodiments, the expression level of the apoptosis marker is identified in a sample from the individual via immunohistochemistry. In some embodiments, the sample is a tumor biopsy.

Also provided herein are methods of assessing whether an individual with a PEComa (such as a malignant PEComa, for example a metastatic or locally advanced PEComa) is more likely to respond or less likely to respond to treatment based on the individual having a mutation status in a gene, wherein the treatment comprises a composition comprising nanoparticles comprising an mTOR inhibitor (such as a limus drug) and an albumin, and wherein the method comprising assessing the mutation status of the gene in the individual. In some embodiments, the method further comprises administering to the individual an effective amount of the composition comprising nanoparticles comprising an mTOR inhibitor (such as a limus drug) and an albumin to the individual who is determined to be likely to respond to the treatment. In some embodiments, the presence of a mutation in the gene indicates that the individual is more likely to respond to the treatment, and the absence of a mutation in the gene indicates that the individual is less likely to respond to the treatment. In some embodiments, the gene is selected from the ONCOPANEL™ test. In some embodiments, the gene is selected from an mTOR pathway gene. In some embodiments, the gene is an mTOR-associated pathway gene. In some embodiments, the gene is selected from the group consisting of PIK3CA, TSC1, TSC2, AKT, PTEN, MTOR, and RHEB. In some embodiments, the gene is TFE3. In some embodiments, the mutation status is identified in a sample from the individual via cell-free DNA sequencing. In some embodiments, the mutation status is identified in a sample from the individual via exome sequencing. In some embodiments, the mutation status is identified in a sample from the individual via tumor biopsy mutation analysis. In some embodiments, the mutation status is identified in a sample from the individual via fluorescence in-situ hybridization. In some embodiments, the sample is a blood sample. In some embodiments, the sample is a tumor biopsy. In some embodiments, the sample is obtained prior to initiation of the treatment methods described herein. In some embodiments, the sample is obtained after initiation of the treatment methods described herein.

Also provided herein are methods of assessing whether an individual with a PEComa (such as a malignant PEComa, for example a metastatic or locally advanced PEComa) is more likely to respond or less likely to respond to treatment based on the individual having a phosphorylation status in a protein, wherein the treatment comprises a composition comprising nanoparticles comprising an mTOR inhibitor (such as a limus drug) and an albumin, and wherein the method comprising assessing the phosphorylation status of the protein in the individual. In some embodiments, the method further comprises administering to the individual an effective amount of the composition comprising nanoparticles comprising an mTOR inhibitor (such as a limus drug) and an albumin to the individual who is determined to be likely to respond to the treatment. In some embodiments, the phosphorylated protein indicates that the individual is more likely to respond to the treatment. In some embodiments, the unphosphorylated protein indicates that the individual is more likely to respond to the treatment.

Also provided herein are methods of assessing whether an individual with a PEComa (such as a malignant PEComa, for example a metastatic or locally advanced PEComa) is more likely to respond or less likely to respond to treatment based on the individual having an expression level of a proliferation marker, wherein the treatment comprises a composition comprising nanoparticles comprising an mTOR inhibitor (such as a limus drug) and an albumin, and wherein the method comprising assessing the expression level of the proliferation marker in the individual. In some embodiments, the method further comprises administering to the individual an effective amount of the composition comprising nanoparticles comprising an mTOR inhibitor (such as a limus drug) and an albumin to the individual who is determined to be likely to respond to the treatment. In some embodiments, the expression level of the proliferation marker indicates that the individual is more likely to respond to the treatment. In some embodiments, the proliferation marker is Ki-67. In some embodiments, the expression level of the proliferation marker is measured in a sample from the individual via immunohistochemistry. In some embodiments, the sample is a tumor biopsy. Further provided herein are methods of assessing whether an individual with a PEComa (such as a malignant PEComa, for example a metastatic or locally advanced PEComa) is more likely to respond or less likely to respond to treatment based on the individual having an expression level of an apoptosis marker, wherein the treatment comprises a composition comprising nanoparticles comprising an mTOR inhibitor (such as a limus drug) and an albumin, and wherein the method comprising assessing the expression level of the apoptosis marker in the individual. In some embodiments, the method further comprises administering to the individual an effective amount of the composition comprising nanoparticles comprising an mTOR inhibitor (such as a limus drug) and an albumin to the individual who is determined to be likely to respond to the treatment. In some embodiments, the expression level of the apoptosis marker indicates that the individual is less likely to respond to the treatment. In some embodiments, the apoptosis marker is PARP or a fragment thereof. In some embodiments, the expression level of the proliferation marker is measured in a sample from the individual via immunohistochemistry. In some embodiments, the sample is a tumor biopsy.

The mutation status of a gene may be assessed from a variety of sample sources. In some embodiments, the sample is a blood sample. In some embodiments, cell-free DNA is isolated from the blood sample. In some embodiments, the sample is a tumor biopsy. The mutation status of a gene may be assessed via a variety of methods well known by one of ordinary skill in that art. In some embodiments, the mutation status of the gene is assessed using cell-free DNA sequencing methods. In some embodiments, the mutation status of the gene is assessed using next-generation sequencing. In some embodiments, the mutation status of the gene isolated from a blood sample is assessed using next-generation sequencing. In some embodiments, the mutation status of the gene is assessed using exome sequencing. In some embodiments, the mutation status of a gene is assessed using fluorescence in-situ hybridization analysis. In some embodiments, the mutation status is assessed prior to initiation of the methods of treatment described herein. In some embodiments, the mutation status is assessed after initiation of the methods of treatment described herein. In some embodiments, the mutation status is assessed prior to and after initiation of the methods of treatment described herein.

The phosphorylation status of a protein may be assessed from a variety of sample sources. In some embodiments, the sample is a tumor biopsy. The phosphorylation status of a protein may be assessed via a variety of methods well known by one of ordinary skill in that art. In some embodiments, the phosphorylation status is assessed using immunohistochemistry. The phosphorylation status of a protein may be site specific. The phosphorylation status of a protein may be compared to a control sample. In some embodiments, the phosphorylation status is assessed prior to initiation of the methods of treatment described herein. In some embodiments, the phosphorylation status is assessed after initiation of the methods of treatment described herein. In some embodiments, the phosphorylation status is assessed prior to and after initiation of the methods of treatment described herein. In some embodiments, the protein is phosphorylated. In some embodiments, the protein is not phosphorylated. In some embodiments, the site specific amino acid is phosphorylated. In some embodiments, the site specific amino acid is not phosphorylated.

The expression level of a protein (such as a proliferation or an apoptosis marker) may be a high level or a low level as compared to a control sample. In some embodiments, the level of the protein in an individual is compared to the level of the protein in a control sample. In some embodiments the level of the protein in a subject is compared to the level of the protein in multiple control samples. In some embodiments, multiple control samples are used to generate a statistic that is used to classify the level of the protein in an individual with PEComa. The phosphorylation status of a protein may be compared to a control sample. In some embodiments, the expression level is assessed prior to initiation of the methods of treatment described herein. In some embodiments, the expression level is assessed after initiation of the methods of treatment described herein. In some embodiments, the expression level is assessed prior to and after initiation of the methods of treatment described herein.

The classification or ranking of the protein level (e.g., high or low) may be determined relative to a statistical distribution of control levels. In some embodiments, the classification or ranking is relative to a control sample obtained from the individual. In some embodiment, the levels of the protein is classified or ranked relative to a statistical distribution of control levels. In some embodiments, the level of the protein is classified or ranked relative to the level from a control sample obtained from the subject.

Control samples can be obtained using the same sources and methods as non-control samples. In some embodiments, the control sample is obtained from a different individual (for example an individual not having PEComa and/or an individual sharing similar ethnic, age, and gender identity). In some embodiments when the sample is a tumor tissue sample, the control sample may be a non-cancerous sample from the same individual. In some embodiments, multiple control samples (for example from different individuals) are used to determine a range of levels of biomarkers in a particular tissue, organ, or cell population. In some embodiments, the control sample is a cultured tissue or cell that has been determined to be a proper control. In some embodiments, the control is a cell that does not express the biomarker. In some embodiments, a clinically accepted normal level in a standardized test is used as a control level for determining the biomarker level. In some embodiments, the reference level of biomarker in the subject is classified as high, medium or low according to a scoring system, such as an immunohistochemistry-based scoring system. In some embodiments, the reference level of biomarker in the subject is classified as a low sample when the score is less than or equal to the overall median score.

In some embodiments, the biomarker level is determined by measuring the level of a biomarker in an individual and comparing to a control or reference (e.g., the median level for the given patient population or level of a second individual). For example, if the level of a biomarker for the single individual is determined to be above the median level of the patient population, that individual is determined to have a high level of the biomarker. Alternatively, if the level of a biomarker for the single individual is determined to be below the median level of the patient population, that individual is determined to have a low level of the biomarker. In some embodiments, the individual is compared to a second individual and/or a patient population which is responsive to treatment. In some embodiments, the individual is compared to a second individual and/or a patient population which is not responsive to treatment. In any of the embodiments herein, the levels can be determined by measuring the level of a nucleic acid encoding a biomarker. For example, if the level of an mRNA encoding a biomarker for the single individual is determined to be above the median level of the patient population, that individual is determined to have a high level of an mRNA encoding the biomarker. Alternatively, if the level of mRNA encoding the biomarker for the single individual is determined to be below the median level of the patient population, that individual is determined to have a low level of an mRNA encoding the biomarker.

In some embodiments, the reference level of a biomarker is determined by obtaining a statistical distribution of biomarker levels.

In some embodiments, bioinformatics methods are used for the determination and classification of the levels of the biomarker. Numerous alternative bioinformatics approaches have been developed to assess gene set expression profiles using gene expression profiling data. Methods include but are not limited to those described in Segal, E. et al. Nat. Genet. 34:66-176 (2003); Segal, E. et al. Nat. Genet. 36:1090-1098 (2004); Barry, W. T. et al. Bioinformatics 21:1943-1949 (2005); Tian, L. et al. Proc Nat'l Acad Sci USA 102:13544-13549 (2005); Novak B A and Jain A N. Bioinformatics 22:233-41 (2006); Maglietta R et al. Bioinformatics 23:2063-72 (2007); Bussemaker H J, BMC Bioinformatics 8 Suppl 6:S6 (2007).

In some embodiments, protein expression level is determined, for example by immunohistochemistry. For example, the criteria for low or high levels can be made based on the number of positive staining cells and/or the intensity of the staining, for example by using an antibody that specifically recognizes the biomarker protein. In some embodiments, the level is low if less than about 1%, 5%, 10%, 15%, 20%, 25%, 30%, 35%, 40%, 45%, or 50% cells have positive staining. In some embodiments, the level is low if the staining is 1%, 5%, 10%, 15%, 20%, 25%, 30%, 35%, 40%, 45%, or 50% less intense than a positive control staining.

In some embodiments, the level is high if more than about 40%, 45%, 50%, 55%, 60%, 65%, 70%, 75%, 80%, 85%, or 90%, cells have positive staining. In some embodiments, the level is high if the staining is as intense as positive control staining. In some embodiments, the level is high if the staining is 80%, 85%, or 90% as intense as positive control staining.

In some embodiments, strong staining, moderate staining, and weak staining are calibrated levels of staining, wherein a range is established and the intensity of staining is binned within the range. In some embodiments, strong staining is staining above the 75th percentile of the intensity range, moderate staining is staining from the 25th to the 75th percentile of the intensity range, and low staining is staining below the 25th percentile of the intensity range. In some aspects one skilled in the art, and familiar with a particular staining technique, adjusts the bin size and defines the staining categories.

In some embodiments, a biomarker is evaluated from a blood sample. In some embodiments, a biomarker is evaluated from a cell-free DNA sample. In some embodiments, a biomarker is evaluated using next-generation sequencing. In some embodiments, a biomarker is evaluated from a tumor biopsy. In some embodiments, a biomarker is evaluated using immunohistochemistry.

Further provided herein are methods of directing treatment of a PEComa by delivering a sample to a diagnostic lab for determination of biomarker levels; providing a control sample with a known level of a biomarker; providing an antibody to a biomarker; subjecting the sample and control sample to binding by the antibody, and/or detecting a relative amount of antibody binding, wherein the level of the sample is used to provide a conclusion that a patient should receive a treatment with any one of the methods described herein.

Also provided herein are methods of directing treatment of a disease, further comprising reviewing or analyzing data relating to the presence (or level) of a biomarker in a sample; and providing a conclusion to an individual, such as a health care provider or a health care manager, about the likelihood or suitability of the individual to respond to a treatment, the conclusion being based on the review or analysis of data. In one aspect of the invention a conclusion is the transmission of the data over a network.

The ONCOPANEL™ test can be used to survey exonic DNA sequences of cancer related genes and intronic regions for detection of genetic aberrations, including somatic mutations, copy number variations and structural rearrangements in DNA from various sources of samples (such as a tumor biopsy or blood sample), thereby providing a candidate list of genetic aberrations that may be mTOR-activating aberrations. In some embodiments, the mTOR-associated gene aberration is a genetic aberration or an aberrant level (such as expression level or activity level) in a gene selected from the ONCOPANEL™ test. See, for example, Wagle N. et at *Cancer discovery* 2.1 (2012): 82-93.

An exemplary version of ONCOPANEL™ test includes 300 cancer genes and 113 introns across 35 genes. The 300 genes included in the exemplary ONCOPANEL™ test are: ABL1, AKT1, AKT2, AKT3, ALK, ALOX12B, APC, AR, ARAF, ARID1A, ARID1B, ARID2, ASXL1, ATM, ATRX, AURKA, AURKB, AXL, B2M, BAP1, BCL2, BCL2L1, BCL2L12, BCL6, BCOR, BCORL1, BLM, BMPR1A, BRAF, BRCA1, BRCA2, BRD4, BRIP1, BUB1B, CADM2, CARD11, CBL, CBLB, CCND1, CCND2, CCND3, CCNE1, CD274, CD58, CD79B, CDC73, CDH1, CDK1, CDK2, CDK4, CDK5, CDK6, CDK9, CDKN1A, CDKN1B, CDKN1C, CDKN2A, CDKN2B, CDKN2C, CEBPA, CHEK2, CIITA, CREBBP, CRKL, CRLF2, CRTC1, CRTC2, CSF1R, CSF3R, CTNNB1, CUX1, CYLD, DDB2, DDR2, DEPDC5, DICER1, DIS3, DMD, DNMT3A, EED, EGFR, EP300, EPHA3, EPHA5, EPHA7, ERBB2, ERBB3, ERBB4, ERCC2, ERCC3, ERCC4, ERCC5, ESR1, ETV1, ETV4, ETV5, ETV6, EWSR1, EXT1, EXT2, EZH2, FAM46C, FANCA, FANCC, FANCD2, FANCE, FANCF, FANCG, FAS, FBXW7, FGFR1, FGFR2, FGFR3, FGFR4, FH, FKBP9, FLCN, FLT1, FLT3, FLT4, FUS, GATA3, GATA4, GATA6, GLI1, GLI2, GLI3, GNA11, GNAQ, GNAS, GNB2L1, GPC3, GSTM5, H3F3A, HNF1A, HRAS, ID3, IDH1, IDH2, IGF1R, IKZF1, IKZF3, INSIG1, JAK2, JAK3, KCNIP1, KDM5C, KDM6A, KDM6B, KDR, KEAP1, KIT, KRAS, LINC00894, LMO1, LMO2, LMO3, MAP2K1, MAP2K4, MAP3K1, MAPK1, MCL1, MDM2, MDM4, MECOM, MEF2B, MEN1, MET, MITF, MLH1, MLL (KMT2A), MLL2 (KTM2D), MPL, MSH2, MSH6, MTOR, MUTYH, MYB, MYBL1, MYC, MYCL1 (MYCL), MYCN, MYD88, NBN, NEGR1, NF1, NF2, NFE2L2, NFKBIA, NFKBIZ, NKX2-1, NOTCH1, NOTCH2, NPM1, NPRL2, NPRL3, NRAS, NTRK1, NTRK2, NTRK3, PALB2, PARK2, PAX5, PBRM1, PDCD1LG2, PDGFRA, PDGFRB, PHF6, PHOX2B, PIK3C2B, PIK3CA, PIK3R1, PIM1, PMS1, PMS2, PNRC1, PRAME, PRDM1, PRF1, PRKAR1A, PRKCI, PRKCZ, PRKDC, PRPF40B, PRPF8, PSMD13, PTCH1, PTEN, PTK2, PTPN11, PTPRD, QKI, RAD21, RAF1, RARA, RB1, RBL2, RECQL4, REL, RET, RFWD2, RHEB, RHPN2, ROS1, RPL26, RUNX1, SBDS, SDHA, SDHAF2, SDHB, SDHC, SDHD, SETBP1, SETD2, SF1, SF3B1, SH2B3, SLITRK6, SMAD2, SMAD4, SMARCA4, SMARCB1, SMC1A, SMC3, SMO, SOCS1, SOX2, SOX9, SQSTM1, SRC, SRSF2, STAG1, STAG2, STAT3, STAT6, STK11, SUFU, SUZ12, SYK, TCF3, TCF7L1, TCF7L2, TERC, TERT, TET2, TLR4, TNFAIP3, TP53, TSC1, TSC2, U2AF1, VHL, WRN, WT1, XPA, XPC, XPO1, ZNF217, ZNF708, ZRSR2. The intronic regions surveyed in the exemplary ONCOPANEL™ test are tiled on specific introns of ABL1, AKT3, ALK, BCL2, BCL6, BRAF, CIITA, EGFR, ERG, ETV1, EWSR1, FGFR1, FGFR2, FGFR3, FUS, IGH, IGL, JAK2, MLL, MYC, NPM1, NTRK1, PAX5, PDGFRA, PDGFRB, PPARG, RAF1, RARA, RET, ROS1, SS18, TRA, TRB, TRG, TMPRSS2. mTOR-activating aberrations (such as genetic aberration and aberrant levels) of any of the genes included in any embodiment or version of the ONCOPANEL™ test, including, but not limited to the genes and intronic regions listed above, are contemplated by the present application to serve as a basis for selecting an individual for treatment with the mTOR inhibitor nanoparticle compositions.

Dosing and Method of Administering the
Nanoparticle Compositions

The dose of the mTOR nanoparticles (such as a limus nanoparticle compositions) administered to an individual (such as a human) may vary with the particular composition, the mode of administration, and the type of PEComa being treated. In some embodiments, the amount of the composition is effective to result in an objective response (such as a partial response or a complete response). In some embodiments, the amount of the mTOR nanoparticle composition (such as a limus nanoparticle composition) is sufficient to result in a complete response in the individual. In some embodiments, the amount of the mTOR nanoparticle composition (such as a limus nanoparticle composition) is sufficient to result in a partial response in the individual. In some embodiments, the amount of the mTOR nanoparticle composition (such as a limus nanoparticle composition) administered (for example when administered alone) is sufficient to produce an overall response rate of more than about any of 20%, 30%, 40%, 50%, 60%, or 64% among a population of individuals treated with the mTOR nanoparticle composition (such as a limus nanoparticle composition). Responses of an individual to the treatment of the methods described herein can be determined, for example, based on RECIST levels, cystoscopy (with or without biopsy), biopsy, cytology, and CT imaging.

In some embodiments, the amount of the mTOR nanoparticle composition (such as a limus nanoparticle composition) is sufficient to produce a negative biopsy in the individual.

In some embodiments, the amount of the composition is sufficient to prolong progression-free survival of the individual. In some embodiments, the amount of the composition is sufficient to prolong overall survival of the individual. In some embodiments, the amount of the composition (for example when administered alone) is sufficient to produce clinical benefit of more than about any of 50%, 60%, 70%, or 77% among a population of individuals treated with the mTOR nanoparticle composition (such as a limus nanoparticle composition).

In some embodiments, the amount of the composition is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the mTOR inhibitor (such as a limus drug, for example sirolimus) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regime. In some embodiments, the amount of the composition is more than about any of 80%, 90%, 95%, or 98% of the MTD.

In some embodiments, the effective amounts of an mTOR inhibitor (e.g., a limus drug) in the nanoparticle composition include, but are not limited to, at least about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$ 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$ of an mTOR inhibitor (e.g., sirolimus). In various embodiments, the composition includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of an mTOR inhibitor (e.g., sirolimus). In some embodiments, the amount of the mTOR inhibitor (e.g., sirolimus) per administration is less than about any of 25 mg/m$^2$ 22 mg/m$^2$ 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the effective amount of an mTOR inhibitor (e.g., sirolimus) in the composition is included in any of the following ranges: about 1 to about 5 mg/m$^2$, about 5 to about 10 mg/m$^2$, about 10 to about 25 mg/m$^2$, about 25 to about 50 mg/m$^2$, about 50 to about 75 mg/m$^2$, about 75 to about 100 mg/m$^2$, about 100 to about 125 mg/m$^2$, about 125 to about 150 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. In some embodiments, the effective amount of an mTOR inhibitor (e.g., sirolimus) in the composition is about 5 to about 300 mg/m$^2$, such as about 100 to about 150 mg/m$^2$, about 120 mg/m$^2$, about 130 mg/m$^2$, or about 140 mg/m$^2$.

In some embodiments of any of the above aspects, the effective amount of an mTOR inhibitor (e.g., sirolimus) in the composition includes at least about any of 1 mg/kg, 2.5 mg/kg, 3.5 mg/kg, 5 mg/kg, 6.5 mg/kg, 7.5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, or 60 mg/kg. In various embodiments, the effective amount of an mTOR inhibitor (e.g., sirolimus) in the composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of an mTOR inhibitor (e.g., sirolimus).

In some embodiments, the dosing frequencies for the administration of the nanoparticle compositions include, but are not limited to, daily, every two days, every three days, every four days, every five days, every six days, weekly without break, three out of four weeks, once every three weeks, once every two weeks, or two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosing frequency is once every two days for one time, two times, three times, four times, five times, six times, seven times, eight times, nine times, ten times, and eleven times. In some embodiments, the dosing frequency is once every two days for five times. In some embodiments, the mTOR inhibitor (e.g., sirolimus) is administered over a period of at least ten days, wherein the interval between each administration is no more than about two days, and wherein the dose of the mTOR inhibitor (e.g., sirolimus) at each administration is about 0.25 mg/m$^2$ to about 250 mg/m$^2$, about 0.25 mg/m$^2$ to about 150 mg/m$^2$, about 0.25 mg/m$^2$ to about 75 mg/m$^2$, such as about 0.25 mg/m$^2$ to about 25 mg/m$^2$, or about 25 mg/m$^2$ to about 50 mg/m$^2$.

The administration of the composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

In some embodiments, the dosage of an mTOR inhibitor (e.g., sirolimus) in a nanoparticle composition can be in the range of 5-400 mg/m$^2$ when given on a 3 week schedule, or 5-250 mg/m$^2$ (such as 80-150 mg/m$^2$, for example 100-120 mg/m$^2$) when given on a weekly schedule. For example, the amount of an mTOR inhibitor (e.g., sirolimus) is about 60 to about 300 mg/m$^2$ (e.g., about 260 mg/m$^2$) on a three week schedule.

In some embodiments, the exemplary dosing schedules for the administration of the nanoparticle composition (e.g., sirolimus/albumin nanoparticle composition) include, but are not limited to, 100 mg/m$^2$, weekly, without break; 100 mg/m$^2$, weekly, 2 out of 3 weeks; 100 mg/m$^2$, weekly, 3 out of 4 weeks; 75 mg/m$^2$, weekly, without break; 75 mg/m$^2$, weekly, 2 out of 3 weeks; 75 mg/m$^2$, weekly, 3 out of 4 weeks; 56 mg/m$^2$, weekly, without break; 56 mg/m$^2$, weekly, 2 out of 3 weeks; 56 mg/m$^2$, weekly, 3 out of 4 weeks. The dosing frequency of the composition may be adjusted over the course of the treatment based on the judgment of the administering physician.

In some embodiments, the individual is treated for at least about any of one, two, three, four, five, six, seven, eight, nine, or ten treatment cycles.

The compositions described herein allow infusion of the composition to an individual over an infusion time that is shorter than about 24 hours. For example, in some embodiments, the composition is administered over an infusion period of less than about any of 24 hours, 12 hours, 8 hours, 5 hours, 3 hours, 2 hours, 1 hour, 30 minutes, 20 minutes, or 10 minutes. In some embodiments, the composition is administered over an infusion period of about 30 minutes.

In some embodiments, the exemplary dose of the mTOR inhibitor (in some embodiments a limus drug, for example, sirolimus) in the nanoparticle composition include, but 75 mg/m$^2$, 80 mg/m$^2$, 90 mg/m$^2$, 100 mg/m$^2$, 120 mg/m$^2$, 160 mg/m$^2$, 175 mg/m$^2$, 200 mg/m$^2$, 210 mg/m$^2$, 220 mg/m$^2$, 260 mg/m$^2$, and 300 mg/m$^2$. For example, the dosage of an mTOR inhibitor in a nanoparticle composition can be in the range of about 100-400 mg/m$^2$ when given on a 3 week schedule, or about 50-250 mg/m$^2$ when given on a weekly schedule.

The mTOR nanoparticle composition (such as a limus nanoparticle composition) can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used. In some embodiments, the composition is administered intravenously. In some embodiments, the composition is administered intravesicularly. In some embodiments, the composition is administered intraarterially. In some embodiments, the composition is administered intraperitoneally.

In some embodiments when the limus nanoparticle composition is administered intravesicularly, the dosage of an mTOR inhibitor (such as a limus drug, e.g., sirolimus) in a nanoparticle composition can be in the range of about 30 mg to about 400 mg in volume of about 20 to about 150 ml, for example retained in the bladder for about 30 minutes to about 4 hours. In some embodiments, the nanoparticle composition is retained in the bladder for about 30 minutes to about 4 hours, including for example about 30 minutes to about 1 hour, about 1 hour to about 2 hours, about 2 hours to about 3 hours, or about 3 hours to about 4 hours.

In some embodiments, the dosage of an mTOR inhibitor (such as a limus drug, e.g., sirolimus) is about 100 to about 400 mg, for example about 100 mg, about 200 mg, about 300 mg, or about 400 mg. In some embodiments, the limus drug is administered at about 100 mg weekly, about 200 mg weekly, about 300 mg weekly, about 100 mg twice weekly, or about 200 mg twice weekly. In some embodiments, the administration is further followed by a monthly maintenance dose (which can be the same or different from the weekly doses).

In some embodiments when the limus nanoparticle composition is administered intravenously, the dosage of an mTOR inhibitor (such as a limus drug, e.g., sirolimus) in a nanoparticle composition can be in the range of about 30 mg to about 400 mg. The compositions described herein allow infusion of the composition to an individual over an infusion time that is shorter than about 24 hours. For example, in some embodiments, the composition is administered over an infusion period of less than about any of 24 hours, 12 hours, 8 hours, 5 hours, 3 hours, 2 hours, 1 hour, 30 minutes, 20 minutes, or 10 minutes. In some embodiments, the composition is administered over an infusion period of about 30 minutes to about 40 minutes.

Nanoparticle Compositions

The nanoparticle compositions described herein comprise nanoparticles comprising (in various embodiments consisting essentially of) an mTOR inhibitor (such as a limus drug, for example sirolimus). The nanoparticles may further comprise an albumin (such as human serum albumin or human albumin). Nanoparticles of poorly water soluble drugs have been disclosed in, for example, U.S. Pat. Nos. 5,916,596; 6,506,405; 6,749,868, 6,537,579, 7,820,788, and also in U.S. Pat. Pub. Nos. 2006/0263434, and 2007/0082838; PCT Patent Application WO08/137148, each of which is incorporated by reference in their entirety.

In some embodiments, the composition comprises nanoparticles with an average or mean diameter of no greater than about 1000 nanometers (nm), such as no greater than about (or less than about) any of 900, 800, 700, 600, 500, 400, 300, 200, 150, 120, and 100 nm. In some embodiments, the average or mean diameters of the nanoparticles is no greater than about 150 nm (such as no greater than about 120 nm). In some embodiments, the average or mean diameters of the nanoparticles is no greater than about 120 nm. In some embodiments, the average or mean diameter of the nanoparticles is about 10 nm to about 150 nm. In some embodiments, the average or mean diameter of the nanoparticles is about 40 nm to about 120 nm. In some embodiments, the nanoparticles are sterile-filterable.

In some embodiments, the nanoparticles in the composition described herein have an average diameter of no greater than about 150 nm, including for example no greater than about any one of 140, 130, 120, 110, 100, 90, 80, 70, or 60 nm. In some embodiments, at least about 50% (for example at least about any one of 60%, 70%, 80%, 90%, 95%, or 99%) of the nanoparticles in the composition have a diameter of no greater than about 150 nm, including for example no greater than about any one of 140, 130, 120, 110, 100, 90, 80, 70, or 60 nm. In some embodiments, at least about 50% (for example at least any one of 60%, 70%, 80%, 90%, 95%, or 99%) of the nanoparticles in the composition fall within the range of about 20 nm to about 150 nm, including for example about 40 nm to about 120 nm.

In some embodiments, the albumin has sulfhydryl groups that can form disulfide bonds. In some embodiments, at least about 5% (including for example at least about any one of 10%, 15%, 20%, 25%, 30%, 40%, 50%, 60%, 70%, 80%, or 90%) of the albumin in the nanoparticle portion of the composition are crosslinked (for example crosslinked through one or more disulfide bonds).

In some embodiments, the nanoparticles comprising the mTOR inhibitor (such as a limus drug, e.g., sirolimus) are associated (e.g., coated) with an albumin (e.g., human albumin or human serum albumin). In some embodiments, the composition comprises an mTOR inhibitor (such as a limus drug, for example sirolimus) in both nanoparticle and non-nanoparticle forms (e.g., in the form of solutions or in the form of soluble albumin/nanoparticle complexes), wherein at least about any one of 50%, 60%, 70%, 80%, 90%, 95%, or 99% of the mTOR inhibitor (such as a limus drug, e.g., sirolimus) in the composition are in nanoparticle form. In some embodiments, the mTOR inhibitor (such as a limus drug, e.g., sirolimus) in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of an mTOR inhibitor (such as a limus drug, for example sirolimus) that is substantially free of polymeric materials (such as polymeric matrix).

In some embodiments, the composition comprises an albumin in both nanoparticle and non-nanoparticle portions of the composition, wherein at least about any one of 50%, 60%, 70%, 80%, 90%, 95%, or 99% of the albumin in the composition are in non-nanoparticle portion of the composition.

In some embodiments, the weight ratio of an albumin (such as human albumin or human serum albumin) and an mTOR inhibitor in the nanoparticle composition is about 18:1 or less, such as about 15:1 or less, for example about 10:1 or less. In some embodiments, the weight ratio of an albumin (such as human albumin or human serum albumin) and an mTOR inhibitor (such as a limus drug, for example sirolimus) in the composition falls within the range of any one of about 1:1 to about 18:1, about 2:1 to about 15:1, about 3:1 to about 13:1, about 4:1 to about 12:1, about 5:1 to about 10:1. In some embodiments, the weight ratio of an albumin and an mTOR inhibitor (such as a limus drug, for example sirolimus) in the nanoparticle portion of the composition is about any one of 1:2, 1:3, 1:4, 1:5, 1:9, 1:10, 1:15, or less. In some embodiments, the weight ratio of the albumin (such as human albumin or human serum albumin) and the mTOR inhibitor (such as a limus drug, e.g., sirolimus) in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the nanoparticle composition comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulfide bridges, one free thiol (Cys 34), and a single tryptophan (Trp 214). Intravenous use of HSA solution has been indicated for the prevention and treatment of hypovolumic shock (see, e.g., Tullis, *JAMA*, 237: 355-360, 460-463, (1977)) and Houser et al., *Surgery, Gynecology and Obstetrics*, 150: 811-816 (1980)) and in conjunction with exchange transfusion in the treatment of neonatal hyperbilirubinemia (see, e.g., Finlayson, Seminars in Thrombosis and Hemostasis, 6, 85-120, (1980)). Other albumins are contemplated, such as bovine serum albumin. Use of such non-human albumins could be appropriate, for example, in the context of use of these compositions in non-human mammals, such as the veterinary (including domestic pets and agricultural context). Human serum albumin (HSA) has multiple hydrophobic binding sites (a total of eight for fatty acids, an endogenous ligand of HSA) and binds a diverse set of drugs, especially neutral and negatively charged hydrophobic compounds (Goodman et al., *The Pharmacological Basis of Therapeutics*, 9th ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (198a), Vorum, *Dan. Med. Bull.*, 46, 37999 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (199b), and Carter et al., *Adv. Protein. Chem.*, 45, 153-203 (1994)). Sirolimus and propofol have been shown to bind HSA (see, e.g., Paal et al., *Eur. J. Biochem.*, 268(7), 2187-91 (200a), Purcell et al., *Biochim. Biophys. Acta*, 1478(a), 61-8 (2000), Altmayer et al., *Arzneimittelforschung*, 45, 1053-6 (1995), and Garrido et al., *Rev. Esp. Anestestiol. Reanim.*, 41, 308-12 (1994)). In addition, docetaxel has been shown to bind to human plasma proteins (see, e.g., Urien et al., *Invest. New Drugs*, 14(b), 147-51 (1996)).

The albumin (e.g., human albumin or human serum albumin) in the composition generally serves as a carrier for the mTOR inhibitor, i.e., the albumin in the composition makes the mTOR inhibitor (such as a limus drug, e.g., sirolimus) more readily suspendable in an aqueous medium or helps maintain the suspension as compared to compositions not comprising an albumin. This can avoid the use of toxic solvents (or surfactants) for solubilizing the mTOR inhibitor, and thereby can reduce one or more side effects of administration of the mTOR inhibitor (such as a limus drug, e.g., sirolimus) into an individual (such as a human). Thus, in some embodiments, the composition described herein is substantially free (such as free) of surfactants, such as Cremophor (or polyoxyethylated castor oil, including Cremophor EL® (BASF)). In some embodiments, the nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the nanoparticle composition is administered to the individual. In some embodiments, the nanoparticle composition contains less than about any one of 20%, 15%, 10%, 7.5%, 5%, 2.5%, or 1% organic solvent or surfactant. In some embodiments, the albumin is human albumin or human serum albumin. In some embodiments, the albumin is recombinant albumin.

The amount of an albumin in the composition described herein will vary depending on other components in the composition. In some embodiments, the composition comprises an albumin in an amount that is sufficient to stabilize the mTOR inhibitor (such as a limus drug, e.g., sirolimus) in an aqueous suspension, for example, in the form of a stable colloidal suspension (such as a stable suspension of nanoparticles). In some embodiments, the albumin is in an amount that reduces the sedimentation rate of the mTOR inhibitor (such as a limus drug, e.g., sirolimus) in an aqueous medium. For particle-containing compositions, the amount of the the albumin also depends on the size and density of nanoparticles of the mTOR inhibitor.

An mTOR inhibitor (such as a limus drug, for example sirolimus) is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the albumin is present in an amount that is sufficient to stabilize the mTOR inhibitor (such as a limus drug, e.g., sirolimus) in an aqueous suspension at a certain concentration. For example, the concentration of the mTOR inhibitor (such as a limus drug, e.g., sirolimus) in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of the mTOR inhibitor (such as a limus drug, e.g., sirolimus) is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the albumin is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of an albumin. In some embodiments, the composition, in liquid form, comprises about 0.5% to about 5% (w/v) of an albumin.

In some embodiments, the weight ratio of albumin to the mTOR inhibitor (such as a limus drug, e.g., sirolimus) in the nanoparticle composition is such that a sufficient amount of mTOR inhibitor binds to, or is transported into, the cell. While the weight ratio of an albumin to mTOR inhibitor will have to be optimized for different albumins and mTOR inhibitor combinations, generally the weight ratio of an albumin, to mTOR inhibitor (such as a limus drug, e.g., sirolimus) (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the albumin to mTOR inhibitor weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the weight ratio of the albumin (such as human albumin or human serum albumin) to the mTOR inhibitor in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the albumin allows the composition to be administered to an individual (such as human) without significant side effects. In some embodiments, the albumin (such as human serum albumin or human albumin) is in an amount that is effective to reduce one or more side effects of administration of the mTOR inhibitor (such as a limus drug, e.g., sirolimus) to a human. The term "reducing one or more side effects" of administration of the mTOR inhibitor (such as a limus drug, e.g., sirolimus) refers to reduction, alleviation, elimination, or avoidance of one or more undesirable effects caused by the mTOR inhibitor, as well as side effects caused by delivery vehicles (such as solvents that render the limus drugs suitable for injection) used to deliver the mTOR inhibitor. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with limus drugs (such as sirolimus) can be reduced.

In some embodiments, the nanoparticle compositions described herein comprise nanoparticles comprising an mTOR inhibitor (such as a limus drug, for example sirolimus) and an albumin (such as human albumin or human serum albumin), wherein the nanoparticles have an average diameter of no greater than about 150 nm. In some embodiments, the nanoparticle compositions described herein comprises nanoparticles comprising an mTOR inhibitor (such as a limus drug, for example sirolimus) and an albumin (such as human albumin or human serum albumin), wherein the nanoparticles have an average diameter of no greater than about 150 nm. In some embodiments, the nanoparticle compositions described herein comprises nanoparticles comprising an mTOR inhibitor (such as a limus drug, for example sirolimus) and an albumin (such as human albumin or human serum albumin), wherein the nanoparticles have an average diameter of no greater than about 150 nm (for example about 100 nm). In some embodiments, the nanoparticle compositions described herein comprises nanoparticles comprising sirolimus and human albumin (such as human serum albumin), wherein the nanoparticles have an average diameter of no greater than about 150 nm (for example about 100 nm).

In some embodiments, the nanoparticle compositions described herein comprise nanoparticles comprising an mTOR inhibitor (such as a limus drug, for example sirolimus) and an albumin (such as human albumin or human serum albumin), wherein the nanoparticles have an average diameter of no greater than about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) and an albumin (such as human albumin or human serum albumin), wherein the nanoparticles have an average diameter of no greater than about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) and an albumin (such as human albumin or human serum albumin), wherein the nanoparticles have an average diameter of about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising sirolimus and human albumin (such as human serum albumin), wherein the nanoparticles have an average diameter of no greater than about 150 nm (for example about 100 nm), wherein the weight ratio of albumin and sirolimus inhibitor in the composition is about 9:1 or about 8:1.

In some embodiments, the nanoparticle compositions described herein comprise nanoparticles comprising an mTOR inhibitor (such as a limus drug, for example sirolimus) associated (e.g., coated) with an albumin (such as human albumin or human serum albumin). In some embodiments, the nanoparticle compositions described herein comprises nanoparticles comprising an mTOR inhibitor (such as a limus drug, for example sirolimus) associated (e.g., coated) with an albumin (such as human albumin or human serum albumin), wherein the nanoparticles have an average diameter of no greater than about 150 nm. In some embodiments, the nanoparticle compositions described herein comprises nanoparticles comprising an mTOR inhibitor (such as a limus drug, for example sirolimus) associated (e.g., coated) with an albumin (such as human albumin or human serum albumin), wherein the nanoparticles have an average diameter of no greater than about 150 nm. In some embodiments, the nanoparticle compositions described herein comprises nanoparticles comprising an mTOR inhibitor (such as a limus drug, for example sirolimus) associated (e.g., coated) with an albumin (such as human albumin or human serum albumin), wherein the nanoparticles have an average diameter of no greater than about 150 nm (for example about 100 nm). In some embodiments, the nanoparticle compositions described herein comprises nanoparticles comprising sirolimus associated (e.g., coated) with human albumin (such as human serum albumin), wherein the nanoparticles have an average diameter of no greater than about 150 nm (for example about 100 nm).

In some embodiments, the nanoparticle compositions described herein comprise nanoparticles comprising an mTOR inhibitor (such as a limus drug, for example sirolimus) associated (e.g., coated) with an albumin (such as human albumin or human serum albumin), wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) associated (e.g., coated) with an albumin (such as human albumin or human serum albumin), wherein nanoparticles have an average diameter of no greater than about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) associated (e.g., coated) with an albumin (such as human albumin or human serum albumin), wherein the nanoparticles have an average diameter of no greater than about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) associated (e.g., coated) with an albumin (such as human albumin or human serum albumin), wherein the nanoparticles have an average diameter of about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising sirolimus associated (e.g., coated) with human albumin (such as human serum albumin), wherein the nanoparticles have an average diameter of no greater than about 150 nm (for example about 100 nm), wherein the weight ratio of albumin and the sirolimus in the composition is about 9:1 or about 8:1.

In some embodiments, the nanoparticle compositions described herein comprise nanoparticles comprising an mTOR inhibitor (such as a limus drug, for example sirolimus) stabilized by an albumin (such as human albumin or human serum albumin). In some embodiments, the nanoparticle compositions described herein comprises nanoparticles comprising an mTOR inhibitor (such as a limus drug, for example sirolimus) stabilized by an albumin (such as human albumin or human serum albumin), wherein the nanoparticles have an average diameter of no greater than about 150 nm. In some embodiments, the nanoparticle compositions described herein comprises nanoparticles comprising an mTOR inhibitor (such as a limus drug, for example sirolimus) stabilized by an albumin (such as human albumin or human serum albumin), wherein the nanoparticles have an average diameter of no greater than about 150 nm. In some embodiments, the nanoparticle compositions described herein comprises nanoparticles comprising an mTOR inhibitor (such as a limus drug, for example sirolimus) stabilized by an albumin (such as human albumin or human serum albumin), wherein the nanoparticles have an average diameter of no greater than about 150 nm (for example about 100 nm). In some embodiments, the nanoparticle compositions described herein comprises nanoparticles comprising sirolimus stabilized by human albumin (such as human serum albumin), wherein the nanoparticles have an average diameter of no greater than about 150 nm (for example about 100 nm).

In some embodiments, the nanoparticle compositions described herein comprise nanoparticles comprising an mTOR inhibitor (such as a limus drug, for example sirolimus) stabilized by an albumin (such as human albumin or human serum albumin), wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) stabilized by an albumin (such as human albumin or human serum albumin), wherein the nanoparticles have an average diameter of no greater than about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) stabilized by an albumin (such as human albumin or human serum albumin), wherein the nanoparticles have an average diameter of no greater than about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising an mTOR inhibitor (such as a limus drug, for example sirolimus) stabilized by an albumin (such as human albumin or human serum albumin), wherein the nanoparticles have an average diameter of about 150 nm, wherein the weight ratio of the albumin and the mTOR inhibitor in the composition is no greater than about 9:1 (such as about 9:1 or about 8:1). In some embodiments, the nanoparticle compositions described herein comprises nanoparticles comprising sirolimus stabilized by human albumin (such as human serum albumin), wherein the nanoparticles have an average diameter of no greater than about 150 nm (for example about 100 nm), wherein the weight ratio of albumin and the sirolimus in the composition is about 9:1 or about 8:1.

In some embodiments, the nanoparticle composition comprises Nab-sirolimus. In some embodiments, the nanoparticle composition is Nab-sirolimus. Nab-sirolimus is a formulation of sirolimus stabilized by human albumin USP, which can be dispersed in directly injectable physiological solution. The weight ratio of human albumin and sirolimus is about 8:1 to about 9:1. When dispersed in a suitable aqueous medium such as 0.9% sodium chloride injection or 5% dextrose injection, Nab-sirolimus forms a stable colloidal suspension of sirolimus. The mean particle size of the nanoparticles in the colloidal suspension is about 100 nanometers. Since HSA is freely soluble in water, Nab-sirolimus can be reconstituted in a wide range of concentrations ranging from dilute (0.1 mg/ml sirolimus) to concentrated (20 mg/ml sirolimus), including for example about 2 mg/ml to about 8 mg/ml, or about 5 mg/ml.

Methods of making nanoparticle compositions are known in the art. For example, nanoparticles containing mTOR inhibitor (such as a limus drug, e.g., sirolimus) and an albumin (such as human serum albumin or human albumin) can be prepared under conditions of high shear forces (e.g., sonication, high pressure homogenization, or the like). These methods are disclosed in, for example, U.S. Pat. Nos. 5,916,596; 6,506,405; 6,749,868, 6,537,579 and 7,820,788 and also in U.S. Pat. Pub. Nos. 2007/0082838, 2006/0263434 and PCT Application WO08/137148.

Briefly, the mTOR inhibitor (such as a limus drug, e.g., sirolimus) is dissolved in an organic solvent, and the solution can be added to an albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

mTOR Inhibitor

The methods described herein in some embodiments comprise administration of nanoparticle compositions of mTOR inhibitors. "mTOR inhibitor" used herein refers to an inhibitor of mTOR. mTOR is a serine/threonine-specific protein kinase downstream of the phosphatidylinositol 3-kinase (PI3K)/Akt (protein kinase B) pathway, and a key regulator of cell survival, proliferation, stress, and metabolism. mTOR pathway dysregulation has been found in many human carcinomas, and mTOR inhibition produced substantial inhibitory effects on tumor progression. In some embodiments, the mTOR inhibitor is an mTOR kinase inhibitor.

The mammalian target of rapamycin (mTOR) (also known as mechanistic target of rapamycin or FK506 binding protein 12-rapamycin associated protein 1 (FRAP1)) is an atypical serine/threonine protein kinase that is present in two distinct complexes, mTOR Complex 1 (mTORC1) and mTOR Complex 2 (mTORC2). mTORC1 is composed of mTOR, regulatory-associated protein of mTOR (Raptor), mammalian lethal with SEC13 protein 8 (MLST8), PRAS40 and DEPTOR (Kim et al. (2002). Cell 110: 163-75; Fang et al. (2001). Science 294 (5548): 1942-5). mTORC1 integrates four major signal inputs: nutrients (such as amino acids and phosphatidic acid), growth factors (insulin), energy and stress (such as hypoxia and DNA damage). Amino acid availability is signaled to mTORC1 via a pathway involving the Rag and Ragulator (LAMTOR1-3) Growth factors and hormones (e.g. insulin) signal to mTORC1 via Akt, which inactivates TSC2 to prevent inhibition of mTORC1. Alternatively, low ATP levels lead to the AMPK-dependent activation of TSC2 and phosphorylation of raptor to reduce mTORC1 signaling proteins.

Active mTORC1 has a number of downstream biological effects including translation of mRNA via the phosphorylation of downstream targets (4E-BP1 and p70 S6 Kinase), suppression of autophagy (Atg13, ULK1), ribosome biogenesis, and activation of transcription leading to mitochondrial metabolism or adipogenesis. Accordingly, mTORC1 activity promotes either cellular growth when conditions are favorable or catabolic processes during stress or when conditions are unfavorable.

mTORC2 is composed of mTOR, rapamycin-insensitive companion of mTOR (RICTOR), GβL, and mammalian stress-activated protein kinase interacting protein 1 (mSIN1). In contrast to mTORC1, for which many upstream signals and cellular functions have been defined (see above), relatively little is known about mTORC2 biology. mTORC2 regulates cytoskeletal organization through its stimulation of F-actin stress fibers, paxillin, RhoA, Rac1, Cdc42, and protein kinase C α (PKCα). It had been observed that knocking down mTORC2 components affects actin polymerization and perturbs cell morphology (Jacinto et al. (2004). Nat. Cell Biol. 6, 1122-1128; Sarbassov et al. (2004). Curr. Biol. 14, 1296-1302). This suggests that mTORC2 controls the actin cytoskeleton by promoting protein kinase Cα (PKCα) phosphorylation, phosphorylation of paxillin and its relocalization to focal adhesions, and the GTP loading of RhoA and Rac1. The molecular mechanism by which mTORC2 regulates these processes has not been determined.

In some embodiments, the mTOR inhibitor is an inhibitor of mTORC1. In some embodiments, the mTOR inhibitor is an inhibitor of mTORC2.

In some embodiments, the mTOR inhibitor is a limus drug, which includes sirolimus and its analogues. Examples of limus drugs include, but are not limited to, temsirolimus (CCI-779), everolimus (RAD001), ridaforolimus (AP-23573), deforolimus (MK-8669), zotarolimus (ABT-578), pimecrolimus, and tacrolimus (FK-506). In some embodiments, the limus drug is selected from the group consisting of temsirolimus (CCI-779), everolimus (RAD001), ridaforolimus (AP-23573), deforolimus (MK-8669), zotarolimus (ABT-578), pimecrolimus, and tacrolimus (FK-506).

In some embodiments, the mTOR inhibitor is sirolimus. Sirolimus is macrolide antibiotic that complexes with FKBP-12 and inhibits the mTOR pathway by binding mTORC1.

In some embodiments, the mTOR inhibitor is selected from the group consisting of sirolimus (rapamycin), BEZ235 (NVP-BEZ235), everolimus (also known as RAD001, Zortress, Certican, and Afinitor), AZD8055, temsirolimus (also known as CCI-779 and Torisel), PI-103, Ku-0063794, INK 128, AZD2014, NVP-BGT226, PF-04691502, CH5132799, GDC-0980 (RG7422), Torin 1, WAY-600, WYE-125132, WYE-687, GSK2126458, PF-05212384 (PKI-587), PP-121, OSI-027, Palomid 529, PP242, XL765, GSK1059615, WYE-354, and eforolimus (also known as ridaforolimus or deforolimus).

BEZ235 (NVP-BEZ235) is an imidazoquilonine derivative that is an mTORC1 catalytic inhibitor (Roper J, et al. PLoS One, 2011, 6(9), e25132). Everolimus is the 40-O-(2-hydroxyethyl) derivative of rapamycin and binds the cyclophilin FKBP-12, and this complex also mTORC1. AZD8055 is a small molecule that inhibits the phosphorylation of mTORC1 (p70S6K and 4E-BP1). Temsirolimus is a small molecule that forms a complex with the FK506-binding protein and prohibits the activation of mTOR when it resides in the mTORC1 complex. PI-103 is a small molecule that inhibits the activation of the rapamycin-sensitive (mTORC1) complex (Knight et al. (2006) Cell. 125: 733-47). KU-0063794 is a small molecule that inhibits the phosphorylation of mTORC1 at Ser2448 in a dose-dependent and time-dependent manner. INK 128, AZD2014, NVP-BGT226, CH5132799, WYE-687, and are each small molecule inhibitors of mTORC1. PF-04691502 inhibits mTORC1 activity. GDC-0980 is an orally bioavailable small molecule that inhibits Class I PI3 Kinase and TORC1. Torin 1 is a potent small molecule inhibitor of mTOR. WAY-600 is a potent, ATP-competitive and selective inhibitor of mTOR. WYE-125132 is an ATP-competitive small molecule inhibitor of mTORC1. GSK2126458 is an inhibitor of mTORC1. PKI-587 is a highly potent dual inhibitor of PI3Kα, mTOR asγ and mTOR. PP-121 is a multi-target inhibitor of PDGFR, Hck, mTOR, VEGFR2, Src and Abl. OSI-027 is a selective and potent dual inhibitor of mTORC1 and mTORC2 with IC50 of 22 nM and 65 nM, respectively. Palomid 529 is a small molecule inhibitor of mTORC1 that lacks affinity for ABCB1/ABCG2 and has good brain penetration (Lin et al. (2013) Int J Cancer DOI: 10.1002/ijc.28126 (e-published ahead of print). PP242 is a selective mTOR inhibitor. XL765 is a dual inhibitor of mTOR/PI3k for mTOR, p110α, p110β, p110γ and p110δ. GSK1059615 is a novel and dual inhibitor of PI3Kα, PI3Kβ, PI3Iδ, PI3Kγ and mTOR. WYE-354 inhibits mTORC1 in HEK293 cells (0.2 μM-5 μM) and in HUVEC cells (10 nM-1 μM). WYE-354 is a potent, specific and ATP-competitive inhibitor of mTOR. Deforolimus (Ridaforolimus, AP23573, MK-8669) is a selective mTOR inhibitor.

In some embodiments, the mTOR kinase inhibitor is selected from the group consisting of CC-115 and CC-223.

Other Components in the Nanoparticle Compositions

The nanoparticles described herein can be present in a composition that include other agents, excipients, or stabilizers. For example, to increase stability by increasing the negative zeta potential of nanoparticles, certain negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. Nos. 5,916,596 and 6,096,331). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Kits, Medicines, Compositions, and Unit Dosages

The invention also provides kits, medicines, compositions, and unit dosage forms for use in any of the methods described herein.

Kits of the invention include one or more containers comprising limus drug-containing nanoparticle compositions (or unit dosage forms and/or articles of manufacture), further comprise instructions for use in accordance with any of the methods described herein. The kit may further comprise a description of selection an individual suitable or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a) a composition comprising nanoparticles comprising mTOR inhibitor (such as a limus drug) and an albumin (such as human serum albumin), and b) instructions for administering the nanoparticle composition for treatment of a PEComa. In some embodiments, the kit comprises a) a composition comprising nanoparticles comprising mTOR inhibitor (such as a limus drug) and an albumin (such as human serum albumin), and b) instructions for administering (such as administering subcutaneously or intravenously) the nanoparticle composition and the other agents for treatment of a PEComa. The nanoparticles and the other agents can be present in separate containers or in a single container. For example, the kit may comprise one distinct composition or two or more compositions wherein one composition comprises nanoparticles and one composition comprises another agent.

The kits of the invention are in suitable packaging. Suitable packaging include, but is not limited to, vials, bottles, jars, flexible packaging (e.g., seled Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the nanoparticle compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the mTOR inhibitor (such as a limus drug, e.g., sirolimus) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the mTOR inhibitor (such as a limus drug) and pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein. In some embodiments, there is provided a medicine (or composition) for use in treating a PEComa, comprising nanoparticles comprising an mTOR inhibitor (such as a limus drug) and an albumin (such as human serum albumin).

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1

Phase II Study Multi-Center Study with Patients Receiving ABI-009 Treatment

Patients with advanced malignant PEComa who previously have not been treated with an mTOR inhibitor were enrolled in a phase II study, single arm, open label, multi-institutional study to assess the efficacy and safety profile of intravenous ABI-009 (also referred to herein as Nab-sirolimus or Nab-rapamycin). If futility criteria are not met, the Stage 2 will open to enrollment.

At least 30 patients will be enrolled in the study. Malignant PEComa histology may be assessed locally in each institution for enrollment but will have to be retrospectively confirmed by a centralized review for every patient after enrollment to meet prespecified criteria for malignant PEComa as outlined in the inclusion criteria. If a patient does not retrospectively meet these criteria, a replacement will be considered.

A patient will be eligible for inclusion in this study only if all of the following criteria are met: (i) patients must have a histologically confirmed diagnosis of advanced malignant PEComa; (ii) patients must have available tumor block along with the corresponding pathology report (or approximately 30 unstained slides, with a minimum of 16 slides is mandatory), and/or fresh biopsy to allow retrospective centralized confirmation of malignant PEComa and for mTOR pathway analysis and biomarker analysis; (iii) patients must have one or more measurable target lesions by CT scan or MRI or measurable disease by RECIST v1.1; (iv) patients must not have been previously treated with an mTOR inhibitor; (v) prior treatment (investigational or other), chemotherapy, radiotherapy, surgery, or other therapeutic agents (except mTOR inhibitors) is allowed, if completed after 5 half-lives or ≥28 days prior to enrollment, whichever is shorter; (vi) eligible patients, 18 years or older, with Eastern Cooperative Oncology Group (ECOG) performance status 0 or 1; (vii) patients must have the following blood chemistry levels at screening (obtained ≤14 days prior to enrollment (local laboratory): (a) total bilirubin ≤1.5×upper limit of normal (ULN) mg/dl, (b) AST ≤2.5×ULN (≤5×ULN if attributable to liver metastases), (c) serum creatinine ≤1.5× ULN; (viii) adequate biological parameters as demonstrated by the following blood counts at screening (obtained ≤14 days prior to enrollment, local laboratory): (a) absolute neutrophil count (ANC) ≥1.5×109/L, (b) platelet count ≥100,000/mm3 (100×109/L), (c) hemoglobin ≥9 g/dL; (ix) urine protein <2 g proteinuria/24 hr; (x) serum triglyceride <300 mg/dL; serum cholesterol <350 mg/dL; (xi) male or non-pregnant and non-breast feeding female (females of child-bearing potential must agree to use effective contraception without interruption from 28 days prior to starting IP and while on study medication and have a negative serum pregnancy test (β-hCG) result at screening and agree to ongoing pregnancy testing during the course of the study, and after the end of study treatment and male patients must practice abstinence or agree to use a condom during sexual contact with a pregnant female or a female of childbearing potential while participating in the study, even if he has undergone a successful vasectomy); (xii) life expectancy of >3 months, as determined by the investigator; (xiii) ability to understand and sign informed consent; (xiv) willingness and ability to comply with scheduled visits, laboratory tests, and other study procedures.

A patient will not be eligible for inclusion in this study if any of the following criteria apply: (i) patients with lymphangioleiomyomatosis (LAM) are excluded; (ii) known active uncontrolled or symptomatic central nervous system (CNS) metastases (a patient with controlled and asymptomatic CNS metastases may participate in this study. As such, the patient must have completed any prior treatment for CNS metastases ≥28 days (including radiotherapy and/or surgery) prior to start of treatment in this study and should not be receiving chronic corticosteroid therapy for the CNS metastases); (iii) active gastrointestinal bleeding, if transfusion dependent; (iv) pre-existing thyroid abnormality is allowed provided thyroid function can be controlled with medication; (v) uncontrolled serious medical or psychiatric illness. Patients with a "currently active" second malignancy other than non-melanoma skin cancers, carcinoma in situ of the cervix, resected incidental prostate cancer (staged pT2 with Gleason Score ≤6 and postoperative PSA <0.5 ng/mL), or other adequately treated carcinoma-in-situ are ineligible (patients are not considered to have a "currently active" malignancy if they have completed therapy and are free of disease for ≥1 year); (vi) liver-directed therapy within 2 months of enrollment (prior treatment with radiotherapy (including radio-labeled spheres and/or cyberknife, hepatic arterial embolization (with or without chemotherapy) or cyrotherapy/ablation) is allowed if these therapies did not affect the areas of measurable disease being used for this protocol); (vii) recent infection requiring systemic anti-infective treatment that was completed ≤14 days prior to enrollment (with the exception of uncomplicated urinary tract infection or upper respiratory tract infection); (viii) uncontrolled diabetes mellitus as defined by HbA1c >8% despite adequate therapy, unstable coronary artery disease or myocardial infarction during preceding 6 months; (ix) receiving any concomitant antitumor therapy; (x) patients with history of interstitial lung disease and/or pneumonitis, or pulmonary hypertension; (xi) the use of certain medications and illicit drugs within 5 half-lives or 28 days, whichever is shorter prior to the first dose of study drug and for the duration of the study will not be allowed (xii) use of strong inhibitors and inducers of CYP3A4 within the 14 days prior to receiving the first dose of ABI-009. Additionally, use of any known CYP3A4 substrates with narrow therapeutic window (such as fentanyl, alfentanil, astemizole, cisapride, dihydroergotamine, pimozide, quinidine, terfanide) within the 14 days prior to receiving the first dose of ABI-009.

The study is expected to take approximately 32 months from first patient enrolled to last patient follow-up, including approximately 24 months of enrollment period, an estimated 6 months of treatment (or until treatment is no longer tolerated) and an end of treatment visit at 4 weeks (+/−7 days) after last treatment.

The following assessments will be performed on Day 1 of each cycle, unless otherwise specified: (i) physical examination; (ii) weight assessment; (iii) BSA calculation; (iv) concomitant medication and procedures evaluation; (v) vital signs (such as temperature, systolic and diastolic blood pressure, and pulse); (vi) ECOG performance status; (vii) ECG; (viii) clinical chemistry panel (including but not limited to sodium, potassium, chloride, glucose, alkaline phosphatase (ALP), AST/SGOT, ALT/SGPT, serum albumin); (ix) CBC, differential and platelet count; (x) thyroid function; (xi) screening for hepatitis and HIV infection (every odd numbered cycle starting with C3); (xii) fasting lipids (every even numbered cycle starting with C2); (xiii) adverse event assessment; (xiv) pharmacokinetics assessment (only on Cycle 1 Day 1).

The following assessments will be performed on Day 8 of each cycle, unless otherwise specified: (i) concomitant medication and procedures evaluation; (ii) vital signs; (iii) CBC, differential and platelet count; (iv) thyroid function; (v) adverse event assessment; (vi) pharmacokinetics assessment (only on Cycle 1 Day 8).

Tumor response will be assessed by CT or MRI scan of the chest, abdomen, and pelvis; image preparation and evaluation will follow the specifications provided in the RECIST version 1.1. The same modality (CT or MRI) must be used at screening and throughout the study.

The End of Study (EOS) defined as either the date of the last visit of the last patient to complete the study, or the date of receipt of the last data point from the last patient that is required for primary, secondary, and/or exploratory analysis, as pre-specified in the protocol.

End of Treatment (EOT) for a patient is defined as the date of the last dose of ABI-009. End of Treatment Visit for a patient is when safety assessments and procedures are performed after the last treatment, which must occur at least 4 weeks (±7 days) after the last dose of ABI-009.

Follow-up period is the on-study time period after the EOT Visit. All patients that discontinue study drug and have not withdrawn full consent to participate in the study will continue in the follow-up phase for survival and initiation anticancer therapy. Follow up will continue approximately every 12 weeks (+/−3 weeks), until death, withdrawal of consent, or the study closes, whichever is the earliest. This evaluation may be made by record review and/or telephone contact.

A PK study of rapamycin will be performed with limited PK sampling on all patients in this phase 2 study. Blood samples will be obtained only during cycle 1, day 1 (C1D1) and will be taken immediately predose (before infusion), 0.5 hr (immediately before termination of infusion), 1 hour, 2 hour, 4 hour and at 168 hour (just prior to dosing on C1D8). Note that T=0 is defined as the start of infusion, i.e., all sample collection times are relative to the start of infusion. The sample at the end of the infusion (0.5 hour) is collected immediately before the infusion is stopped. If the duration of infusion is changed, the sample should be collected immediately before termination of the infusion. Whole-blood samples will be collected in EDTA tubes for determination of rapamycin in a central laboratory.

Patients will receive ABI-009 100 mg/m$^2$ for 2 of every 3 weeks by IV infusion over 30 minutes. Two dose reduction levels will be allowed: 75 mg/m$^2$ and 56 mg/m$^2$. Patients will continue to therapy until disease progression, unacceptable toxicity, until in the opinion of the investigator the patient is no longer benefiting from therapy, or at the patients discretion.

Patients will be evaluated for complete response (CR), partial response (PR), stable disease (SD), or progressive disease (PD) by CT imaging. Contrast enhanced MRI can also be used, as long as the same modality is used throughout the study. Baseline scan results can be accepted from outside institutions, but must be done within 4 weeks of starting therapy and must include (as clinically indicated), chest abdominal, and pelvic CT or MRI. The first response assessment by CT or MRI scans documenting target lesions will be done 6 weeks after first treatment and should be repeated every 6 weeks for the first year, then every 12 weeks thereafter until disease progression. If an initial observation of objective response (CR or PR) is made, a confirmation scan should be done at 6 weeks after initial observation.

The primary endpoint, ORR, will be determined by independent radiologist(s). The independent radiologic review will follow a separate imaging charter.

After disease progression, patients will be followed for survival every 12 weeks, or more frequently as needed, until death, withdrawal of consent, or the study closes, whichever is the earliest.

Safety and tolerability will be monitored through continuous reporting of treatment and treatment-related adverse events (AEs), AEs of special interest, laboratory abnormalities, and incidence of patients experiencing dose modifications, dose delay/dose not given, dose interruptions, and/or premature discontinuation of IP due to an AE. All AEs will be recorded by the investigator from the time the patient signs informed consent until 28 days after the last dose of IP. Adverse events will be graded by National Cancer Institute (NCI) Common Terminology Criteria for Adverse Events (CTCAE) v4.03.

Physical examination, vital sign, laboratory assessments (eg, serum chemistry, hematology), and ECOG performance status will be monitored. All SAEs (regardless of relationship to IP) will be followed until resolution. Laboratory analysis will be performed as per study schedule.

A primary analysis will address all study objectives and it will be conducted when all patients have had the opportunity to be treated for at least 6 months. All primary, secondary, and exploratory efficacy and safety analyses will be conducted at the time of the primary analysis, with the exception of the biomarkers which may be analyzed at a later date.

The primary endpoint is ORR by independent radiologic review, and is defined as the proportion of patients who achieve a confirmed PR or CR per RECIST 1.1.

This study is designed to test whether the confirmed ORR in patients treated with ABI-009 is greater than 5% as determined with the use of the exact binomial 1-sided test with type 1 error of 0.025. With approximately 30 patients the study will provide greater than 95% power to reject the null hypothesis that the ORR is ≤5% given a true response rate of 30%. In addition to the hypothesis test, the number and percentage of patients achieving ORR will be summarized and an exact 95% confidence will be provided. Assuming an observed ORR of 30%, the lower bound of the 95% confidence interval (CI) for the estimated ORR will exclude values less than 14.7%.

Analysis of secondary efficacy endpoints PFS, PFS rate at 6 months, DOR, and OS will be done separately for 2 subgroups of patients: 1) those with metastatic disease; and 2) those with unresectable locally advanced disease or resectable with multiple resections. Some of the patients in the locally advanced subgroup may be clinically indicated to receive surgery if there is sufficient tumor shrinkage, which would introduce a bias to the analysis.

For patients with metastatic disease, PFS at 6 months, median PFS, DOR, and OS will be summarized using Kaplan-Meier (KM) analysis. Quartiles with 95% CIs will be summarized. The number of patients with unresectable locally advanced disease or resectable with multiple resections is expected to be small; therefore PFS (median and at 6 months), DOR, and OS for these patients will be summarized by descriptive statistics.

A key objective of the tumor molecular profiling is to identify specific markers that are predictive of response to ABI-009.

Blood samples will be obtained for cell-free plasma DNA collection (pre- and post-treatment samples, mandatory): molecular analysis of cell-free plasma DNA assay using next-generation sequencing to assess the prevalence of mutations identified in the primary tumor sample over time as a measure of response to therapy.

Tumor biopsy mutation analysis or epigenetic changes will also be completed. Archival or fresh tissue biopsies from pre-treatment tumors are required from patients on this study (mandatory). In addition, on-treatment biopsies will be performed to assess pharmacodynamic effects if available. After the last treatment and at the time of progression, if a biopsy is performed, a tumor sample will be collected. Tumor biopsies are to be collected and pharmacodynamic changes analyzed to determine the effect of the drug on target(s) in the tumor as well as to potentially analyze molecular mechanisms associated with acquired resistance. Exome sequencing using the ONCOPANEL™ test (BWH Pathology Department, CLIA certified) of approximately 300 genes will be performed to assess mutations in all the known mTOR pathway genes, including but not limited to PIK3CA, TSC1, TSC2, AKT, PTEN, MTOR, and RHEB. Evaluation of correlations of clinical response to the therapy will be conducted as well as testing the correlation between biopsy and circulating DNA analyses. FISH (fluorescence in-situ hybridization) analysis of translocations in TFE3 will be completed. These studies will be performed in the Center of Advanced Molecular Diagnostics laboratory at Brigham and Women's Hospital, Boston, Massachusetts, also CLIA certified.

Immunohistochemistry on relevant pathway markers, including but not limited to: phosphoproteins p-AKT, p-S6, p-S6K, p-4EBP1, and p-SPARC; proliferation markers, such as Ki-67; and apoptosis markers, such as PARP or fragments thereof, will be completed. Post-treatment (progression) samples will be analyzed by similar exome sequencing as above, to search for causes of resistance, including secondary mutations and genomic amplification or deletion events.

Example 2

Clinical Pilot Study of Nab-Sirolimus in mTOR Pathway Aberrant Malignancies

A single-arm, phase II clinical trial is designed to assess the efficacy of Nab-sirolimus (also referred to as ABI-009) in an individual with a PEComa and a mutation status of an mTOR pathway gene, particularly, individuals with a mutation status of a gene that would confer sensitivity to mTOR inhibitors (such as a composition comprising nanoparticles comprising a limus drug and an albumin). The gene mutation status is identified via next-generation sequencing experiments from individuals in the clinical study. A primary goal of the study is to assess the response rate of Nab-sirolimus in individuals with a PEComa and an mTOR-activating gene mutation status. Secondary goals are to (1) estimate time to progression and overall survival of the selected individuals; and (2) estimate an adverse events profile of Nab-sirolimus in the selected individuals. Additionally, correlative research is performed to assess the rate of an individual mTOR-activating gene mutation status and assess the association between the individual mTOR-activating gene mutation status and clinical outcome for individuals with a PEComa.

A single group of individuals are enrolled in the clinical study. Prior to registration, individuals are assessed in a CLIA certified lab for mTOR-activating gene mutations in at least one mTOR-associated genes selected from the group consisting of AKT1, MTOR, PIK3CA, PIK3CG, TSC1, TSC2, RHEB, STK11, NF1, NF2, PTEN, TP53, FGFR4, and BAP1, for example. Individuals having at least one mTOR-activating gene mutation and meeting all inclusion criteria are selected for the treatment. An archival paraffin embedded (PPFE) tissue sample may optionally be obtained from each individual. The selected individuals are administered Nab-sirolimus intravenously at a dosage of about 75 mg/m$^2$ on days 1, 8, and 15 of a 28-day cycle, or about 100 mg/m$^2$ on days 1, and 8 of a 21-day cycle. The Nab-sirolimus is infused over about 30 minutes during each administration. The individuals continue to receive Nab-sirolimus treatment and are actively monitored until the occurrence of disease progression and/or unacceptable adverse events, or until the individual refuses to receive the treatment. If multiple adverse events are observed, the dose of Nab-sirolimus may be interrupted or reduced to allow management of drug-related toxicities. For example, the dose of Nab-sirolimus may be first reduced to 56 mg/m$^2$ IV on days 1, 8, and 15 of a 28-day cycle, and then for a second time reduced to 45 mg/m$^2$ IV on days 1, 8, and 15 of a 28-day cycle. Only two dose reductions are allowed per individual. Ancillary treatments, such as antiemetics, growth factors (G-CSF), bisphosphonates or denosumab for pre-existing, painful bone metastases, blood and blood products, warfarin or LMWH, and/or loperamide for diarrhea may be permitted at physician's discretion. The individuals must return to the consenting institution for treatment and evaluation at least every 28 days (or every about 25 to about 31 days) during the treatment. Biomarkers (such as sequences and levels of AKT1, MTOR, PIK3CA, TSC1, TSC2, RHEB, STK11, NF1, NF2, and PTEN, and level of phosphorylated 4EBP1 and S6) are evaluated for each individual on Day 1 of cycle 1, Day 1 (±3 days) of cycle 2, and Day 1 (±3 days) of Cycle 3 and then every 2 cycles afterward. A blood sample is collected from each individual to analyze circulating (e.g., cell-free) DNA before and after the entire course of treatment.

Various biological samples are collected from each individual during the course of the study (e.g., before treatment, on-treatment, and post-treatment), and the biological samples are used to assess the mutational status and level of relevant biomarkers. On-treatment biological samples may be collected from the individual, for example, on Day 1 of cycle 1, Day 1 (±3 days) of cycle 2, and Day 1 (±3 days) of Cycle 3 and then every 2 cycles afterward. A blood sample is collected from each individual before and after the treatment. A cell-free plasma DNA sample is prepared from each blood sample for assessment of circulating DNA. The cell-free plasma DNA samples are analyzed using next-generation sequencing methods to assess the prevalence of the mTOR-activating gene mutations identified in the primary tumor sample over time as a measure of response to the treatment. Additionally, fresh or archival (such as PPFE) tumor biopsy samples are collected from each individual before the treatment, and optionally during the course of the treatment (i.e. on-treatment). The on-treatment tumor biopsy samples are used to assess pharmacodynamics effects of Nab-sirolimus in the individuals. Post-treatment tumor biopsy samples are collected from each individual at the time of disease progression after response to the treatment to assess mechanisms of resistance, including secondary mutations, genomic amplifications, or gene deletion events. Exome sequencing experiments using the ONCOPANEL™ test of approximately 300 genes are performed to assess mutations in mTOR pathway genes, including, but not limited to, PIK3CA, TSC1, TSC2, AKT, PTEN, MTOR, and RHEB. Additionally, mTOR-activating aberrations (such as sequences and levels of biomarkers, including, but not limited to, AKT1, MTOR, PIK3CA, PIK3CG, TSC1, TSC2, RHEB, STK11, NF1, NF2, PTEN, TP53, FGFR4, and BAP1), and level of phosphorylated AKT (i.e. p-AKT), 4EBP1 (i.e. p-4EBP1) and S6K (i.e. p-S6K) are evaluated using the tumor biopsy samples. Proliferation markers (such as Ki-67) and apoptosis markers (such as PARP) may be assessed using immunohistochemistry methods. FISH (fluorescence in-situ hybridization) analysis of translocations in TFE3 is performed. The assessment results are used to evaluate correlation of the mTOR-activating gene mutations to clinical response to the treatment, and to test the correlation between mTOR-activating gene mutations identified in tumor biopsy samples and circulating DNA.

The primary endpoint of this study is the proportion of confirmed responses. In PEComas, a confirmed response is defined to be either a CR or PR, noted as the objective status on two consecutive evaluations at least 8 weeks apart. Confirmed response will be evaluated during all cycles of treatment. An exact binomial confidence interval for the true confirmed response proportion is calculated. Secondary endpoints of this study include survival time, time to disease progression, and adverse events. The distribution of survival time and the distribution of time to disease progression are estimated using the method of Kaplan-Meier. For all primary and secondary endpoints, statistical analysis is carried out for the overall patient population and within each disease group.

Correlative research is performed to determine association of the treatment with quality of life and an individual mTOR-activating gene mutation status for the overall group of patients. Quality of life is assessed prior to review of treatment response and discussions of patient's general health since last treatment evaluation. Quality of life is measured using the EORTC QLQ-C30, a 30-item patient-report questionnaire about patient ability to function, symptoms related to the cancer and its treatment, overall health and quality of life, and perceived financial impact of the cancer and its treatment. Scale score trajectories of the quality of life over time are examined using stream plots and mean plots with standard deviation error bars. Changes from baseline at each cycle is statistically tested using paired t-tests, and standardized response means is interpreted after applying Middel's (2002) adjustment using Cohen's (1988) cutoffs: <0.20=trivial; 0.20-<0.50=small; 0.5-<0.8=moderate; and ≥0.8=large. Rate of individual mTOR-activating aberrations is described, and association with confirmed response is investigated using a Fisher's exact test. Associations with time to progression and overall survival are investigated using log-rank tests. One-sided p-values ≤0.10 are considered statistically significant throughout.

Eligible individuals must meet all of the following inclusion criteria: (a) have histological confirmation of a PEComa (such as lymphangioleiomyomatosis); (b) have advanced stage cancer; (c) have at least one mTOR pathway gene mutation confirmed in a CLIA certified lab, and the mTOR pathway mutation is selected from genetic mutations in AKT1, MTOR, PIK3CA, TSC1, TSC2, RHEB, STK11, NF1, NF2, PTEN (e.g. PTEN deletion), TP53, FGFR4, and BAP1; (d) have none of the following treatments: (1) chemotherapy within 4 weeks before treatment with Nab-sirolimus; (2) hormonal therapy within 4 weeks before treatment with Nab-sirolimus; (3) radiotherapy within 4 weeks before treatment with Nab-sirolimus; (4) treatment with nitrosoureas, mitomycin, or extensive radiotherapy within 6 weeks before treatment with Nab-sirolimus; (5) immunosuppressive agents within 3 weeks before treatment with Nab-sirolimus (except corticosteroids used as antiemetics); (6) use of prior mTOR pathway inhibitor therapy; (d) have the following laboratory values obtained no more than 14 days prior to registration: (1) absolute neutrophil count (ANC) ≥1500/mm³, platelet count ≥100,000/mm³; (2) Hemoglobin ≥9.0 g/dL; (3) Total bilirubin ≤1.5× institutional upper limit of normal (ULN); (4) Aspartate transaminase (AST); Alanine Aminotransferase (ALT) ≤3×ULN, or ≤5×ULN if subject has tumor involvement in the liver; (5) Serum cholesterol ≤350 mg/dL; (6) Serum triglyceride ≤300 mg/dL; (7) Serum creatinine ≤1.5×ULN; (e) have previously failed, unable to tolerate, or refused other available active therapies; (f) have adequate coagulation function as defined by either of the following criteria: (1) INR ≤1.5×ULN; (2) For subjects receiving warfarin or LMWH, the subjects must, in the investigator's opinion, be clinically stable with no evidence of active bleeding while receiving anticoagulant therapy.

Exclusion criteria are: (a) pregnant or nursing women, or women of child-bearing potential, who are biologically able to conceive, or men who are able to father a child, not employing two forms of highly effective contraception; (b) patients with a history of interstitial lung disease and/or pneumonia; (c) receiving any concomitant antitumor therapy or inhibitors of CYP3A4; (d) history of allergic reactions attributed to compounds of similar chemical or biologic composition including macrolide (e.g. azithromycin, clarithromycin, dirithromycin, and erythromycin) and ketolide antibiotics; (e) major surgery (e.g., intra-thoracic, intra-abdominal or intra-pelvic) ≤4 weeks prior to registration or failure to recover from side effects of such surgery with the exceptions of port placements, nephrectomy, tumor biopsies, and minor surgeries; (f) concurrent use of any other approved or investigational anticancer agents which would be considered as a treatment for the primary neoplasm; (g) uncontrolled diabetes mellitus as defined by HbA1c >8% despite adequate therapy; (h) unstable coronary artery disease or myocardial infarction during preceding 6 months; and (i) hypertension uncontrolled by medication.

Example 3

Treating Metastatic PEComa with Nab-Sirolimus

A patient with a lung PEComa (previously treated with adjuvant radiation therapy and then surgical resection of the lung PEComa about 5 months prior) presented with a new suspect metastatic lesion on CT scan. The new precarinal (mediastinal) lymph node was approximately 1.5 cm diameter. Since the size of the new lesion was borderline with respect to the entry criteria for the PEC001 (RECIST, requiring measurable disease), the patient was subject to another CT scan approximately 1 month later. At that time the lesion was measurable and the patient also had a new pleural lesion of >2 cm. Given the presence of a new lesion since the last CT scan, the metastatic PEComa was considered as an aggressive tumor that was rapidly progressing. The patient was consented for the PEC001 study and treatment with nab-sirolimus (also referred to as ABI-009) initiated at a dose of 100 mg/m² given by IV infusion over 30 minutes and repeated on a 2 out of 3 week schedule. The next follow-up CT scan was scheduled after 6 weeks as per the PEC001 clinical protocol. During that period the patient received nab-sirolimus according to the protocol, tolerated the drug well and reported no significant adverse events. At the 6 week CT scan follow-up, the lesions showed no change from the previous scan and the disease was considered to be held stable by the treatment with nab-sirolimus. Further treatment and follow-up continue as per the protocol and the patient continues to tolerate the treatment with no significant adverse events.

What is claimed is:

1. A method of treating a malignant perivascular epithelioid tumor (PEComa) in an individual, comprising intravenously administering to the individual an effective amount of a composition comprising nanoparticles comprising sirolimus and an albumin, wherein the effective amount of sirolimus in the nanoparticle composition is about 10 mg/m² to about 100 mg/m², and wherein the nanoparticle composition is administered on days 1 and 8 of a 21-day cycle.

2. The method of claim 1, wherein the malignant PEComa is a pulmonary clear cell 'sugar' tumor or a PEComa not otherwise specified (PEComa-NOS).

3. The method of claim 1, wherein the malignant PEComa is advanced malignant, locally advanced, metastatic, or recurrent.

4. The method of claim 1, wherein the individual has been previously treated with an mTOR inhibitor.

5. The method of claim 1, wherein the effective amount of sirolimus in the nanoparticle composition is less than about 50 mg/m².

6. The method of claim 1, wherein the effective amount of sirolimus in the nanoparticle composition is about 10 mg/m² to about 25 mg/m².

7. The method of claim 1, wherein the effective amount of sirolimus in the nanoparticle composition is about 25 mg/m² to about 50 mg/m².

8. The method of claim 1, wherein the effective amount of sirolimus in the nanoparticle composition is about 10 mg/m² to about 56 mg/m².

9. The method of claim 1, wherein the effective amount of sirolimus in the nanoparticle composition is about 45 mg/m², about 30 mg/m², or about 10 mg/m².

10. The method of claim 1, wherein the method is in a neoadjuvant setting.

11. The method of claim 1, wherein the nanoparticles in the composition have an average diameter of no greater than about 150 nm.

12. The method of claim 1, wherein the albumin is human albumin.

13. The method of claim 1, wherein the albumin is human serum albumin.

14. The method of claim 1, wherein the individual is human.

* * * * *

UNITED STATES PATENT AND TRADEMARK OFFICE
CERTIFICATE OF CORRECTION

PATENT NO. : 12,133,844 B2
APPLICATION NO. : 17/165652
DATED : November 5, 2024
INVENTOR(S) : Neil P. Desai It is certified that error appears in the above-identified patent and that said Letters Patent is hereby corrected as shown below:

On the Title Page

Item (56), page 3, Column 2, Line 52, please delete "Manmalian" and insert -- Mammalian --;

Item (56), page 4, Column 1, Line 28, please delete "Activiation" and insert -- Activation --;

Item (56), page 4, Column 1, Line 53, please delete "Anestestiol." and insert -- Anestesiol. --;

Item (56), page 4, Column 2, Line 2, please delete "Cystalloids" and insert -- Crystalloids --;

Item (56), page 4, Column 2, Line 12, please delete "rapacmycin)" and insert -- rapamycin) --;

Item (56), page 5, Column 2, Line 26, please delete "Apha-Acid" and insert -- Alpha1-Acid --;

Item (56), page 5, Column 2, Line 49, please delete "Epitheliod" and insert -- Epithelioid --;

Item (56), page 6, Column 2, Line 1, please delete "Acture Lymphoblasticd" and insert -- Acute Lymphoblastic --;

In the Specification

At Column 43, Line number 33, please delete "at" and insert -- al. --;

At Column 45, Line number 33, please delete "mg/m$^2$" and insert -- mg/m$^2$, --;

At Column 45, Line number 42, please delete "mg/m$^2$ 22 mg/m$^2$" and insert -- mg/m$^2$, 22 mg/m$^2$, --;

At Column 47, Line number 16, please delete "but 75" and insert -- but is not limited to, about any of 50 mg/m$^2$, 60 mg/m$^2$, 75 --;

Signed and Sealed this
Twenty-fifth Day of February, 2025

Coke Morgan Stewart
*Acting Director of the United States Patent and Trademark Office*

CERTIFICATE OF CORRECTION (continued)
U.S. Pat. No. 12,133,844 B2

At Column 48, Line number 14, after "Application" please insert -- No. --;

At Column 49, Line numbers 52-53, please delete "hypovolumic" and insert -- hypovolemic --;

At Column 50, Line number 7, please delete "Pharmcol." and insert -- Pharmacol. --;

At Column 50, Line number 8, please delete "37999" and insert -- 379-99 --;

At Column 50, Line number 17, please delete "*Anestestiol.*" and insert -- *Anestesiol.* --;

At Column 50, Line number 59, please delete "the the" and insert -- the --;

At Column 55, Line number 32, after "Application" please insert -- No. --;

At Column 57, Line number 1, please delete "imidazoquilonine" and insert -- imidazoquinoline --;

At Column 57, Line number 55, please delete "litocholic" and insert -- lithocholic --;

At Column 57, Line number 60, after "stearoyllinoleoylphosphatidylcholine" please insert -- , --;

At Column 57, Line numbers 65-66, please delete "distearyolphosphatidylcholine" and insert -- distearoylphosphatidylcholine --;

At Column 59, Line number 32, please delete "seled" and insert -- sealed --;

At Column 61, Line number 26, please delete "cyrotherapy" and insert -- cryotherapy --; and At Column 61, Line number 45, please delete "terfanide)" and insert -- terfenadine) --.